US012649830B2

(12) United States Patent
Khan et al.

(10) Patent No.: US 12,649,830 B2
(45) **Date of Patent: *Jun. 9, 2026**

(54) MULTI-MOTIF DENDRONS AND THEIR SUPRAMOLECULAR STRUCTURES AND USES THEREOF

(71) Applicant: The Governing Council of the University of Toronto, Toronto (CA)

(72) Inventors: Omar Fizal Khan, Toronto (CA); Grayson Tilstra, Toronto (CA); Alanna Margaret Manning, Tottenham (CA); Yan Ming Anson Lau, Toronto (CA); Julien Couture-Senécal, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/621,868

(22) Filed: Mar. 29, 2024

(65) Prior Publication Data

US 2024/0247109 A1 Jul. 25, 2024

Related U.S. Application Data

(63) Continuation of application No. PCT/CA2022/051745, filed on Nov. 29, 2022.

(60) Provisional application No. 63/398,936, filed on Aug. 18, 2022, provisional application No. 63/283,588, filed on Nov. 29, 2021.

(51) Int. Cl.
*C08G 83/00* (2006.01)
*A61K 9/51* (2006.01)

(52) U.S. Cl.
CPC .......... *C08G 83/003* (2013.01); *A61K 9/5123* (2013.01)

(58) Field of Classification Search
CPC .................................................... C08G 83/003
See application file for complete search history.

(56) References Cited

U.S. PATENT DOCUMENTS

| | | | |
|---|---|---|---|
| 5,820,873 A | 10/1998 | Choi et al. | |
| 8,450,298 B2 | 5/2013 | Mahon et al. | |
| 2005/0004293 A1 | 1/2005 | Peng et al. | |
| 2017/0121279 A1* | 5/2017 | Siegwart ................ | A61K 47/60 |
| 2025/0186357 A1 | 6/2025 | Couture-senécal et al. | |

FOREIGN PATENT DOCUMENTS

| | | | |
|---|---|---|---|
| CN | 101220119 | * | 7/2008 |
| CN | 104292129 | A | 1/2015 |
| CN | 106519139 | A | 3/2017 |
| CN | 113264842 | A | 8/2021 |
| CN | 113402404 | A | 9/2021 |
| CN | 114262275 | A | 4/2022 |
| EP | 4122920 | A1 | 1/2023 |
| GB | 941753 | A | 11/1963 |
| WO | 2010141069 | A2 | 12/2010 |
| WO | WO-2011123621 | A2 | 10/2011 |
| WO | 2014199174 | A1 | 12/2014 |
| WO | WO-2017118842 | A1 | 7/2017 |
| WO | 2018078053 | A1 | 5/2018 |
| WO | 2020061367 | A1 | 3/2020 |
| WO | 2020132196 | A1 | 6/2020 |
| WO | 2021226597 | A2 | 11/2021 |
| WO | 2022066916 | A1 | 3/2022 |
| WO | 2022168085 | A1 | 8/2022 |
| WO | 2022218295 | A1 | 10/2022 |
| WO | 2023061460 | A1 | 4/2023 |
| WO | 2023092242 | A1 | 6/2023 |
| WO | 2023198085 | A1 | 10/2023 |
| WO | 2025123134 | A1 | 6/2025 |

OTHER PUBLICATIONS

Mizugaki et al. Chemical Communications (2008), (2), 241-243.*
Beigi et al. European Journal of Organic Chemistry (2011), (8), 1482-1492, S1482/1-S1482/39.*
International Search Report and Written Opinion mailed Mar. 6, 2023, International Patent Application No. PCT/CA2022/051745, filed Nov. 29, 2022.
Ball, Rebecca L. et al., PloS One, vol. 10, Issue 7, Jul. 20, 2015.
Yu, Bo et al., Biomaterials, vol. 33, No. 25, pp. 5924-5934, Sep. 1, 2012.
Rousseau, Guillaume et al., CHEMPLUSCHEM, vol. 78, No. 4, pp. 352-363, Apr. 2013.
Simms, Briana I. et al., Journal of Polymer Science, vol. 59, No. 19, pp. 2177-2192, Oct. 1, 2021.
Luxembourg Search Report received for Luxembourg Application No. 505741, mailed on Jun. 19, 2024, 8 pages.
Baiersdorfer et al. (Apr. 15, 2019) "A Facile Method for the Removal of dsRNA Contaminant from In Vitro-Transcribed mRNA", Nucleic Acids—Molecular Therapy, 15:26-35.
Carrasco et al. (Aug. 11, 2021) "Ionization and Structural Properties of mRNA Lipid Nanoparticles Influence Expression in Intramuscular and Intravascular Administration", Communications Biology, 4(1):956 (15 pages).
Dhumal et al. (Nov. 30, 2020) "Experimentally Validated QSAR Model for Surface pKa Prediction of Heterolipids Having Potential as Delivery Materials for Nucleic Acid Therapeutics", ACS Omega, 5(49):32023-32031.

(Continued)

*Primary Examiner* — Ana Z Muresan
(74) *Attorney, Agent, or Firm* — Smart & Biggar LP; Patricia Folkins

(57) ABSTRACT

The present application includes dendrons of Formula I, compositions comprising these dendrons and uses thereof, in particular for the delivery of agents such as nucleic acids and drugs to cells and subjects.

(I)

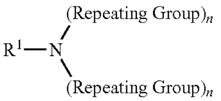

wherein each Repeating Group is the same or different.

18 Claims, 9 Drawing Sheets

Specification includes a Sequence Listing.

(56) References Cited

OTHER PUBLICATIONS

Hassett et al. (Apr. 15, 2019) "Optimization of Lipid Nanoparticles for Intramuscular Administration of mRNA Vaccines", Molecular Therapy—Nucleic Acids, 15:1-11.
Jayaraman et al. (Aug. 20, 2012) "Maximizing the Potency of siRNA Lipid Nanoparticles for Hepatic Gene Silencing In Vivo", Angewandte Chemie International Edition, 51(34):8529-8533.
G. Tilstra et al., "Iterative Design of Ionizable Lipids for Intramuscular mRNA Delivery," J. Am. Chem. Soc. 2023, 145, 2294-2304 (Jan. 18, 2023).
Alameh et al. (2021) "Lipid Nanoparticles Enhance the Efficacy of Mrna and Protein Subunit Vaccines by Inducing Robust T Follicular Helper Cell and Humoral Responses", Immunity, 54(12):2877-2892.
Barbier et al. (2022) "The Clinical Progress of mRNA Vaccines and Immunotherapies", Nature Biotechnology, 40(6):840-854.
Bogers et al. (Oct. 17, 2014) "Potent Immune Responses in Rhesus Macaques Induced by Nonviral Delivery of a Selfamplifying RNA Vaccine Expressing HIV Type 1 Envelope With a Cationic Nanoemulsion", Journal of Infectious Diseases, 211(6):947-955.
Brito et al. (Dec. 2014) "A Cationic Nanoemulsion for the Delivery of Next-generation RNA Vaccines", Molecular Therapy, 22(12):2118-2129.
Chahal et al. (Jul. 19, 2016) "Dendrimer-RNA Nanoparticles Generate Protective Immunity Against Lethal Ebola, H1N1 Influenza, and Toxoplasma Gondii Challenges With a Single Dose", Proceedings of the National Academy of Sciences of the United States of America, 113(29):E4133-E4142.
Chaudhary et al. (Nov. 2021) "mRNA Vaccines for Infectious Diseases: Principles, Delivery and Clinical Translation", Nature Reviews Drug Discovery, 20(11):817-838.
Chen et al. (2012) "Rapid Discovery of Potent Sirna-containing Lipid Nanoparticles Enabled by Controlled Microfluidic Formulation", Journal of the American Chemical Society, 134(16):6948-6951.
Cheng et al. (2020) "Selective Organ Targeting (SORT) Nanoparticles for Tissue-specific mRNA Delivery and CRISPR-Cas Gene Editing", Nature Nanotechnology, 15(4):313-320 (17 pages).
Corbett et al. (Oct. 15, 2020) "Evaluation of the mRNA-1273 Vaccine against SARS-CoV-2 in Nonhuman Primates", The New England Journal of Medicine, 383(16):1544-1555.
Cornebise et al. (Feb. 16, 2022) "Discovery of a Novel Amino Lipid That Improves Lipid Nanoparticle Performance through Specific Interactions with mRNA", Advanced Functional Materials, 32(8):2106727 (12 pages).
Cullis et al. (1986) "Lipid Polymorphism and the Roles of Lipids in Membranes", Chemistry and Physics of Lipids, 40(2-4):127-144.
Geall et al. (Sep. 4, 2012) "Nonviral Delivery of Self-amplifying RNA Vaccines", Proceedings of the National Academy of Sciences, 109(36):14604-14609.
Hafez et al. (2001) "On the Mechanism Whereby Cationic Lipids Promote Intracellular Delivery of Polynucleic Acids", Gene Therapy, 8(15):1188-1196.
Han et al. (Dec. 13, 2021) "An Ionizable Lipid Toolbox for RNA Delivery", Nature Communications, 12(1):7233 (6 pages).
Hekele et al. (2013) "Rapidly Produced Sam Vaccine Against H7N9 Influenza is Immunogenic in Mice", Emerging Microbes and Infections, 2(8):e52 (8 pages).
Heyes et al. (Oct. 2005) "Cationic Lipid Saturation Influences Intracellular Delivery of Encapsulated Nucleic Acids", Journal of Controlled Release, 107(2):276-287.
Jayaraman et al. (Aug. 20, 2012) "Maximizing the Potency of siRNA Lipid Nanoparticles for HepaticGene Silencing In Vivo", Angewandte Chemie, 124(34):8657-8661.
Kariko et al. (2005) "Suppression of RNA Recognition by Toll-like Receptors: The Impact of Nucleoside Modification and the Evolutionary Origin of RNA", Immunity, 23(2):165-175.
Khan et al. (May 13, 2015) "Dendrimer-Inspired Nanomaterials for the in Vivo Delivery of siRNA to Lung Vasculature", Nano Letters, 15(5):3008-3016 (24 pages).
Khan et al. (Dec. 22, 2014) "Ionizable Amphiphilic Dendrimer-based Nanomaterials With Alkyl-chain-substituted Amines for Tunable siRNA delivery to the Liver Endothelium in Vivo", Angewandte Chemie, 53(52):14397-14401.
Labieniec-Watala et al. (2015) "PAMAM Dendrimers: Destined for Success or Doomed to Fail? Plain and Modified PAMAM Dendrimers in the Context of Biomedical Applications", Journal of Pharmaceutical Sciences, 104(1):2-14.
Melamed, et al. (Jan. 2022) "Lipid Nanoparticle Chemistry Determines How Nucleoside Base Modifications Alter mRNA Delivery", Journal of Controlled Release, 341:206-214.
Mendes et al. (Aug. 2017) "Dendrimers as Nanocarriers for Nucleic Acid and Drug Delivery in Cancer Therapy", Molecules, 22(9):1401 (21 pages).
Pardi et al. Apr. 2018) "mRNA Vaccines—a New Era in Vaccinology", Nature Reviews Drug Discovery, 17(4):261-279 (19 pages).
Rajappan et al. (2020) "Property-Driven Design and Development of Lipids for Efficient Delivery of siRNA", Journal of Medicinal Chemistry, 63(21):12992-13012.
Semple et al. (2010) "Rational Design of Cationic Lipids for siRNA Delivery", Nature Biotechnology, 28(2):172-176.
Trepotec et al. (2019) "Maximizing the Translational Yield of mRNA Therapeutics by Minimizing 5'-UTRs", Tissue Engineering Part A, 25(1-2):69-79 (29 pages).
Walsh et al. (2014) "Microfluidic-Based Manufacture of siRNA-Lipid Nanoparticles for Therapeutic Applications", Methods in Molecular Biology, 1141:109-120.
Wei et al. (Jun. 26, 2020) "Systemic Nanoparticle Delivery of CRISPR-Cas9 Ribonucleoproteins for Effective Tissue Specific Genome Editing", Nature Communications, 11(1):3232 (12 pages).
Xu et al. (Aug. 7, 2013) "RNA Replicon Delivery via Lipid-complexed PRINT Protein Particles", Molecular Pharmaceutics, 10(9):3366-3374.
Zhang et al. (2011) "Ionization Behavior of Amino Lipids for Sirna Delivery: Determination of Ionization Constants, SAR, and the Impact of Lipid pKa on Cationic Lipid-biomembrane Interactions", Langmuir, 27(5):1907-1914.
Li et al. (Jul. 31, 2018) "Intracellular Delivery and Biodistribution Study of CRISPR/Cas9 Ribonucleoprotein Loaded Bioreducible Lipidoid Nanoparticles", Biomaterials Science, DOI:10.1039/C8BM00637G, 7(2):596-606.
Wang et al. (Sep. 20, 2016) "Structure-Activity Relationships of Fluorinated Dendrimers in DNA and siRNA Delivery", Acta Biomaterialia, 46:204-210 (7 pages).

* cited by examiner e

| | SM-102 | I-1 | I-18 |
|---|---|---|---|
| Size | 84 nm | 86 nm | 116 nm |
| PDI | 0.11 | 0.18 | 0.12 |
| EE | 99% | 83% | 95% |
| $pK_a$ | 6.6 | 5.5 | 6.2 |

e

| | I-1 | I-26 | I-25 |
|---|---|---|---|
| Size | 148 nm | 173 nm | 152 nm |
| PDI | 0.08 | 0.12 | 0.09 |
| EE | 83% | 93% | 86% |
| $pK_a$ | 5.2 | 6.3 | 4.4 |

a

I-27 e

| | I-26 | I-27 |
|---|---|---|
| Size | 124 nm | 95 nm |
| PDI | 0.11 | 0.15 |
| EE | 97% | 96% |
| $pK_a$ | 6.2 | 7.2 |

a

I-28 I-29 b c d e f

| | SM-102 | I-27 | I-28 | I-29 |
|---|---|---|---|---|
| Size | 86 nm | 119 nm | 95 nm | 102 nm |
| PDI | 0.17 | 0.13 | 0.15 | 0.04 |
| EE | 96% | 96% | 97% | 96% |
| $pK_a$ | 6.6 | 6.9 | 6.8 | 6.8 |

SEQUENCE LISTING

```
Sequence total quantity: 5
SEQ ID NO: 1           moltype = DNA  length = 1808
FEATURE                Location/Qualifiers
source                 1..1808
                       mol_type = other DNA
                       organism = synthetic construct
SEQUENCE: 1
tagaaactgg gcttgtcgag actaatacga ctcactatag ggagactgcc accatggaag  60
acgcgaagaa tatcaagaag ggacctgcac ccttctatcc actggaagac ggcactgctg  120
gagagcagct ccataaggcc atgaagagat acgcactggt gcctggtaca atcgcattta  180
ccgacgctca tattgaggtc gatattacat acgccgaata tttcgagatg tccgtgagac  240
tcgctgaggc aatgaagcgg tacgggctga atactaacca caggatcgtc gtgtgttcag  300
agaacagcct gcagttcttc atgcctgtgc tgggtgctct gttcattggg gttgccgttg  360
ctccagcaaa cgacatttat aacgagaggg aactgcttaa tagcatgggc attagccagc  420
cgacagtggt gtttgtgagt aagaaaggac tccaaaaaat tctgaacgtc cagaaaaaat  480
tacctatcat tcagaagatc atcatcatgg atagcaagac agactaccag ggctttcaga  540
gcatgtatac ctttgtgacc agccacctgc cgccagggtt taacgagtat gatttcgtac  600
ccgaaagctt cgaccgggac aaaaccatcg cattgatcat gaattcctct gggtcaaccg  660
gcctccctaa aggggtagca ctgccacacc gaactgcgtg cgtgcgcttt agccacgcga  720
gggatccaat tttggaaat cagattatcc ccgataccgc catactgtca gtagtgccat  780
tccaccacgg gtttggtatg ttcaccacac ttgggtatct aatctgtgga ttcagagtcg  840
tccttatgta ccgctttgaa gaggaattgt ttcttcgatc cctccaggac tacaaaatcc  900
aatccgcctt attggtgcct actctgttct ccttttttcgc caagagcacg ctgatcgaca  960
aatatgacct gagtaacctc catgagattg ctagcggtgg cgcccccctg agcaaagagg  1020
tgggcgaggc agttgctaag cgcttccatc tccctggaat aagacaggga tacggcctaa  1080
cagagactac aagtgcaatc ttaattacac ccgaaggcga tgacaagccc ggcgctgtgg  1140
gaaaggttgt acctttttttt gaagccaaag tggtcgacct cgatactggc aaaacgctag  1200
gcgtcaacca gcgcggtgag ctatgcgtta ggggccctat gatcatgagt ggttacgtga  1260
acaaccccga agccacgaat gcgctgatcg acaaggatgg atggttgcat tcgggagata  1320
tcgcttattg ggacgaagac gagcacttct tcatagtaga ccgactgaag agcctgatca  1380
agtacaaggg ataccaggtg gctcccgccg agcttgagtc catcctcttg caacacccga  1440
atattttcga tgccggggtg gctgggctgc cagacgatga tgccggcgaa cttccagctg  1500
ccgtcgtagt gctcgagcac gggaagacaa tgaccgaaaa ggagatcgtt gactacgtgg  1560
cctcacaagt gaccactgcc aaaaagcttc ggggaggggt ggtcttcgtc gatgaggtcc  1620
ccaaaggctt gaccggtaag ctcgatgcac ggaagatacg tgaaattctg ataaaggcca  1680
aaaaaggcgg taagatagcc gtttgataag ctgccttctg cggggcttgc cttctggcca  1740
tgcccttctt ctctcccttg cacctgtacc tcttggtctt tgaataaagc ctgagtagga  1800
agagtact                                                           1808

SEQ ID NO: 2           moltype = DNA  length = 22
FEATURE                Location/Qualifiers
source                 1..22
                       mol_type = other DNA
                       organism = synthetic construct
SEQUENCE: 2
tagaaactgg gcttgtcgag ac                                           22

SEQ ID NO: 3           moltype = DNA  length = 27
FEATURE                Location/Qualifiers
source                 1..27
                       mol_type = other DNA
                       organism = synthetic construct
```

-continued

```
SEQUENCE: 3
cttcctactc aggctttatt caaagac                                    27

SEQ ID NO: 4           moltype = DNA  length = 4125
FEATURE                Location/Qualifiers
source                 1..4125
                       mol_type = other DNA
                       organism = synthetic construct
SEQUENCE: 4
atggacaaga agtacagcat cggcctggac atcggcacca actctgtggg ctggccgtg  60
atcaccgacg agtacaaggt gcccagcaag aaattcaagg tgctgggcaa caccgaccgg  120
cacagcatca agaagaacct gatcggcgcc ctgctgttcg acagcggaga aacagccgag  180
gccacccggc tgaagagaac cgccagaaga agatacacca gacggaagaa ccggatctgc  240
tatctgcaag agattttcag caacgagatg gccaaggtgg acgacagctt cttccacaga  300
ctggaagagt ccttcctggt ggaagaggat aagaagcacg agcggcaccc catcttcggc  360
aacatcgtgg acgaggtggc ctaccacgag aagtacccca ccatctacca cctgagaaag  420
aaactggtgg acagcaccga caaggccgac ctgcggctga tctatctggc cctggcccac  480
atgatcaagt tccggggcca cttcctgatc gagggcgacc tgaaccccga caacagcgac  540
gtggacaagc tgttcatcca gctggtgcag acctacaacc agctgttcga ggaaaacccc  600
atcaacgcca gcggcgtgga cgccaaggcc atcctgtctg ccagactgag caagagcaga  660
cggctggaaa atctgatcgc ccagctgccc ggcgagaaga agaatggcct gttcggcaac  720
ctgattgccc tgagcctggg cctgaccccc aacttcaaga gcaacttcga cctggccgag  780
gatgccaaac tgcagctgag caaggacacc tacgacgacg acctggacaa cctgctggcc  840
cagatcggcg accagtacgc cgacctgttt ctggccgcca agaacctgtc cgacgccatc  900
ctgctgagcg acatcctgag agtgaacacc gagatcacca aggcccccct gagcgcctct  960
atgatcaaga gatacgacga gcaccaccag gacctgaccc tgctgaaagc tctcgtgcgg  1020
cagcagctgc ctgagaagta caaagaaatc ttcttcgacc agagcaagaa cggctacgcc  1080
ggctacatcg atggcggagc cagccaggaa gagttctaca agttcatcaa gcccatcctg  1140
gaaaagatgg acggcaccga ggaactgctc gtgaagctga acagagagga cctgctgcgg  1200
aagcagcgga ccttcgacaa cggcagcatc ccccaccaga tccacctggg agagctgcac  1260
gccattctgc ggcggcagga agatttttac ccattcctga aggacaaccg ggaaaagatc  1320
gagaagatcc tgaccttccg catcccctac tacgtgggcc ctctggccag gggaaacagc  1380
agattcgcct ggatgaccag aaagagcgag gaaaccatca cccccctggaa cttcgaggaa  1440
gtggtggaca agggcgccag cgcccagagc ttcatcgagc ggatgaccaa cttcgataag  1500
aacctgccca acgagaaggt gctgcccaag cacagcctgc tgtacgagta cttcaccgtg  1560
tacaacgagc tgaccaaagt gaaatacgtg accgagggaa tgagaaagcc cgccttcctg  1620
agcggcgagc agaaaaaggc catcgtggac ctgctgttca agaccaaccg gaaagtgacc  1680
gtgaagcagc tgaaagagga ctacttcaag aaaatcgagt gcttcgactc cgtggaaatc  1740
tccggcgtgg aagatcggtt caacgcctcc ctgggcacat accacgacct gctgaagatt  1800
atcaaggaca aggacttcct ggacaatgag gaaaacgagg acattctgga agatatcgtg  1860
ctgaccctga cactgtttga ggacagagag atgatcgagg aacggctgaa aacctatgcc  1920
cacctgttcg acgacaaagt gatgaagcag ctgaagcggc ggagatacac cggctggggc  1980
aggctgagcc ggaagctgat caacggcatc cgggacaagc agtccggcaa gacaatcctg  2040
gatttcctga agtccgacgg cttcgccaac agaaacttca tgcagctgat ccacgacgac  2100
agcctgacct ttaaagagga catccagaaa gcccaggtgt ccggccaggg cgatagcctg  2160
cacgagcaca ttgccaatct ggccggatcc cccgccatta agaagggcat cctgcagaca  2220
gtgaagattg tggacgagct cgtgaaagtg atgggccaca agcccgagaa catcgtgatc  2280
gaaatggcca gagagaacca gaccacccag aagggacaga agaacagccg cgagagaatg  2340
aagcggatcg aagagggcat caaagagctg ggcagccaga tcctgaaaga acaccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccacatt  2520
gtgccccagt ccttcatcaa ggacgactcc atcgataaca aagtgctgac tcggagcgac  2580
aagaaccggg gcaagagcga caacgtgccc tccgaagagg tcgtgaagaa gatgaagaac  2640
tactggcgcc agctgctgaa tgccaagctg attacccaga ggaagttcga caatctgacc  2700
aaggccgaga gaggcggcct gagcgaactg gataaggccg gcttcattaa gcggcagctg  2760
gtggaaaccc ggcagatcac aaagcacgtg gcacagatcc tggactcccg gatgaacact  2820
aagtacgacg agaacgacaa actgatccgg gaagtgaaag tgatcaccct gaagtccaag  2880
ctggtgtccg acttcagaaa ggatttccag ttttacaaag tgcgcgagat caacaactac  2940
caccacgccc acgacgccta cctgaacgcc gtcgtgggaa ccgccctgat caaaaagtac  3000
cctaagctgg aaagcgagtt cgtgtacggc gattacaagg tgtacgacgt gcggaagatg  3060
atcgccaaga gcgagcagga aatcggcaag gctaccgcca agtacttctt ctacagcaac  3120
atcatgaact ttttcaagac cgagatcaca ctggccaacg gcgagatcag aaagcggcct  3180
ctgatcgaga caaacggcga aaccggggag atcgtgtggg ataagggccg ggattttgcc  3240
acagtgcgga aagtgctgtc catgccccaa gtgaatatcg tgaaaaagac cgaggtgcag  3300
accggcggct tcagcaaaga gtctatcctg cccaagagga actccgacaa gctgatcgcc  3360
agaaagaagg attgggaccc taagaagtac ggcggcttcg acagccccac cgtggcctac  3420
tctgtgctgg tggtggccaa agtggaaaag ggcaagtcca agaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag cggatgctgg cttctgccgg cgaactgcag  3660
aagggaaacg agctggccct gccctccaaa tatgtgaact tcctgtacct ggccagccac  3720
tatgagaagc tgaagggctc ccccgaggat aatgagcaga aacagctgtt tgtggaacag  3780
cacaagcact acctggacga gatcatcgag cagattagcg agttctccaa gcgcgtgatc  3840
ctggccgatg ccaacctgga caaggtgctg agcgcctaca acaagcaccg ggataagccc  3900
atcagagagc aggccgagaa tatcatccac ctgtttaccc tgaccaacct gggagcccct  3960
gccgccttca agtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggcga ccccaagaaa aagcgcaaag tgtga                4125
```

-continued

```
SEQ ID NO: 5            moltype = DNA  length = 20
FEATURE                 Location/Qualifiers
source                  1..20
                        mol_type = other DNA
                        organism = synthetic construct
SEQUENCE: 5
aagtaaaacc tctacaaatg                                           20
```

MULTI-MOTIF DENDRONS AND THEIR SUPRAMOLECULAR STRUCTURES AND USES THEREOF

CROSS REFERENCE TO RELATED APPLICATIONS

This present application is a continuation of and claims priority to the International Patent Application No. PCT/CA2022/051745 filed Nov. 29, 2022 which claims the benefit of priority from U.S. Provisional Patent Application No. 63/398,936 filed Aug. 18, 2022, and U.S. Provisional Patent Application No. 63/283,588 filed Nov. 29, 2021. The entire contents of each of the foregoing is incorporated herein by reference in their entireties.

INCORPORATION BY REFERENCE OF SEQUENCE LISTING

The present application is being filed with a Sequence Listing in electronic format. The Sequence Listing is provided as a file entitled 2223-P65860PC00_SequenceListing.xml, created on Dec. 16, 2022, and is 11 kilobytes in size. The information in electronic format of the Sequence Listing is incorporated herein by reference in its entirety.

FIELD

The present application relates generally to the field of dendrons. In particular, it relates to dendron nanoparticles and compositions thereof. More particularly, it relates to dendron nanoparticle compositions for the delivery of agents such as nucleic acids and drugs.

BACKGROUND

Nucleic acids, such as deoxyribonucleic acid (DNA) and ribonucleic acid (RNA), including messenger ribonucleic acid (mRNA), small interfering RNA (siRNA), microRNA (miRNA) and long noncoding RNA (lncRNA), hold immense potential for the development of new therapeutics and vaccines. The delivery of nucleic acids to cells is a direct way to influence gene expression at the cellular level. For example, mRNA have shown therapeutic potential in a wide range of applications, including viral vaccines and genome editing [Pardi, N., Hogan, M. J., Porter, F. W. & Weissman, D., mRNA vaccines—a new era in accinology, *Nat. Rev. Drug Discov.* 17, 261-279, 2018; Barbier, A. J., Jiang, A. Y., Zhang, P., Wooster, R. & Anderson, D. G., The clinical progress of mRNA vaccines and immunotherapies, *Nat. Biotechnol.* 1-15, 2022]. In 2021, the first mRNA vaccines, Comirnaty (BNT162b) and Spikevax (mRNA-1273), were authorized to protect against COVID-19 [Corbett, K. S. et al., Evaluation of the mRNA-1273 Vaccine against SARS-CoV-2 in Nonhuman Primates, N. Engl. J. Med. 383, 1544-1555, 2020; Chaudhary, N., Weissman, D. & Whitehead, K. A., mRNA vaccines for infectious diseases: principles, delivery and clinical translation, *Nat. Rev. Drug Discov.* 20, 817-838, 2021]. However, current materials used to sequester and deliver nucleic acids have drawbacks both in terms of their manufacturing and biological effect. For instance, high molecular weight materials are difficult to synthesize and delivery materials are often toxic to the body and/or trigger an inflammatory immune response. Furthermore, simultaneous sequestration of different types of nucleic acids in a form conducive for delivery is not currently well developed. Taken together, these current limitations of delivery materials hamper the widespread use of nucleic acids.

Currently, lipid nanoparticles (LNPs), proteins, modified dendrimers and cationic nanoemulsions are used for the delivery of nucleic acids. LNPs for example, have been successfully used to deliver nucleic acids [A. J. Geall, A. Verma, G. R. Otten, et al., Proceedings of the National Academy of Sciences of the United States of America 2012, 109, 14604-14609; A. Hekele, S. Bertholet, J. Archer, et al., Emerging Microbes and Infections 2013, 2]. Typical LNPs contain four components: an ionizable lipid, a phospholipid, cholesterol, and lipid-conjugated polyethylene glycol (PEG). The ionizable lipid binds to nucleic acid during LNP formulation, and acts as the main driver of the nucleic acid expression and immunogenicity [Hassett, K. J. et al., Optimization of Lipid Nanoparticles for Intramuscular Administration of mRNA Vaccines, Mol. Ther. Nucleic Acids 15, 1-11, 2019; Han, X. et al., An ionizable lipid toolbox for RNA delivery, *Nat. Commun.* 12, 1-6, 2021]. These lipids are bi functional; one end contains a protonated tertiary amine that electrostatically associates with the anionic nucleic acid, and the other end has a lipid tail for nanoparticle self-assembly. However, these materials typically need an array of helper lipids, such as DSPC, to add charge for better nucleic acid sequestration, resulting in complex formulations that can lead to processing errors. Ionizable LNPs have a neutral charge at physiological pH to mitigate toxicity arising from permanently cationic particles, and after uptake by cells the ionizable lipids acquire a positive charge in acidic endosomes to facilitate the release of nucleic acid into the cytosol [Heyes, J., Palmer, L., Bremner, K. & MacLachlan, I., Cationic lipid saturation influences intracellular delivery of encapsulated nucleic acids, *J. Controlled Release* 107, 276-287, 2005; Semple, S. C. et al., Rational design of cationic lipids for siRNA delivery, *Nat. Biotechnol.* 28, 172-176, 2010; Heyes, J., Palmer, L., Bremner, K. & MacLachlan, I., Cationic lipid saturation influences intracellular delivery of encapsulated nucleic acids, *J. Controlled Release* 107, 276-287, 2005].

Ionizable lipids in the literature share a set of structural features, including: 1) one or more tertiary amines to bind RNA at low pH; 2) multiple alkyl tails for hydrophobic self-assembly, and 3) a general 'cone'-shape to disrupt endosomal membranes [Cullis, P. R., Hope, M. J. & Tilcock, C. P. S., Lipid polymorphism and the roles of lipids in membranes, *Chemistry and Physics of Lipids* 40, 127-144, 1986; Hafez, I. M., Maurer, N. & Cullis, P. R., On the mechanism whereby cationic lipids promote intracellular delivery of polynucleic acids, *Gene Ther.* 8, 1188-1196, 2001; Semple, S. C. et al., Rational design of cationic lipids for siRNA delivery, *Nat. Biotechnol.* 28, 172-176, 2010]. Since small modifications of the molecular structure can drastically change the efficacy of RNA delivery, careful and intentional design of the ionizable lipid structure is desirable.

Crosslinked protein particles have been used to contain and deliver nucleic acids; however, degradable cross-linkers are needed along with cationic lipids to enhance delivery and transfection [J. Xu, J. C. Luft, X. Yi, et al., Molecular Pharmaceutics 2013, 10, 3366-3374.], which also lead to overly complex formulations and multiple error-prone processing steps.

Modified dendrimers are larger molecular weight polymers that symmetrically branch from a central point in a starburst pattern [J. S. Chahal, O. F. Khan, C. L. Cooper, et al., Proc Natl Acad Sci USA 2016, 113, E4133-4142; O. F. Khan, E. W. Zaia, S. Jhunjhunwala, et al., Nano Lett 2015, 15, 3008-3016; O. F. Khan, E. W. Zaia, H. Yin, et al., Angewandte Chemie 2014, 53, 14397-14401]. Due to branching, they contain more amines for protonation and better nucleic acid binding. The perimeter of these symmetrically branched polymers incorporates non-polar alkanes for nanoparticle self-assembly. Though they sometimes do not require additional helper lipids to increase the amount of charge, there is considerable steric hindrance from the outer alkane groups that prevent close electrostatic association with the nucleic acid and incorporation of the dendrimers into a nanoparticle self-assembly. This steric hindrance can result in inefficient packing of the nucleic acid in the nanoparticle, where larger nucleic acids remain near or at the surface of the nanoparticle where they are exposed and unprotected. It may be possible to grow dendrimers asymmetrically, where two or more amines are located on the same side of the core; however, the presence of multiple amines on one side of the core rapidly causes crowding, increasing steric hindrance that blocks the formation of higher generation dendrimers. Furthermore, steric hindrance also blocks one from incorporating terminal alkanes into the asymmetric dendrimer. Still further, modified dendrimers are difficult to synthesize as a unimolecular species because reactions result in multiple degrees of substitutions that necessitate long and expensive purifications. These multiple degrees of substitution also result in a large number of isomers that can impact performance, safety and purity. The isomers include stereoisomers, positional isomers and chirality, all of which are difficult to predict, isolate and control. Moreover, modified dendrimers have higher molecular weights that can impact their ability to be cleared by the body. If dendrimers incorporate degradable groups, the degradation components from these higher molecular weight molecules are also large and remain difficult to clear from the body. Additionally, the higher number of amines in the dendrimer negatively impacts the ability to purify these materials using normal phase chromatographic separation processes, as the numerous amines interact with the stationary phase of the chromatography columns, causing delays in elution and multiple isomers to detrimentally co-elute without any separation. This separation problem creates great difficulty when trying to test the efficacy and safety of individual isomers. Dendrimers also contain a significant amount of void space between branches. Thus, when dendrimers are used to form nanoparticles, the nanoparticles contain a large amount of void space that cannot be filled with nucleic acid payloads; this wasted space reduces the overall efficiency of nucleic acid delivery. Moreover, dendrimers are known to be toxic; while terminal modifications can reduce toxicity, the toxicity caused by the large amount of charge per molecule remains a failing (see for e.g. Labieniec-Watala, M. and Watala, C. J. Pharm. Sci. 2015, 104(1):2-14 and Mendes, L. P. et al. Molecules, 2017, 22(9):1401).

Cationic nanoemulsions are nanoparticles formed with the MF59 adjuvant that have nucleic acids adsorbed to their surface [L. A. Brito, M. Chan, C. A. Shaw, et al., Molecular Therapy 2014, 22, 2118-2129; W. M. Bogers, H. Oostermeijer, P. Mooij, et al., Journal of Infectious Diseases 2015, 211, 947-955]; however, the (delivery material):(nucleic acid) mass ratio is an order of magnitude higher than lipid nanoparticle systems, which may lead to dose limiting material-induced effects.

Nanoparticle compositions for delivery of nucleic acids that comprise modified dendrimers are disclosed, for example, in PCT Patent Application Publication No. WO2020/132196.

Therefore, there is an unmet need for new delivery materials with low molecular weights, the ability to load high amounts of nucleic acids and other agents, reduce wasted internal void space, and the ability to contain multiple types of nucleic acids and/or other agents simultaneously.

SUMMARY

Given the aforementioned limitations, considerations for an optimal delivery system include following engineering design criteria: (1) Multiple ionizable charges, z, per delivery molecule; (2) Maximize electrostatic force, F, by minimizing the distance, L, between the delivery charge and nucleic acid according to the relationship $F \propto 1/L^2$; (3) Minimize the mass ratio of (delivery molecule):(nucleic acid) by maximizing the binding affinity, KD; (4) Optimized molecular packing of delivery materials through formulation conditions; and (5) Incorporate molecular groups that modulate cellular responses.

Based on these design criteria, a new class of dendron-inspired branched molecules that are the ideal delivery material (generally depicted by the illustration in FIG. 1) have been prepared. These delivery materials allow for the separation of charge and self-assembly groups, thus reducing steric hindrance and increasing nucleic acid accessibility. Flexible chemistries facilitate charge density, self-assembly and solubility optimizations. Importantly, the molecular structure is tunable to modulate cell responses, degradation, clearance, and other fundamental properties.

Therefore, the present application includes a dendron of Formula I, or a salt and/or solvate thereof:

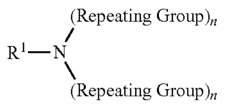

(I)

wherein:

each Repeating Group is the same or different and is:

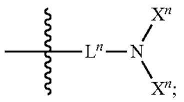

n is 1, 2, 3, 4 or 5 and each L and each $X^n$ are the same or different and are as defined below, depending on the value for n;

when n is 1, the dendron is a generation 1 dendron and the compound of Formula has the following structure:

$$R^1—N—(L^1—N(X^1)_2)_2,$$

wherein each $X^1$ is the same or different and is either H or a Terminal Group, provided at least one $X^1$ is a Terminal Group and each $L^1$ is the same or different and is a Linking Group;

when n is 2, the dendron is a generation 2 dendron and the compound of Formula has the following structure:

$$R^1—N—(L^1—N—(L^2—N(X^2)_2)_2)_2,$$

wherein each $X^2$ is the same or different and is either H or a Terminal Group, provided at least one $X^2$ is a Terminal Group and each $L^1$ and each $L^2$ is the same or different and is a Linking Group;

when n is 3, the dendron is a generation 3 dendron and the compound of Formula has the following structure:

$$R^1—N—(L^1—N—(L^2—N—(L^3—N(X^3)_2)_2)_2)_2$$

wherein each $X^3$ is the same or different and is either H or a Terminal Group, provided at least one $X^3$ is a Terminal Group and each $L^1$, each $L^2$ and each $L^3$ is the same or different and is a Linking Group;

when n is 4, the dendron is a generation 4 dendron and the compound of Formula has the following structure:

$$R^1—N—(L^1—N—(L^2—N—(L^3—N—(L^4—N(X^4)_2)_2)_2)_2)_2$$

wherein each $X^4$ is the same or different and is either H or a Terminal Group, provided at least one $X^4$ is a Terminal Group and each $L^1$, each $L^2$, each $L^3$ and each $L^4$ is the same or different and is a Linking Group;

when n is 5, the dendron is a generation 5 dendron and the compound of Formula has the following structure:

$$R^1—N—(L^1—N—(L^2—N—(L^3—N—(L^4—N—(L^5—N(X^5)_2)_2)_2)_2)_2)_2$$

wherein each $X^5$ is the same or different and is either H or a Terminal Group, provided at least one $X^5$ is a Terminal Group and each $L^1$, each $L^2$, each $L^3$ each $L^4$ and each $L^5$ is the same or different and is a Linking Group;

$R^1$ is selected from $C_{1-20}$alkyl, $C_{2-20}$alkenyl, $C_{2-20}$alkynyl, $C_{1-20}$alkylenearyl, $C_{1-20}$alkyleneheteroaryl, $C_{1-20}$alkylene$C_{3-8}$heterocycloalkyl, $C_{1-20}$alkylene $C_{3-8}$cycloalkyl and $C_{1-6}$alkylene-S—S—$C_{1-6}$alkyl, each of which is unsubstituted or substituted with one or more of halo, OH, $OC_{1-20}$alkyl, $C(O)OC_{1-20}$alkyl and $NR^2R^{2'}$, and the aryl, heteroaryl, heterocycloalkyl and cycloalkyl groups are additionally optionally substituted with one or more of $C_{1-10}$alkyl;

$R^1$ and $R^{2'}$ are independently selected from H and $C_{1-10}$alkyl;

the Linker Group comprises $C_{1-20}$ alkylene or $C_{2-20}$ alkenylene, each of which is optionally interrupted by one or more groups selected from S, S—S, O, NH, $N(C_{1-4}alkyl)$, C(O), C(O)O, OC(O), C(O)NH, NHC(O), NHC(NH), $NHC(NC_{1-4}alkyl)$, C(NH)NH and $C(NC_{1-4}alkyl)NH$, and each alkyl, alkylene and alkenylene is unsubstituted or substituted with one or more of halo and OH;

the Terminal Group is selected from $C_{1-40}$alkyl, $C_{2-40}$alkenyl, $C_{1-40}$alkylenearyl and $C_{1-40}$alkenylenearyl, each alkyl, alkenyl, alkylene and alkenylene being optionally interrupted by one or more groups selected from S—S, C(O), OC(O), C(O)O, OC(O)O, $NR^3C(O)O$, $OC(O)NR^3$, C(O)S, SC(O), $NR^3C(O)$, $C(O)NR^3$, $NR^3C(O)NR^4$ and $C(NC_{1-20}alkyl)$, and the alkyl, alkenyl, alkylenearyl and alkenylenearyl are optionally substituted with one or more of halo, $NR^5R^{5'}$ and OH; and $R^3$, $R^4$, $R^5$ and $R^{5'}$ are independently hydrogen or $C_{1-10}$alkyl;

wherein all available hydrogen atoms bonded to carbon are optionally replaced with a fluorine atom.

Also included in the present application is a nanoparticle comprising one or more dendrons of the application, a colloid comprising one or more dendrons of the application or a supramolecular structure comprising one or more dendrons of the application. In some embodiments, the nanoparticle is a lipid nanoparticle (LNP).

The present application also includes a composition comprising one or more dendrons of the application, as well as one or more nanoparticles, one or more colloids and/or one or more supramolecular structures, each comprising one or more dendrons of the application.

In some embodiments, the compositions of the application further comprise one or more agents to be delivered to a cell or subject.

In some embodiments, the compositions of the application comprise one or more dendrons of the application, one or more PEG-lipids, one or more phospholipids, one or more steroids and one or more agents to be delivered.

Also included in the present application is a method of delivering one or more agents to a cell or subject comprising contacting the cell or subject with one or more compositions of the application, wherein the cell or subject is to be contacted under conditions to cause uptake of the agent into the cell or subject.

The present application also includes a kit comprising one or more dendrons of the application or one or more compositions of the application.

BRIEF DESCRIPTION OF THE DRAWING

Certain embodiments of the application will now be described in greater detail with reference to the attached drawings in which.

DETAILED DESCRIPTION

Definitions

Figure 1:
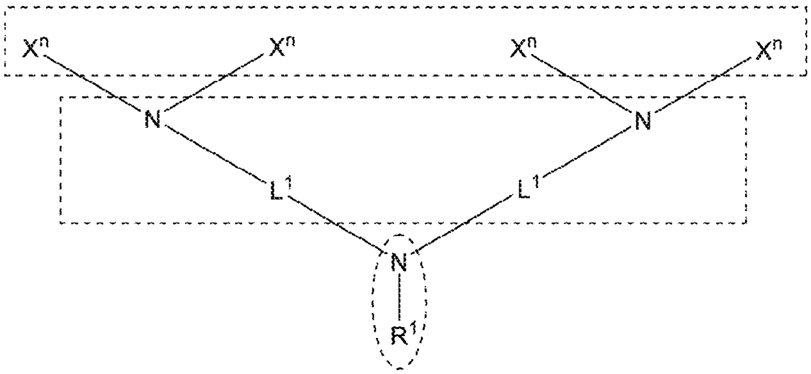
FIG. 1 shows a general schematic of exemplary dendrons of the application, wherein each $L^1$ is a linker group that can be the same or different, each X″ is H, a Terminal Group or further repeating L″N(X″)$_2$ groups that can be the same or different and n is the generation number, for example 1, 2, 3, 4, or 5. The top hatched box represents the self-assembly and degradable region of the dendron, the next hatched box represents the ionizable charge region of the dendron which is for binding agents such as nucleic acids, and the bottom hatched oval is the Focal Group.

Unless otherwise indicated, the definitions and embodiments described in this and other sections are intended to be applicable to all embodiments and aspects of the present application herein described for which they are suitable as would be understood by a person skilled in the art.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component or effect, such as an additional or second compound, the second compound as used herein is different from the other compounds or first compound. A "third" compound is different from the other, first, and second compounds, and further enumerated or "additional" compounds are similarly different.

When "one or more" molecules or materials are referenced (such as one or more dendrons), it is understood that this is in reference to the "type" or "identity" of the molecule or material. Therefore, a "second" molecule or material is different from the one, or first, molecule or material. Similarly, a "third" molecule or material is different from the one, first, and second molecules or materials, and further enumerated or "additional" molecules or materials are similarly different.

The term "and/or" as used herein means that the listed items are present, or used, individually or in combination. In effect, this term means that "at least one of" or "one or more" of the listed items is used or present. For example, the term "and/or" with respect to salts and/or solvates thereof means that the compounds of the application exist as individual salts and hydrates, as well as a combination of, for example, a salt of a solvate of a compound of the application.

The term "dendron of the application" or "dendron of the present application" and the like as used herein refers to a dendron of Formula I and salts and/or solvates thereof.

The term "composition of the application" or "composition of the present application" and the like as used herein refers to a composition comprising one or more dendrons of the application.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

The present description refers to a number of chemical terms and abbreviations used by those skilled in the art. Nevertheless, definitions of selected terms are provided for clarity and consistency.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas).

The term "inert organic solvent" as used herein refers to a solvent that is generally considered as non-reactive with the functional groups that are present in the compounds to be combined together in any given reaction so that it does not interfere with or inhibit the desired synthetic transformation. Organic solvents are typically non-polar and dissolve compounds that are non soluble in aqueous solutions.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms. All alkyl groups are optionally fluoro-substituted unless otherwise indicated.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{1-6}$alkylene means an alkylene group having 1, 2, 3, 4, 5 or 6 carbon atoms. All alkylene groups are optionally fluoro-substituted unless otherwise indicated.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond. All alkenyl groups are optionally fluoro-substituted unless otherwise indicated.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms.

The term "aryl" as used herein, whether it is used alone or as part of another group, refers to a monovalent unsaturated aromatic group wherein the ring atoms are all carbon. Aryl groups can comprise 6 or more carbon atoms. All aryl groups are optionally fluoro-substituted unless otherwise indicated.

The term "cycloalkyl," as used herein, whether it is used alone or as part of another group, means a saturated carbocyclic group containing one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms. All cycloalkyl groups are optionally fluoro-substituted unless otherwise indicated.

The term "heteroaryl" as used herein, whether it is used alone or as part of another group, refers to cyclic groups containing at least one heteroaromatic ring in which one or more of the atoms are a heteroatom selected from O, S and N. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. All heteroaryl groups are optionally fluoro-substituted unless otherwise indicated.

The term "heterocycloalkyl" as used herein, whether it is used alone or as part of another group, refers to cyclic groups containing at least one non-aromatic ring in which one or more of the atoms are a heteroatom selected from O, S and N. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as defined above. All heterocycloalkyl groups are optionally fluoro-substituted unless otherwise indicated.

The term “fluoro-substituted” refers to the substitution of one or more, including all, available hydrogens in a referenced group with fluoro.

The terms “halo” or “halogen” as used herein, whether it is used alone or as part of another group, refers to a halogen atom and includes fluoro, chloro, bromo and iodo.

The symbol “⁓” when drawn perpendicularly across a bond indicates a point of attachment of the group The term “available”, as in “available hydrogen atoms” or “available atoms” refers to atoms that would be known to a person skilled in the art to be capable of replacement by a substituent, such as a fluorine atom.

It is to be clear that all available hydrogen atoms in the compounds of the application, and all embodiments thereof, are optionally substituted with a fluorine atom unless otherwise indicated.

The term “cell” as used herein refers to a single cell or a plurality of cells and includes a cell either in a cell culture or in a subject.

The term “subject” as used herein refers to any target for delivery of one or more agents using compositions of the application. A subject may be a live subject including all members of the animal and plant kingdoms, or an inanimate object. Thus, the methods and uses of the present application are applicable to human therapy, veterinary therapy, plant applications and material treatment.

The term “pharmaceutically acceptable” means compatible with the treatment of subjects, for example humans.

The term “pharmaceutically acceptable carrier” means a non-toxic solvent, dispersant, excipient, adjuvant or other material which is mixed with the active ingredient in order to permit the formation of a pharmaceutical composition, i.e., a dosage form capable of administration to a subject.

The term “pharmaceutically acceptable salt” means either an acid addition salt or a base addition salt which is suitable for, or compatible with the treatment of subjects.

The term “solvate” as used herein means a compound, or a salt and/or prodrug of a compound, wherein molecules of a suitable solvent are incorporated in the crystal lattice. A suitable solvent is physiologically tolerable at the dosage administered.

The term “treating” or “treatment” as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. “Treating” and “treatment” can also mean prolonging survival as compared to expected survival if not receiving treatment. “Treating” and “treatment” as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds or compositions of the application and optionally consist of a single administration, or alternatively comprise a series of administrations.

“Palliating” a disease or disorder means that the extent and/or undesirable clinical manifestations of a disorder or a disease state are lessened and/or time course of the progression is slowed or lengthened, as compared to not treating the disorder.

The term “prevention” or “prophylaxis”, or synonym thereto, as used herein refers to a reduction in the risk or probability of a patient becoming afflicted with a disease, disorder or condition.

As used herein, the term “effective amount” or “therapeutically effective amount” means an amount of a compound or one or more compounds of the application, or a composition or one or more compositions of the application, that is effective, at dosages and for periods of time necessary to achieve the desired result.

By “inhibiting, blocking and/or disrupting” it is meant any detectable inhibition, block and/or disruption in the presence of a compound or composition compared to otherwise the same conditions, except for in the absence in the compound or composition.

The term “administered” as used herein means administration of a therapeutically effective amount of a compound or one or more compounds of the application, or a composition or one or more compositions of the application, to a cell, a tissue or an organ either in vivo, in vitro or ex vivo.

The term “encapsulation efficiency” refers to the fraction of an agent to be encapsulated in a particle, such as a nanoparticle, that is confined inside nanoparticles.

As used herein, the term “nanoparticle”, “nanoparticles” or variants thereof is intended to mean particles whose size is measured on a nanometer scale.

The term “colloid” as used herein refers to a mixture in which microscopically dispersed insoluble particles are suspended throughout another substance, typically a liquid.

The term “supramolecular structure” as used herein refers to a complex of molecules held together by non-covalent bonds.

Dendrons and Compositions of the Application

Multi-amine structures, such as poly(amidoamine) (PAMAM) dendrons are biocompatible materials comprising a core amine group that branches out unidirectionally into successive generations containing repeated amine and amide units. Multi-amine structures, such as poly(amidoamine) PAMAM dendrons may be chemically modified to alter or improve functionality.

A wide variety of structural modifications to basic multi-amine structures, such as poly(amidoamine) PAMAM dendrons are possible. These modifications aim to improve efficacy and reduce toxicity of multi-amine structures, such as poly(amidoamine) PAMAM dendrons. Modified dendrons that contain nitrogens are multi-functional, with separate structural motifs fulfilling different roles to effectively deliver nucleic acids and other agents suitably with an overall negative charge. For example, nitrogen-containing tertiary amines within the structure are protonated at low pH and become cationic. These ionizable cations interact with, for example, the negative charges along the sugar-phosphate backbone of nucleic acids and allow the delivery material to bind to its cargo, self-assembling into nanoparticles. Amides enhance biodegradability and reduce toxicity of the delivery material. Hydrophobic tails promote self-assembly of the delivery material once it has bound a nucleic acid. Disulfides, esters, thioesters, carbamates, ureas, imines, enamines, ketones or other hydrolyzable groups may optionally be included to control release of nucleic acid cargo and improve biodegradability. Including unsaturated, fluorinated, sterically hindered, or inflexible groups alter self-assembly and packing within each nanoparticle.

Therefore, the present application includes a dendron of Formula I, or a salt and/or solvate thereof:

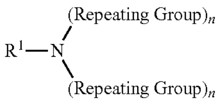

(I)

wherein:

each Repeating Group is the same or different and is:

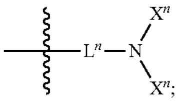

n is 1, 2, 3, 4 or 5 and each $L^n$ and each $X^n$ are the same or different and are as defined below, depending on the value for n;

when n is 1, the dendron is a generation 1 dendron and the compound of Formula I has the following structure:

$$R^1—N—(L^1—N(X^1)_2)_2,$$

wherein each $X^1$ is the same or different and is either H or a Terminal Group, provided at least one $X^1$ is a Terminal Group and each $L^1$ is the same or different and is a Linking Group;

when n is 2, the dendron is a generation 2 dendron and the compound of Formula I has the following structure:

$$R^1—N—(L^1—N—(L^2—N(X^2)_2)_2)_2,$$

wherein each $X^2$ is the same or different and is either H or a Terminal Group, provided at least one $X^2$ is a Terminal Group and each $L^1$ and each $L^2$ is the same or different and is a Linking Group;

when n is 3, the dendron is a generation 3 dendron and the compound of Formula I has the following structure:

$$R^1—N—(L^1—N—(L^2—N—(L^3—N(X^3)_2)_2)_2)_2,$$

wherein each $X^3$ is the same or different and is either H or a Terminal Group, provided at least one $X^3$ is a Terminal Group and each $L^1$, each $L^2$ and each $L^3$ is the same or different and is a Linking Group;

when n is 4, the dendron is a generation 4 dendron and the compound of Formula I has the following structure:

$$R^1—N—(L^1—N—(L^2—N—(L^3—N—(L^4—N(X^4)_2)_2)_2)_2)_2,$$

wherein each $X^4$ is the same or different and is either H or a Terminal Group, provided at least one $X^4$ is a Terminal Group and each $L^1$, each $L^2$, each $L^3$ and each $L^4$ is the same or different and is a Linking Group;

when n is 5, the dendron is a generation 5 dendron and the compound of Formula I has the following structure:

$$R^1—N—(L^1—N—(L^2—N—(L^3—N—(L^4—N—(L^5—N(X^5)_2)_2)_2)_2)_2)_2$$

wherein each $X^5$ is the same or different and is either H or a Terminal Group, provided at least one $X^5$ is a Terminal Group and each $L^1$, each $L^2$, each $L^3$ each $L^4$ and each $L^5$ is the same or different and is a Linking Group;

$R^1$ is selected from $C_{1-20}$alkyl, $C_{2-20}$alkenyl, $C_{2-20}$alkynyl, $C_{1-20}$alkylenearyl, $C_{1-20}$alkyleneheteroaryl, $C_{1-20}$alkylene$C_{3-8}$heterocycloalkyl, $C_{1-20}$alkylene $C_{3-8}$cycloalkyl and $C_{1-6}$alkylene-S—S—$C_{1-6}$alkyl, each of which is unsubstituted or substituted with one or more of halo, OH, $OC_{1-20}$alkyl, $C(O)OC_{1-20}$alkyl and $NR^2R^{2'}$, and the aryl, heteroaryl, heterocycloalkyl and cycloalkyl groups are additionally optionally substituted with one or more of $C_{1-10}$alkyl;

$R^2$ and $R^{2'}$ are independently selected from H and $C_{1-10}$alkyl;

the Linker Group comprises $C_{1-20}$ alkylene or $C_{2-20}$ alkenylene, each of which is optionally interrupted by one or more groups selected from S, S—S, O, NH, $N(C_{1-4}$alkyl), C(O), C(O)O, OC(O), C(O)NH, NHC(O), NHC(NH), $NHC(NC_{1-4}$alkyl), C(NH)NH and $C(NC_{1-4}$alkyl)NH, and each alkyl, alkylene and alkenylene is unsubstituted or substituted with one or more of halo and OH;

the Terminal Group is selected from $C_{1-40}$alkyl, $C_{2-40}$alkenyl, $C_{1-40}$alkylenearyl and $C_{1-40}$alkenylenearyl, each alkyl, alkenyl, alkylene and alkenylene being optionally interrupted by one or more groups selected from S—S, C(O), OC(O), C(O)O, OC(O)O, $NR^3C(O)O$, $OC(O)NR^3$, C(O)S, SC(O), $NR^3C(O)$, $C(O)NR^3$, $NR^3C(O)NR^4$ and $C(NC_{1-20}$alkyl), and the alkyl, alkenyl, alkylenearyl and alkenylenearyl are optionally substituted with one or more of halo, $NR^5R^{5'}$ and OH; and $R^3$, $R^4$, $R^5$ and $R^{5'}$ are independently hydrogen or $C_{1-10}$alkyl;

wherein all available hydrogen atoms bonded to carbon are optionally replaced with a fluorine atom.

In some embodiments, $R^1$ is selected from $C_{1-10}$alkyl, $C_{2-10}$alkenyl, $C_{2-10}$alkynyl, $C_{1-10}$alkylenePh, $C_{1-10}$alkyleneheteroaryl, $C_{1-10}$alkylene$C_{5-6}$heterocycloalkyl, $C_{1-10}$alkylene$C_{5-6}$cycloalkyl and $C_{1-4}$alkylene-S—S—$C_{1-4}$alkyl, each of which is unsubstituted or substituted with one to four of OH, $OC_{1-15}$alkyl, $C(O)OC_{1-15}$alkyl and $NR^2R^{2'}$ and/or one or more fluoro, the phenyl, heteroaryl, heterocycloalkyl and cycloalkyl groups are additionally optionally substituted with one to four of $C_{1-4}$alkyl and $C_{1-4}$fluoroalkyl, and $R^2$ and $R^{2'}$ are independently selected from H and $C_{1-4}$alkyl.

In some embodiments, $R^1$ is selected from $C_{1-6}$alkyl, $C_{2-6}$alkenyl, $C_{2-6}$alkynyl, $C_{1-6}$alkylenePh, $C_{1-6}$alkylene$C_6$heterocycloalkyl and $C_{1-4}$alkylene-S—S—$C_{1-4}$alkyl, each of which is unsubstituted or substituted with one or two of OH, $OC_{1-12}$alkyl, $C(O)OC_{1-15}$alkyl and $NR^2R^{2'}$, and/or one or more fluoro, the phenyl and heterocycloalkyl groups are additionally optionally substituted with one or two $C_{1-4}$alkyl and $C_{1-4}$fluoroalkyl, and $R^2$ and $R^{2'}$ are independently selected from H and $C_{1-4}$alkyl. In some embodiments, $R^1$ is selected from $C_{1-6}$alkyl, $C_{2-6}$alkenyl and $C_{1-6}$fluoroalkyl.

In some embodiments, $R^1$ is selected from:

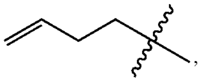
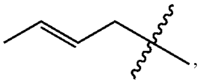
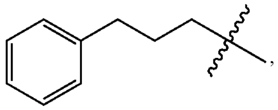
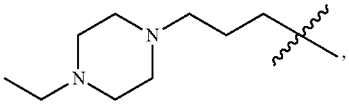
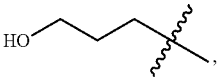
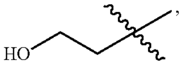

$C_3F_7$, $C_5H_{11}$, $C_6H_{13}$,

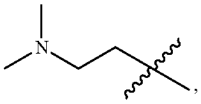
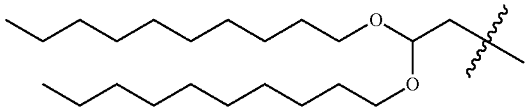
and
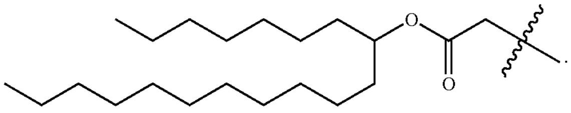

In some embodiments n is 1 or 2.

In some embodiments, $L^1$, $L^2$, $L^3$, $L^4$ and $L^5$ are independently a linker group comprising $C_{1-10}$alkylene or $C_{2-10}$alkenylene, each of which is optionally interrupted by one or two moieties independently selected from S, S—S, O, NH, N($C_{1-2}$alkyl), C(O), C(O)O, OC(O), C(O)NH, NHC(O), NHC(NH), NHC(N$C_{1-2}$alkyl), C(NH)NH, C(N$C_{1-2}$alkyl) NH, and each alkyl, alkylene and alkenylene is unsubstituted or substituted with one or two OH and/or one or more fluoro. In some embodiments, $L^1$, $L^2$, $L^3$, $L^4$ and $L^5$ are independently a linker group comprising $C_{1-10}$alkylene or $C_{2-10}$alkenylene, each of which is optionally interrupted by one or two moieties independently selected from S, S—S, O, C(O)O, OC(O), C(O)NH, NHC(O), and each alkylene and alkenylene is unsubstituted or substituted with one or two OH and/or one or more fluoro.

In some embodiments, $L^1$, $L^2$, $L^3$, $L^4$ and $L^5$ are independently a linker group comprising $C_{1-6}$alkylene or $C_{2-6}$alkenyene, each of which is optionally interrupted by one or two moieties independently selected from S—S, C(O)NH and NHC(O), and each alkylene and alkenylene is unsubstituted or substituted with one or two OH and/or one or more fluoro.

In some embodiments, $L^1$, $L^2$, $L^3$, $L^4$ and $L^5$ are independently selected from:

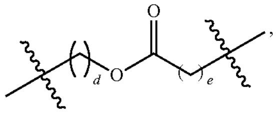
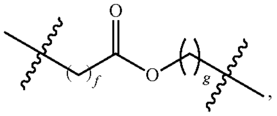
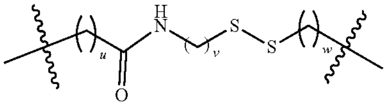
and
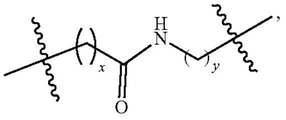

wherein d, e, f, g, u, v, w, x and y are independently selected from 1, 2, 3, 4, 5, and 6. In some embodiments, d, e, f, g, u, v, w, x and y are independently selected from 1 and 2.

In some embodiments, $L^1$, $L^2$, $L^3$, $L^4$ and $L^5$ are independently selected from:

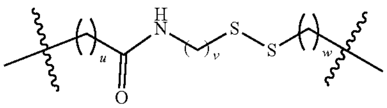
and
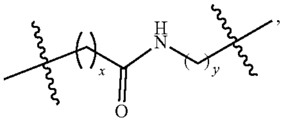

wherein u, v, w, x and y are independently selected from 1, 2, 3, 4, 5, and 6. In some embodiments, u, v, w, x and y are independently selected from 1 and 2.

In some embodiments, each $L^1$ in the generation 1 dendron is the same. In some embodiments, each $L^2$ in the generation 2 dendron is the same. In some embodiments, each $L^3$ in the generation 3 dendron is the same. In some embodiments, each $L^4$ in the generation 4 dendron is the same. In some embodiments, each $L^5$ in the generation 5 dendron is the same.

In some embodiments, the Terminal Group is selected from $C_{1-20}$alkyl, $C_{2-20}$alkenyl, $C_{1-20}$alkylenearyl and $C_{1-20}$alkenylenearyl, each alkyl, alkenyl, alkylene and alkenylene being optionally interrupted by one or more groups selected from S—S, C(O), OC(O), C(O)O, OC(O)O, $NR^3C$(O)O, OC(O)$NR^3$, C(O)S, SC(O), $NR^3$C(O), C(O)$NR^3$, $NR^3$C(O)$NR^4$ and C(N$C_{1-10}$alkyl); and the alkyl, alkenyl, alkylenearyl and alkenylenearyl are optionally substituted with one to four of OH and $NR^5R^{5'}$;

$R^3$, $R^4$, $R^5$ and $R^{5'}$ are independently hydrogen or $C_{1-10}$alkyl;

wherein all available hydrogen atoms bonded to carbon are optionally replaced with a fluorine atom.

In some embodiments the Terminal Group is selected from:

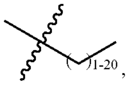
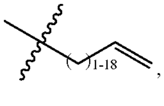
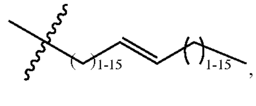

-continued

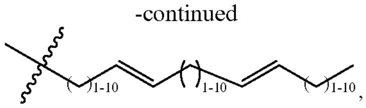,

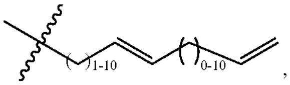, 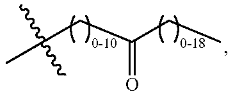,

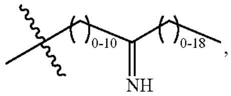, 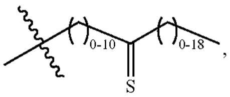,

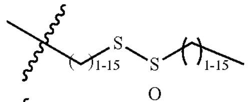,

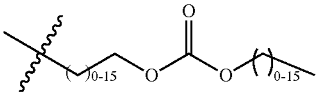,

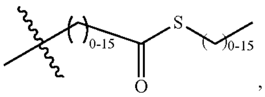, 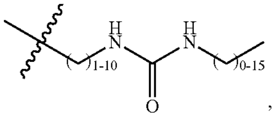,

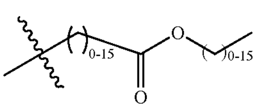, 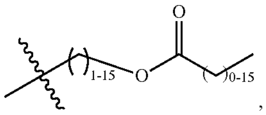,

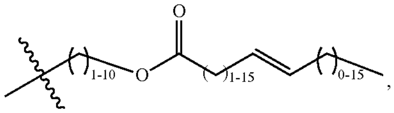,

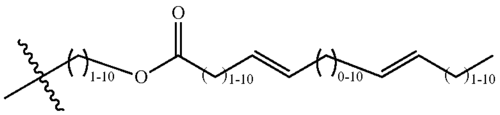 and

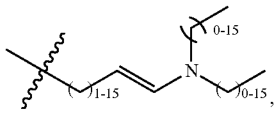, each of which is optionally substituted with one or two OH, one or two $NH_2$ and/or one or more fluorine, provided that the total number of carbon atoms in the group is 20 or less. In some embodiments, the Terminal Group is selected from:

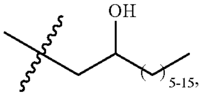, 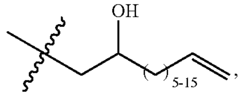,

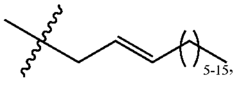, 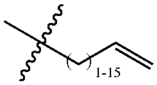,

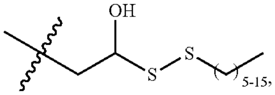, 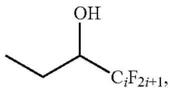,

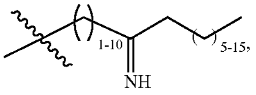 and 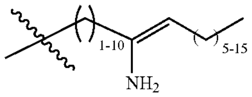

wherein i is and integer from 1 to 10.

In some embodiments, each $X^1$ in the generation 1 dendron is a Terminal Group and is the same or different. In some embodiments, each $X^1$ in the generation 1 dendron is a Terminal Group and is the same.

In some embodiments, at least two of $X^2$ in the generation 2 dendron are a Terminal Group and are the same or different. In some embodiments, at least three of $X^2$ in the generation 2 dendron are a Terminal Group and are the same or different. In some embodiments, all of $X^2$ in the generation 2 dendron are a Terminal Group and are the same or different. In some embodiments, at least one $X^2$ on each nitrogen in the generation 2 dendron is a Terminal Group and each Terminal Group is the same or different. In some embodiments, at least one $X^2$ on each nitrogen in the generation 2 dendron is a Terminal Group and each Terminal Group is the same. In some embodiments, all of $X^2$ in the generation 2 dendron are a Terminal Group and are the same.

In some embodiments, at least two of $X^3$ in the generation 3 dendron are a Terminal Group and are the same or different. In some embodiments, at least three of $X^3$ in the generation 3 dendron are a Terminal Group and are the same or different. In some embodiments, at least four of $X^3$ in the generation 3 dendron are a Terminal Group and are the same or different. In some embodiments, at least five of $X^3$ in the generation 3 dendron are a Terminal Group and are the same or different. In some embodiments, at least six of $X^3$ in the generation 3 dendron are a Terminal Group and are the same or different. In some embodiments, at least seven of $X^3$ in the generation 3 dendron are a Terminal Group and are the same or different. In some embodiments, all of $X^3$ in the generation 3 dendron are a Terminal Group and are the same or different. In some embodiments, at least one $X^3$ on each nitrogen in the generation 3 dendron is a Terminal Group and each Terminal Group is the same or different. In some embodiments, at least one $X^3$ on each nitrogen in the generation 3 dendron is a Terminal Group and each Terminal Group is the same. In some embodiments, all of $X^3$ in the generation 3 dendron are a Terminal Group and are the same.

In some embodiments, at least two of $X^4$ in the generation 4 dendron are a Terminal Group and are the same or different. In some embodiments, at least three of $X^4$ in the generation 4 dendron are a Terminal Group and are the same or different. In some embodiments, at least four of $X^4$ in the generation 4 dendron are a Terminal Group and are the same or different. In some embodiments, at least five of $X^4$ in the generation 4 dendron are a Terminal Group and are the same or different. In some embodiments, at least six of $X^4$ in the generation 4 dendron are a Terminal Group and are the same or different. In some embodiments, at least seven of $X^4$ in the generation 4 dendron are a Terminal Group and are the same or different. In some embodiments, at least eight of $X^4$ in the generation 4 dendron are a Terminal Group and are the same or different. In some embodiments, at least nine of $X^4$ in the generation 4 dendron are a Terminal Group and are the same or different. In some embodiments, at least ten of $X^4$ in the generation 4 dendron are a Terminal Group and are the same or different. In some embodiments, at least eleven of $X^4$ in the generation 4 dendron are a Terminal Group and are the same or different. In some embodiments, at least twelve of $X^4$ in the generation 4 dendron are a Terminal Group and are the same or different. In some embodiments, at least thirteen of $X^4$ in the generation 4 dendron are a Terminal Group and are the same or different. In some embodiments, at least fourteen of $X^4$ in the generation 4 dendron are a Terminal Group and are the same or different. In some embodiments, at least fifteen of $X^4$ in the generation 4 dendron are a Terminal Group and are the same or different. In some embodiments, all of $X^4$ in the generation 4 dendron are a Terminal Group and are the same or different. In some embodiments, at least one $X^4$ on each nitrogen in the generation 4 dendron is a Terminal Group and each Terminal Group is the same or different. In some embodiments, at least one $X^4$ on each nitrogen in the generation 4 dendron is a Terminal Group and each Terminal Group is the same. In some embodiments, all of $X^4$ in the generation 4 dendron are a Terminal Group and are the same.

In some embodiments, at least 2 of $X^5$ in the generation 5 dendron are a Terminal Group and are the same or different. In some embodiments, at least 3 of $X^5$ in the generation 5 dendron are a Terminal Group and are the same or different. In some embodiments, at least 4 of $X^4$ in the generation 5 dendron are a Terminal Group and are the same or different. In some embodiments, at least 5 of $X^5$ in the generation 5 dendron are a Terminal Group and are the same or different. In some embodiments, at least 6 of $X^5$ in the generation 5 dendron are a Terminal Group and are the same or different. In some embodiments, at least 7 of $X^5$ in the generation 5 dendron are a Terminal Group and are the same or different. In some embodiments, at least 8 of $X^5$ in the generation 5 dendron are a Terminal Group and are the same or different. In some embodiments, at least 9 of $X^5$ in the generation 5 dendron are a Terminal Group and are the same or different. In some embodiments, at least 10 of $X^5$ in the generation 5 dendron are a Terminal Group and are the same or different. In some embodiments, at least 11 of $X^5$ in the generation 5 dendron are a Terminal Group and are the same or different. In some embodiments, at least 12 of $X^5$ in the generation 5 dendron are a Terminal Group and are the same or different. In some embodiments, at least 13 of $X^5$ in the generation 5 dendron are a Terminal Group and are the same or different. In some embodiments, at least 14 of $X^5$ in the generation 5 dendron are a Terminal Group and are the same or different. In some embodiments, at least 15 of $X^5$ in the generation 5 dendron are a Terminal Group and are the same or different. In some embodiments, at least 16 of $X^5$ in the generation 5 dendron are a Terminal Group and are the same or different. In some embodiments, at least 17 of $X^5$ in the generation 5 dendron are a Terminal Group and are the same or different. In some embodiments, at least 18 of $X^5$ in the generation 5 dendron are a Terminal Group and are the same or different. In some embodiments, at least 19 of $X^5$ in the generation 5 dendron are a Terminal Group and are the same or different. In some embodiments, at least 20 of $X^5$ in the generation 5 dendron are a Terminal Group and are the same or different. In some embodiments, at least 21 of $X^5$ in the generation 5 dendron are a Terminal Group and are the same or different. In some embodiments, at least 22 of $X^5$ in the generation 5 dendron are a Terminal Group and are the same or different. In some embodiments, at least 23 of $X^5$ in the generation 5 dendron are a Terminal Group and are the same or different. In some embodiments, at least 24 of $X^5$ in the generation 5 dendron are a Terminal Group and are the same or different. In some embodiments, at least 25 of $X^5$ in the generation 5 dendron are a Terminal Group and are the same or different. In some embodiments, at least 26 of $X^5$ in the generation 5 dendron are a Terminal Group and are the same or different. In some embodiments, at least 27 of $X^5$ in the generation 5 dendron are a Terminal Group and are the same or different. In some embodiments, at least 28 of $X^5$ in the generation 5 dendron are a Terminal Group and are the same or different. In some embodiments, at least 29 of $X^5$ in the generation 5 dendron are a Terminal Group and are the same or different. In some embodiments, at least 30 of $X^5$ in the generation 5 dendron are a Terminal Group and are the same or different. In some embodiments, at least 31 of $X^5$ in the generation 5 dendron are a Terminal Group and are the same or different. In some embodiments, at least 32 of $X^5$ in the generation 5 dendron are a Terminal Group and are the same or different. In some embodiments, at least 33 of $X^5$ in the generation 5 dendron are a Terminal Group and are the same or different. In some embodiments, at least 34 of $X^5$ in the generation 5 dendron are a Terminal Group and are the same or different. In some embodiments, at least 35 of $X^5$ in the generation 5 dendron are a Terminal Group and are the same or different. In some embodiments, all of $X^5$ in the generation 5 dendron are a Terminal Group and are the same or different. In some embodiments, at least one $X^5$ on each nitrogen in the generation 5 dendron is a Terminal Group and each Terminal Group is the same or different. In some embodiments, at least one $X^5$ on each nitrogen in the generation 5 dendron is a Terminal Group and each Terminal Group is the same. In some embodiments, all of $X^5$ in the generation 5 dendron are a Terminal Group and are the same.

In some embodiments, the dendron of Formula I is selected from

I-1

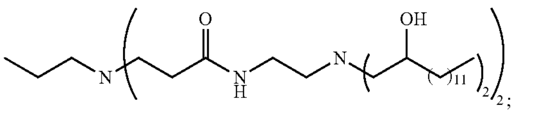

(G1-nPr-C14E)

I-2

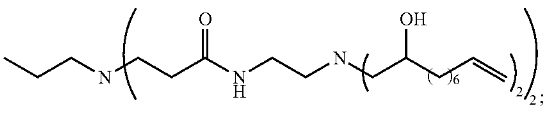

(G1-nPr-C10O1E)

I-3

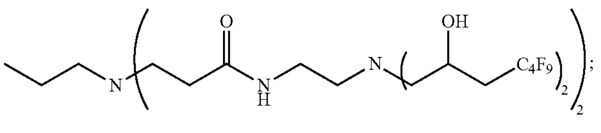

(G1-nPr-C7RfE)

I-4

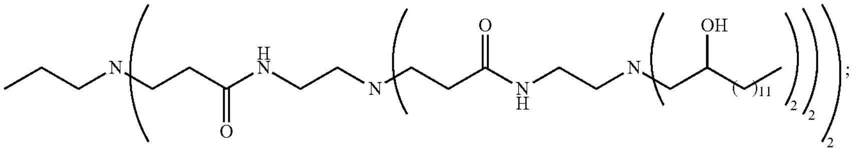

(G2-nPr-C14E)

-continued
I-5
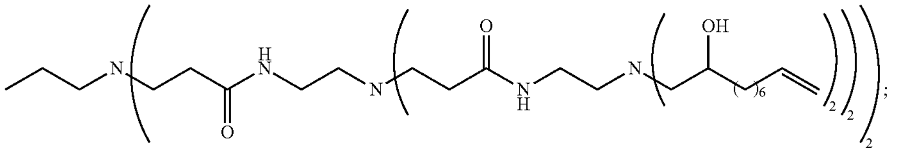
(G2-nPr-C10O1E)
I-6
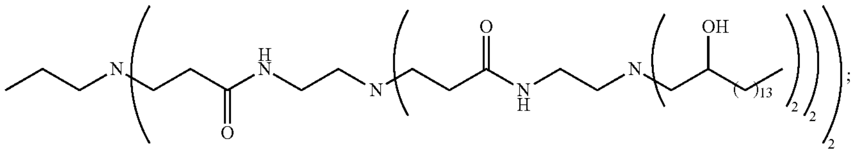
(G2-nPr-C16E)
I-7
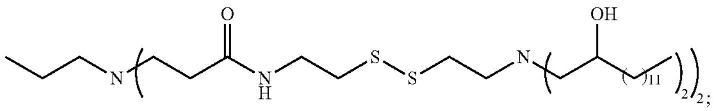
(G1-nPr-S8-C14E)
I-8
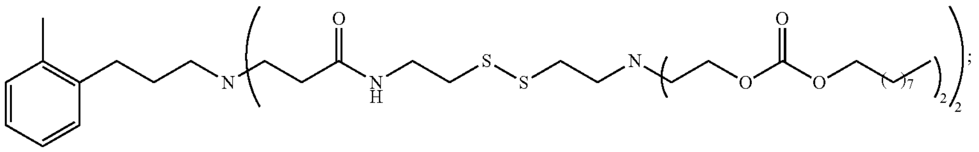
(G1-benzyl-S-1)
I-9
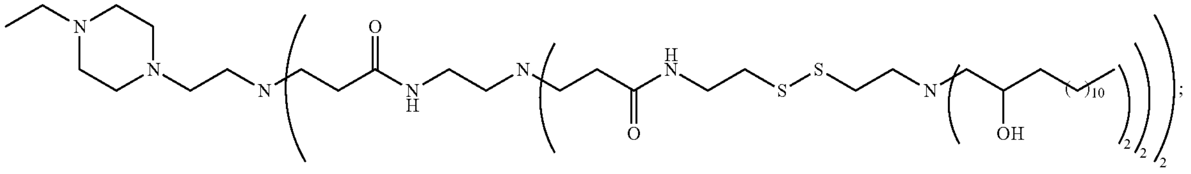
(G2-azine-S-1)
I-10
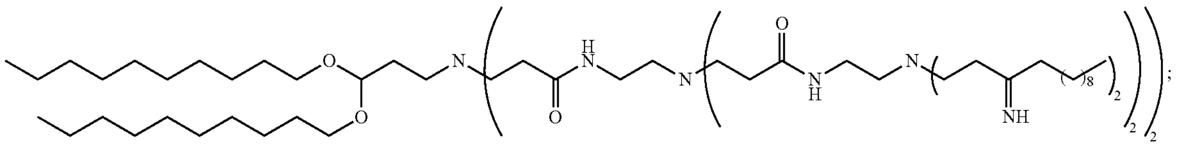
(G2-c1-amide-t1)
I-11
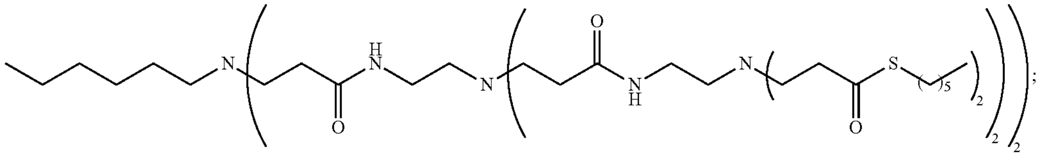
(G2-c2-amide-t2)
I-12
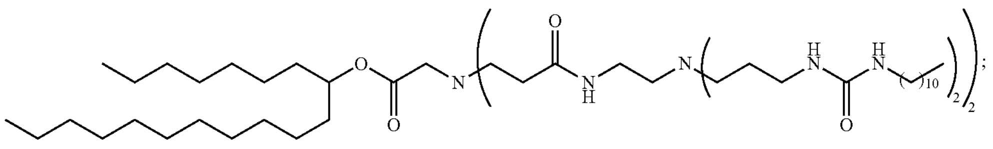
(G1-c3-amide-t3)

-continued
I-13
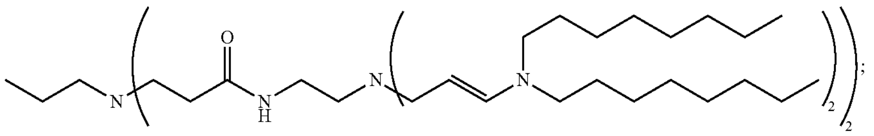
(G1-nPr-amide-t4)
I-14
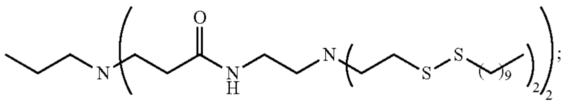
(G1-nPr-amide-t5)
I-15
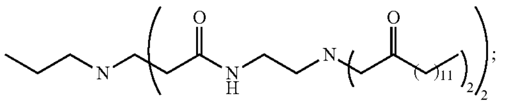
(G1-nPr-C14K)
I-16
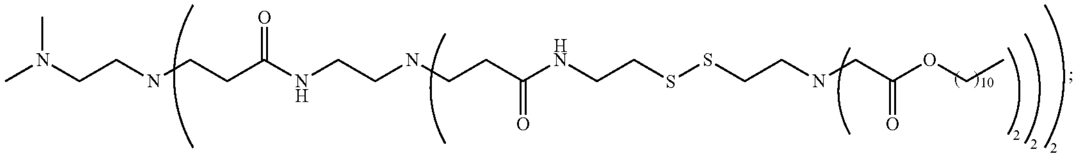
(G2-c4-amide-t7)
I-17
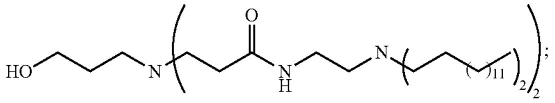
(G1-c5-amide-t8)
I-18
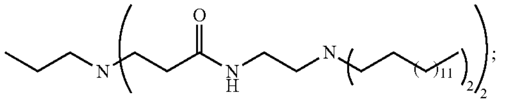
(G1-nPr-amide-t9)
I-19
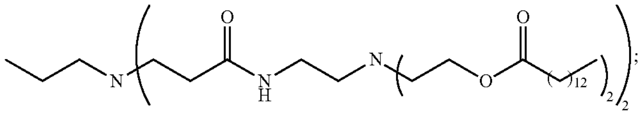
(G1-nPr-amide-t10)
I-20
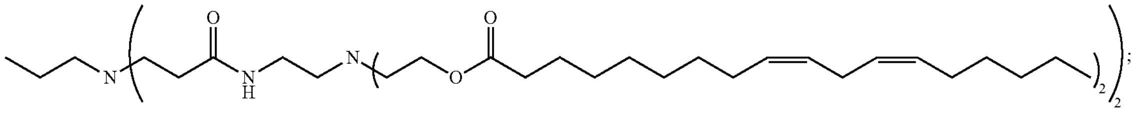
(G1-nPr-amide-t11)
I-21
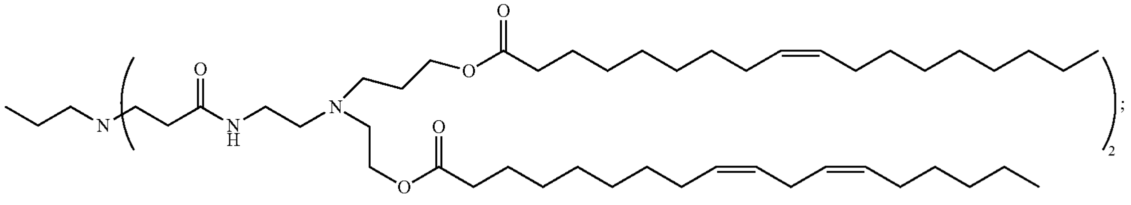
(G0-nPr-amide-t12)
I-22
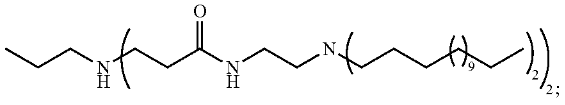
(G1-nPr-C14)
I-23
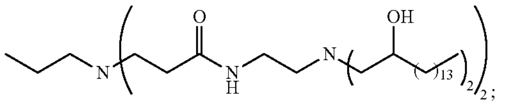
(G1-nPr-C16E)

-continued

I-24

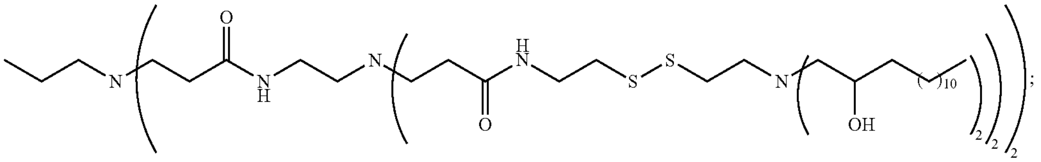;

(G2-nPr-S14-C14E)

I-25

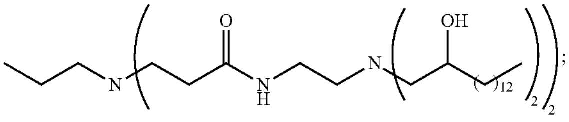;

(G1-C3-K2-E15)

I-26

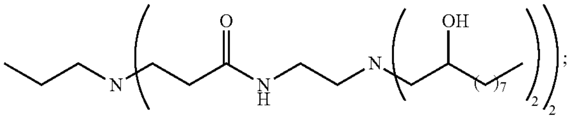;

(G1-C3-K2-E10)

I-27

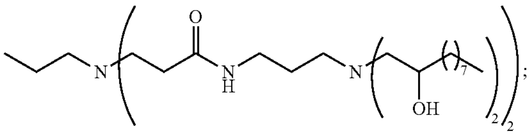;

(G1-C3-K3-E10)

I-28

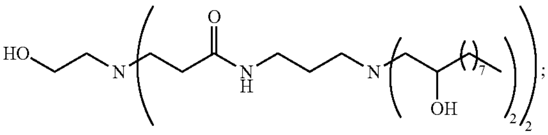;

(G1-OC2-K3-E10)

I-29

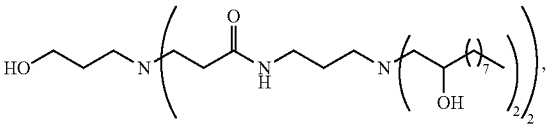, (G1-OC3-K3-E10)

I-30

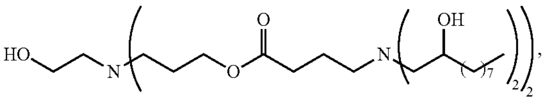, (DPA-GABA-E10)

I-31

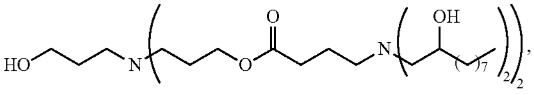, (TPA-GABA-E10)

I-32

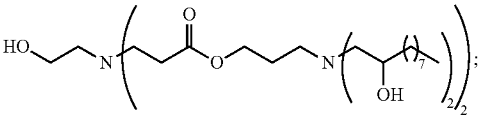; and (BU2-S3-E10)

I-33

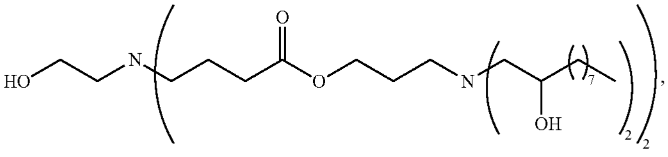, (BU3-S3-E10)

or a salt and/or solvate thereof.

The present application also includes compositions comprising one or more dendrons of the application. In some embodiments, the dendrons of the application are incorporated into a nanoparticle in the compositions. Therefore, the present application also includes a nanoparticle comprising one or more dendrons of the application. The present application also includes compositions comprising these nanoparticles. In some embodiments, the nanoparticles are formed by self-assembly of the one or more dendrons. In some embodiments, the nanoparticles comprise two or more dendrons of the application. In some embodiments, the nanoparticles are lipid nanoparticles (LNPs).

In some embodiments, the LNPs include one or more ionizable lipids (one or more dendrons of the application), one or more bi-layer-forming lipids, one or more structural lipids and one or more lipid-conjugated polyethylene glycols (PEG-lipids).

In some embodiments, the nanoparticles have a maximum longest straight dimension (e.g., diameter) of 200 nm or more. In some embodiments, the nanoparticles have a maximum longest straight dimension (e.g., diameter) of 200 nm or less. In some embodiments, the nanoparticles have a mean diameter of about 150 nm, about 125 nm, about 100 nm, about 90 nm, about 80 nm, about 70 nm, about 60 nm or less. In some embodiments, the nanoparticles have a mean diameter of 50 nm or less. In some embodiments, the nanoparticles have a mean diameter of 40 nm or less, 30 nm or less, 20 nm or less, 10 nm or less, or 5 nm or less. Thus, in some embodiments, the nanoparticles have a mean diameter of about 1 nm to about 50 nm, about 5 nm to about 30 nm, about 10 nm to about 25 nm, about 10 nm to about 20 nm, or about 15 nm to about 20 nm. In some embodiments, the nanoparticles disclosed herein have a mean diameter of about 150 nm, about 100 nm, about 90 nm, about 80 nm, about 70 nm, about 60 nm, about 50 nm, about 40 nm, about 30 nm, about 20 nm, about 15 nm, about 10 nm, or about 5 nm. In some embodiments, the mean diameter is determined using dynamic light scattering intensity.

In some embodiments, one or more dendrons of the application form colloids or supramolecular structures. Therefore, in some embodiments, the present application also includes a colloid comprising one or more dendrons of the application or a supramolecular structure comprising one or more dendrons of the application, as well as compositions comprising these colloids or supramolecular structures.

The present application also includes compositions comprising one or more dendrons of the application and one or more agents to be delivered to a cell or subject. In some embodiments, the one or more agents to be delivered to a cell or subject are selected from unmodified or modified nucleic acids, mitochondrion, plasmids, PolyIC and related adjuvants, ribonucleoproteins, proteins, peptides, cells, stains, dyes, small molecule drugs and other organic and inorganic moieties. In some embodiments, the one or more agents to be delivered to a cell or subject are selected from polynucleotides, chemically modified polynucleotides, small molecules, biologics and other organic or inorganic molecules. In some embodiments, the one or more agents to be delivered to a cell or subject are selected from dyes and radiolabeled compounds. In some embodiments, the one or more agents to be delivered to a cell or subject are vaccines. In some embodiments, the one or more agents to be delivered to a cell or subject are drugs. In some embodiments, the one or more agents to be delivered to a cell or subject are called a payload.

In some embodiments, the one or more agents to be delivered to a cell or a subject have an overall negative charge.

In some embodiments, the one or more agents to be delivered to a cell or a subject are located within a nanoparticle, colloid or supramolecular structure comprising one or more dendrons of the application. By "located within" it is understood that the one or more agents are encapsulated within the nanoparticle, colloid or supramolecular structure and/or are non-covalently associated with any portion of the one or more dendrons making up the nanoparticle, colloid or supramolecular structure.

In some embodiments, the proteins and peptides are selected from endonucleases, meganucleases, proteases and kinases.

In some embodiments, the one or more agents to be delivered to a cell or a subject are one or more nucleic acids. In some embodiments, the one or more nucleic acids are selected from a short interfering RNA (e.g. small interfering RNA or siRNA), circular RNA, cyclic RNA, long noncoding RNA, a microRNA (miRNA), a pri-miRNA, a messenger RNA (mRNA), a cluster regularly interspaced short palindromic repeats (CRISPR) related nucleic acid, a single guide RNA (sgRNA), a CRISPR-RNA (crRNA), a trans-activating crRNA (tracrRNA), a plasmid DNA (pDNA), a transfer RNA (tRNA), an antisense oligonucleotide (ASO), a guide RNA, a double stranded DNA (dsDNA), a single stranded DNA (ssDNA), exDNA, pro-form RNA, a single stranded RNA (ssRNA), and a double stranded RNA (dsRNA). In some embodiments, the one or more nucleic acids are selected from a siRNA, a tRNA, and a nucleic acid which is used in a CRISPR process. In some embodiments, the nucleic acid is a siRNA. In some embodiments, the nucleic acid which is used in a CRISPR process is a cluster regularly interspaced short palindromic repeats (CRISPR) related nucleic acid, a single guide RNA (sgRNA), a CRISPR-RNA (crRNA), and/or a trans-activating crRNA (tracrRNA). In some embodiments, the nucleic acid is a miRNA. In some embodiments, the nucleic acid is a mRNA. In some embodiments, the nucleic acid is a tRNA. In some embodiments, the nucleic acid is a guide RNA. In some embodiments, the guide RNA is used in CRISPR processes. In some embodiments, the nucleic acid is a pDNA.

In some embodiments the compositions of the application are for use in gene editing. In some embodiments, these compositions comprise cas9 mRNA and one or more guide RNA (gRNA) designed to target specific gene. In some embodiments these compositions further comprise DNA or are formulated for co-delivery with DNA, for homologous directed repair.

In some embodiments, the compositions of the application are for use in gene silencing. In some embodiments, these compositions comprise siRNA.

In some embodiments, the compositions of the application are used for gene regulation. In some embodiments, these compositions comprise non-coding RNA (ncRNA).

In some embodiments, the compositions of the application are used for gene expression upregulation or gene expression downregulation. In some embodiments, these compositions comprise unmodified or chemically modified messenger RNA (mRNA). In some embodiments, chemically modified mRNA refers to the partial or complete substitution of nucleotides with chemically modified nucleotides. In one embodiment, uridine is completely substituted by N1-methyl pseudouridine.

In some embodiments, the compositions of the application are used for antiviral treatment. In some embodiments, these compositions comprise mRNA encoding the Ca9 protein, and one or more sgRNAs. In some embodiments, the one or more sgRNAs identify viral genes for deletion.

In some embodiments, the dendron(s) and the one or more agents to be delivered to a cell or subject are present in a weight ratio from about 100:1 to about 1:5. In some embodiments, the weight ratio of dendron(s) to one or more agents to be delivered to a cell or subject is from about 50:1 to about 2:1. In some embodiments, the weight ratio of dendron(s) to one or more agents to be delivered to a cell or subject is 25:1.

In some embodiments, the composition further comprises one or more lipids. In some embodiments, the one or more lipids are selected from a steroid, a steroid derivative, a PEG-lipid, and a phospholipid.

In some embodiments, the PEG-lipid is a compound which contains one or more $C_{6-24}$alkyl or $C_{6-24}$alkenyl groups or a $C_{6-24}$ fatty acid group attached to a linker group with a PEG chain. Some non-limiting examples of a PEG-lipid include a PEG-modified phosphatidylethanolamine, PEG-modified phosphatidic acid, a PEG-ceramide conjugate, PEG-modified dialkylamine, PEG-modified 1,2-diacyloxypropan-3-amine, PEG-modified diacylglycerols and/or dialkylglycerols.

In some embodiments, the PEG-lipid is a PEG-modified 1,2-dimyristoyl-sn-glycero-3-phosphoethanolamine, a PEG-modified 1,2-distearoyl-sn-glycero-3-phosphoethanolamine, a PEG-modified 1,2-dioleoyl-sn-glycero-3-phosphoethanolamine, a PEG modified 1,2-dimyristoyl-sn-glycero-3-phosphoethanolamine, a PEG-modified 1,2-distearoyl-sn-glycero-3-phosphoethanolamme, a PEG-modified 1,2-dimyristoyl-rac-glycero-3-methoxypolyethylene glycol and/or a PEG-modified distearoyl-rac-glycerol.

In some embodiments, the PEG is measured by the molecular weight of PEG component of the lipid. In some embodiments, the PEG has a molecular weight (in g/mol or daltons) from about 100 to about 15,000. In some embodiments, the molecular weight is from about 200 to about 10000, from about 400 to about 8000, from about 1000 to about 6000, or from about 2000 to about 5000. In some embodiments, the molecular weight of the PEG is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present invention are taught by U.S. Pat. No. 5,820,873, WO 2010/141069, or U.S. Pat. No. 8,450, 298, which is incorporated herein by reference.

In some embodiments the PEG-lipid is a PEG-phospholipid conjugate, such as a PEGylated phosphoethanol amine lipid of the formula II:

(II)

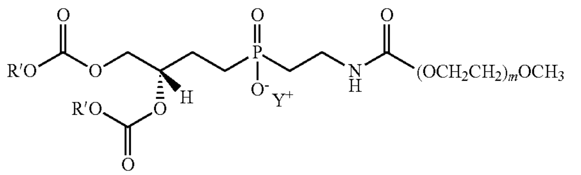

wherein

R' is $C_{6-24}$alkyl or $C_{6-24}$alkenyl having 1 or 2 double bonds;

m is an integer from 20 to 200; and

Y is any suitable counter cation.

In some embodiments, R' is $C_{12-20}$alkyl, or $C_{12-20}$alkenyl having one double bond. In some embodiments R' is $C_{14}$alkyl, $C_{16}$alkyl or $C_{18}$alkyl or R' is $C_{14}$alkenyl, $C_{16}$alkenyl or $C_{18}$alkenyl, each alkenyl group having one double bond.

In some embodiments, m is an integer from 40 to 120. In some embodiments, m is 45 (PEG2000) or 113 (PEG5000).

In some embodiments, Y is ammonium, or any other suitable counter cation.

In some embodiments, the compositions comprise a molar ratio of the PEG-lipid to the dendron of from about 1:1 to about 1:400 or 1:1 to about 1:250. In some embodiments, the molar ratio is from about 1:1, 1:10, 1:20, 1:30, 1:40, 1:50, 1:60, 1:70, 1:80, 1:90, 1:100, 1:110, 1:120, 1:125, 1:150, 1:175, 1:200, 1:225, to about 1:250 or any range derivable therein. In some embodiments the PEG-lipid is present at 0 to 50 mol % of total lipids or any range derivable therein. In some embodiments, the PEG-lipid is present at 0 mol %, 1.5 mol %, 3 mol %, 10 mol %, 15 mol %, 20 mol % or 40 mol % or any range derivable therein.

In some embodiments, the structural lipid is a steroid or steroid derivative. In some embodiments, the steroid or steroid derivative is unmodified or modified cholesterol, a phytosterol, cholecalciferol, dexamethasone, or any combination thereof. In some embodiments, modified cholesterol is oxidized on the beta-ring or on the hydrocarbon tail structure. In another embodiment, phytosterols include but are not limited to β-sitosterol, stigmasterol, β-sitostanol, campesterol, brassicasterol, salts and esters thereof. In some embodiments, the structural lipid and the dendron are present in a molar ratio from 2:1 to 1:20, or any range derivable therein. In some embodiments the structural lipid is present at 0 to 50 mol % of total lipids or any range derivable therein.

In some embodiments, bilayer-forming lipids are composed of naturally-occurring lipids or are of synthetic origin, including phospholipids, sphingolipids and glycolipids. Phospholipids include but are not limited to 1,2-distearoyl-sn-glycero-3-phosphocholine (DSPC) and 1,2-dioleoyl-sn-glycero-3-phosphoethanolamine (DOPE). In some embodiments, the sphingolipid is sphingomyelin. In some embodiments, the bilayer-forming lipid and the dendron are present in a molar ratio of from 2:1 to 1:20, or any range derivable therein. In some embodiments the structural lipid is present at 0 to 50 mol %, or up to 50 mol % of total lipids, or any range derivable therein.

In some embodiments, the application includes a composition comprising one or more dendrons of the application, one or more PEG-lipids, one or more phospholipids, and one or more steroids. In some embodiments, the one or more dendrons are present in an amount of about 45 mol % to about 55 mol %, the one or more phospholipids are present in an amount of about 33.5 mol % to about 43.5 mol %, the one or more PEG-lipids are present in an amount of about 0.5 mol % to about 2.5 mol % and the one or more steroids are present in an amount of about 5 mol % to about 15 mol %. In some embodiments, the one or more dendrons are present in an amount of about 50 mol %, the one or more phospholipids are present in an amount of about 38.5 mol %, the one or more PEG-lipids are present in an amount of about 1.5 mol % and the one or more steroids are present in an amount of about 10 mol %.

In some embodiments, the application includes a composition comprising one or more dendrons of the application, one or more PEG-lipids, one or more phospholipids, one or more steroids and one or more agents to be delivered. In some embodiments, the steroid is cholesterol. In some embodiments, the steroid is β-sitosterol.

In some embodiments, when lipids are present in a composition comprising one or more agents to be delivered, the one or more agents to be delivered to a cell or subject are present in a weight ratio of the one or more dendrons plus lipids:agent(s) of from about 100:1 to about 1:5, about 50:1 to about 2:1 or about 25:1. In some embodiments, the mol % ratio of the one or more dendrons plus lipids:agent(s) is in the range of about 95 mol %:5 mol % to about 80 mol %:20 mol %.

In some embodiments, when the one or more agents to be delivered is RNA, the compositions comprise a lipid nitrogen to RNA phosphate ratio (N/P) of about 5.

The present application also includes a pharmaceutical composition comprising: a composition or dendron of the application and a pharmaceutically acceptable carrier.

In some embodiments, the pharmaceutical acceptable carrier is a solvent or solution. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical composition is formulated for intravenous or intraarterial injection. In some embodiments, the pharmaceutical composition is formulated as a unit dose. In some embodiments, the pharmaceutical composition is formulated for administration intramuscularly.

In some embodiments, the compositions and pharmaceutical compositions of the application have at pH of about 2 to about 8.5. In some embodiments, the composition is formulated in 10 to 100 mM citrate buffer at pH 3, 4, 5 or 6. It is to be understood that the pH of the compositions of the application may be any suitable pH during preparation and storage. However, for delivery of the compositions of the application to a cell or subject, the pH is adjusted to be physiologically acceptable, such as a pH of about 7. In some embodiments, the compositions and pharmaceutical compositions of the application have a polydispersity index (PDI) of less than 0.2. In some embodiments, the compositions and pharmaceutical compositions of the application have a pKa of about 4 to about 8. In some embodiments, the compositions and pharmaceutical compositions of the application have a pKa of about 5 to about 7. In some embodiments, the compositions and pharmaceutical compositions of the application have a pKa of about 5.5.

In some embodiments, the composition and pharmaceutical compositions of the application have an encapsulation efficiency of above about 90%. In some embodiments, the encapsulation efficiency is above about 93%. In some embodiments, the encapsulation efficiency is above about 95%.

The present application also includes kits. Any of the components disclosed herein may be combined in the form of a kit. In some embodiments, the kits comprise a dendron or a composition as described above.

The kits will generally include at least one vial, test tube, flask, bottle, syringe or other container, into which a component is placed, and optionally, suitably aliquoted. Where there is more than one component in the kit, the kit also will generally contain a second, third or other additional containers into which the additional components are separately placed. However, various combinations of components may be comprised in a container. In some embodiments, all of the delivery components are combined in a single container. In other embodiments, some or all of the dendron delivery components are provided in separate containers.

The kits of the present application also will typically include packaging for containing the various containers in close confinement for commercial sale. Such packaging may include cardboard or injection or blow molded plastic packaging into which the desired containers are retained. In some embodiments, a kit will also include instructions for employing the kit components. Instructions may include variations that can be implemented. In some embodiments, the instructions are for delivery of the one or more dendrons or the one or more compositions to a subject or cell.

Methods and Uses of the Application

The present application includes methods for delivering one or more agents to a cell or subject using the dendrons and/or compositions of the application. Accordingly, in some embodiments, the present application includes a method of delivering one or more agents to a cell comprising contacting the cell with one or more dendrons or compositions or pharmaceutical compositions of the application under conditions to cause uptake of the agent into the cell. In some embodiments, the present application includes a method of delivering one or more agents to a subject comprising contacting the subject with one or more dendrons or compositions or pharmaceutical compositions of the application. In some embodiments, the cell is contacted in vitro. In some embodiments, the cell is contacted in vivo. In some embodiments, the cell is contacted ex vivo. In some embodiments, the contacting is for the purpose of treating a disease, disorder or condition. In some embodiments, the contacting is for diagnosing a disease, disorder or condition. In some embodiments, the contacting is by administrating an effective amount of the one or more dendrons or compositions or pharmaceutical compositions of the application to a cell or a subject in need thereof.

In some embodiments, the present application also includes a use of one or more dendrons or compositions or pharmaceutical compositions of the application for diagnostic, prophylactic, or therapeutic applications. In some embodiments, the uses are connected to the payload delivered by the composition. In some embodiments, the payloads include polynucleotides, chemically modified polynucleotides, small molecules, biologics or other organic or inorganic moieties. Diagnostic applications include use of one or more dendrons or compositions or pharmaceutical compositions of the application as carriers of an identifiable label, such as a dye or radiolabel, that after administration can be detected and is indicative of a disease, disorder or condition. Prophylactic applications include use as vaccines, including vaccines for infectious disease, or vaccines for another anticipated or potential condition of a subject. Therapeutic applications include use for treating any disease, disorder or condition, including but not limited to, infectious disease, autoimmune disease, cancer, a genetic disease, chronic disease, traumatic injuries, wound healing, traumatic brain injury, muscular disease, neuromuscular disease and/or gastrointestinal disease. Therapeutic applications may be in vivo, or may be ex vivo therapy treatments where cells, tissues or organs are treated ex vivo and are implanted or transplanted into the subject.

In some embodiments, the present application also includes a use of one or more dendrons or compositions or pharmaceutical compositions of the application to deliver one or more agents to a cell, either in vitro, in vivo or ex vivo.

In some embodiments, the one or more agents to be delivered to the cell are one or more nucleic acids. Therefore, the present application also includes methods of modulating the expression of a gene comprising delivering one or more nucleic acids to a cell, the methods comprising contacting the cell with one or more dendrons or compositions or pharmaceutical compositions of the application under conditions to cause uptake of the one or more nucleic acids into the cell. In some embodiments, the cell is contacted in vitro. In some embodiments, the cell is contacted in vivo. In some embodiments, the cell is contacted ex vivo. In some embodiments, the modulation of the gene expression is sufficient to treat a disease, disorder or condition.

In some embodiments, the disease, disorder or condition is, for example, but not limited to, infectious disease, autoimmune disease, cancer, a genetic disease, chronic disease, traumatic injuries, wound healing, traumatic brain injury, neuromuscular disease and/or gastrointestinal disease.

In some embodiments, the present application also includes a use of one or more dendrons or compositions or pharmaceutical compositions of the application to modulating the expression of a gene. In some embodiments the expression of the gene is modulated by delivering one or more nucleic acids to a cell, either in vitro, in vivo or ex vivo.

In some embodiments, when the compositions and pharmaceutical compositions of the application comprise siRNA, miRNA and mRNA as the one or more agents to be delivered to a cell or subject, this formulated delivery composition is designed to target the bone marrow endothelial cells to suppress, regulate or induce genes causing events leading to chronic inflammation. Currently autoimmune diseases are a major source of chronic inflammation and affect approximately two million Canadians. Due to their complex nature, autoimmune diseases are incompletely understood and therefore provide a challenge when discussing therapeutic options. Current treatments include immunosuppressants, corticosteroids and pain management. These current treatment options do not provide long term or permanent results and need to be optimized. Chronic and severe inflammation is caused by overexpression and the movement of monocytes and monocyte derived macrophages through the body to targeted areas. The majority of monocytes and monocyte derived macrophages are produced in the bone marrow and then are able to cross the endothelial barriers and travel through the bloodstream to targeted areas. With the bone marrow being a major source of production of monocytes, by directly targeting the area of mass production, the course of monocyte proliferation and egress into the blood stream can be altered. The silencing effect of siRNA encompassed in the nanoparticle will be able to suppress the proliferation of monocytes as well as suppressing their ability to leave the bone marrow. By not only reducing their ability to travel freely but also reduce the total number within the body, the inflammatory response that is leading to damaging effects in people suffering from chronic inflammation can be effectively reduced. Accordingly, in some embodiments, the present application includes a method of treating chronic inflammation comprising administering an effective amount of a composition comprising one or more dendrons of the application, siRNA, miRNA and mRNA to a cell or subject in need thereof. Also included is a use of a composition comprising one or more dendrons of the application, siRNA, miRNA and mRNA to treat chronic inflammation. In some embodiments, the siRNA is siRNA against bone marrow endothelial genes needed for monocyte attachment and transit into blood circulation.

In some embodiments the compositions of the application are for use in gene editing. Accordingly, in some embodiments, the present application includes a method of editing a genome of a cell comprising contacting the cell with one or more compositions of the application. Also included is a use of one or more compositions of the application for gene editing. In some embodiments, these compositions comprise cas9 mRNA and one or more guide RNA (gRNA) designed to target specific genes and the one or more compositions are contacted with the cell under conditions to cause uptake of the cas9 mRNA and one or more gRNA into the cell. Upon uptake into the cell, cas9 mRNA is translated into Cas9 protein and incorporates the gRNA to target the sequence of interest within the nucleus. DNA can also be co-delivered for homologous directed repair.

In some embodiments, the compositions of the application are for use in gene silencing. Accordingly, in some embodiments, the present application includes a method of silencing a gene in a cell comprising contacting the cell with one or more compositions of the application. Also included is a use of one or more compositions of the application for gene silencing. In some embodiments, these compositions comprise siRNA and upon delivery to a cell, silence genes corresponding to the siRNA. Accordingly, the one or more compositions are contacted with the cell under conditions to cause uptake of the siRNA into the cell.

In some embodiments, the compositions of the application are used for gene regulation. In some embodiments, these compositions comprise non-coding RNA (ncRNA), and the one or more compositions are contacted with the cell under conditions to cause uptake of the ncRNA into the cell and upon uptake into the cell, regulate genes associated with the ncRNA.

In some embodiments, the compositions of the application are used for gene expression upregulation or gene expression downregulation. Accordingly, in some embodiments, the present application includes a method of regulating expression of a gene in a cell comprising contacting the cell with one or more compositions of the application. Also included is a use of one or more compositions of the application for regulating expression of a gene in a cell. In some embodiments, these compositions comprise messenger RNA (mRNA) and the one or more compositions are contacted with the cell under conditions to cause uptake of the mRNA into the cell and upon uptake into the cell, express a protein.

In some embodiments, the compositions of the application may be used in the treatment or prevention of infectious diseases, autoimmune diseases, cancer, genetic diseases, chronic diseases, traumatic injuries, wound healing, traumatic brain injuries, neuromuscular diseases and/or gastrointestinal diseases.

In some embodiments, the compositions of the application are used for antiviral treatment. Accordingly, in some embodiments, the present application includes a method of treating a viral infection comprising administering one or more compositions of the application to a cell or subject in need thereof. Also included is a use of one or more compositions of the application for treating a viral infection. In some embodiments, these compositions comprise mRNA encoding the Ca9 protein, and one or more sgRNAs. In some embodiments, the one or more sgRNAs identify viral genes for deletion. In some embodiments, the virus is a DNA virus or an RNA virus.

In some embodiments, the compositions of the application are used in methods of delivering one or more proteins to cells, delivering one or more small molecule drugs to cells or delivering one or more DNA molecules to cells.

In some embodiments, the compositions of the application are used in cosmetic and/or personal care products and the one or more agents to be delivered to a cell or subject are any such agent. In some embodiments, the one or more agents for cosmetic and/or personal care products include, but are not limited to, hair moisturizing agents, hair growth agents, hair anti-frizz agents, skin moisturizing agents, anti-aging agents and temporary bioluminescent proteins.

In some embodiments, the compositions of the application are used in methods of preventing forgery, for example to confirm that a product or packaged has not been tampered with or is the original form. In these embodiments, the one or more agents will include unique DNA or RNA sequences (barcodes) that are put into product packaging/labels that can be read to ensure the product is genuine or not tampered with and the compositions of the application are delivered onto or into a subject that is a package.

In some embodiments, the compositions in the methods and uses are pharmaceutical compositions as defined above.

In some embodiments, the cells in the methods and the uses of the application are in vitro. In some embodiments, the cells in the methods and the uses of the application are in vivo. In some embodiments, the cells in the methods and the uses of the application are ex vivo.

In some embodiments, the cells are animal cells. In some embodiments, the animal cells are mammalian cells. In some embodiments, the cells are human cells. In some embodiments, the cells are plant cells.

Preparation of Dendrons and Compositions of the Application

The dendrons of the present application can be prepared by various synthetic processes. The choice of particular structural features and/or substituents may influence the selection of one process over another. The selection of a particular process to prepare a given dendron of Formula (I) is within the purview of the person of skill in the art. Some starting materials for preparing dendrons of the present application are available from commercial chemical sources. Other starting materials, are readily prepared from available precursors using straightforward transformations that are well known in the art.

In some embodiments, the dendrons of Formula I are assembled by attaching the various portions of the molecule together in specific order depending on the functional groups that are present. Standard chemistries known in the art can be used to assemble the dendrons of Formula I, including but not limited to, nucleophilic displacements, cross-couplings, Michael reactions and/or activating group strategies. As many of the portions of the dendrons are known, or are based on known compounds, compounds that can be used to link the portions of the molecule together are readily available either from commercial sources or using synthetic methods known in the art. For example, many such compounds have at least one functional group in their structure capable of forming a covalent bond with the linker group. Examples of such include an amine, thiol, halo, hydroxyl, alkoxy, carboxyl, ester, amide and/or oxo group.

In an exemplary embodiment, to synthesize Generation 1 (G1) and Generation 2 (G2) poly-amidoamine (PAMAM) dendron macromolecules the following steps as shown in Scheme 1 are followed. An addition reaction of, for example, n-propylamine (or any other suitable amine of the formula $R^1$—$NH_2$) with, for example, methyl acrylate (or any other suitable linker group) forms intermediate A, followed by condensation with, for example, ethylenediamine to form intermediate B. Intermediate B may then undergo alkylation, for example via epoxide ring opening, to form a Generation 1 dendron, wherein R is a terminal group, or it may undergo a second set of addition and condensation reactions to form intermediate C and D respectively. Alkylation of intermediate D, for example via epoxide ring opening, forms a Generation 2 dendron, wherein each R is a terminal group.

Scheme 1

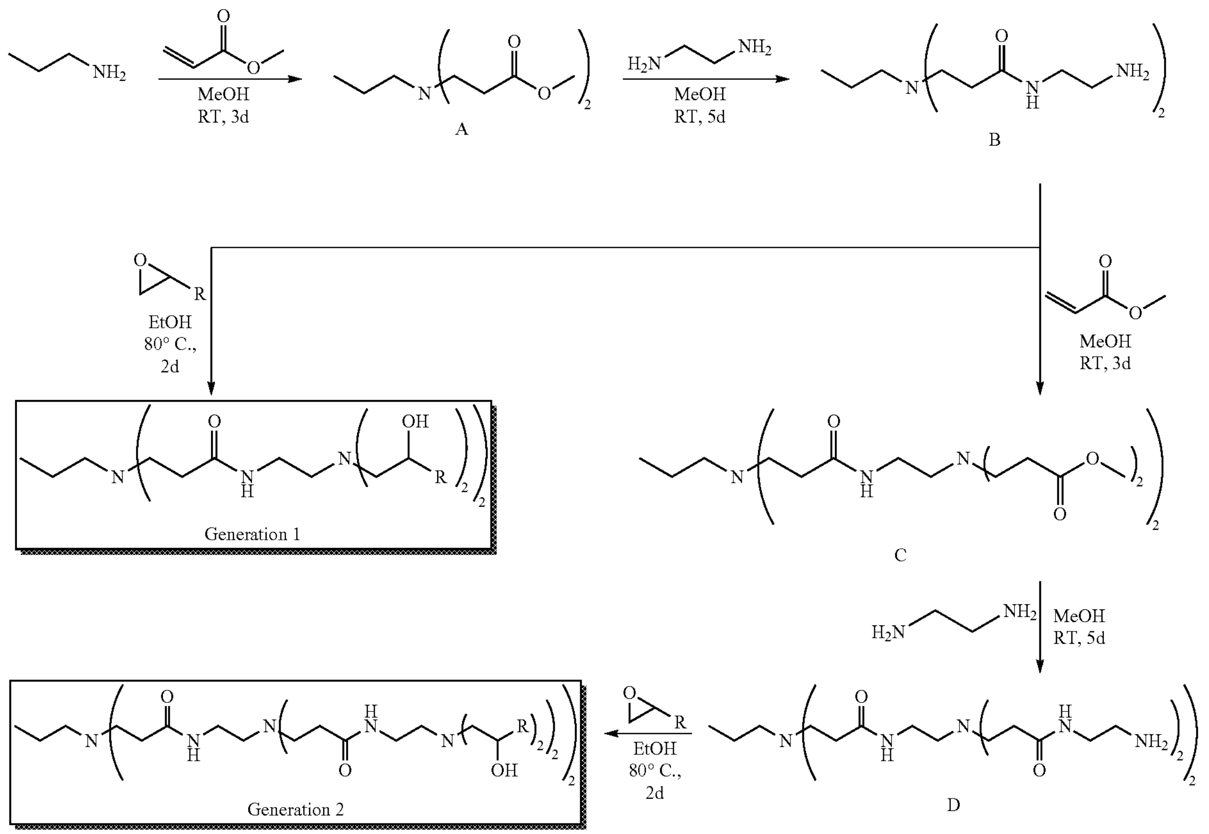

In a further exemplary embodiment as shown in Scheme 2, to synthesize a bioreducible Generation 1 modified dendron, intermediate A is formed by reacting, for example, n-propylamine (or any other suitable amine of the formula $R^1$—$NH_2$) and, for example, methyl acrylate (or any other suitable linker group). A further condensation reaction with cystamine forms intermediate E, which may then undergo alkylation, for example via epoxide ring opening, to form a bioreducible Generation 1 dendron, wherein R is a terminal group.

Scheme 2

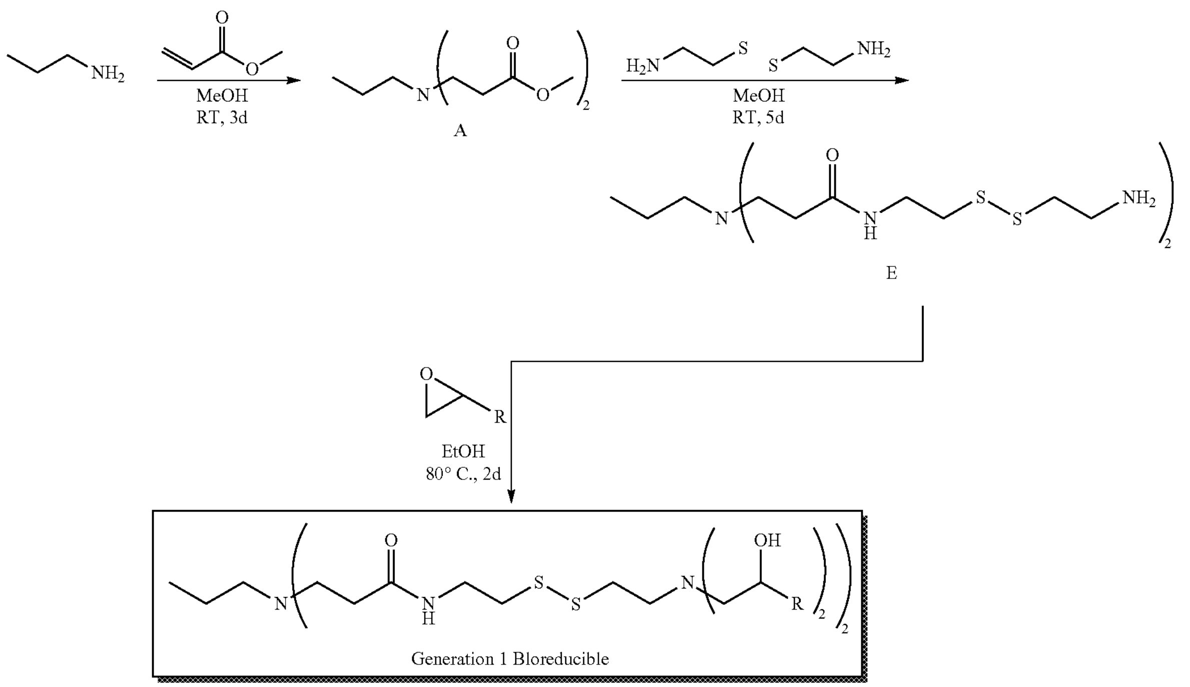

In a further exemplary embodiment as shown in Scheme 3, to synthesize a bioreducible Generation 2 modified dendron, intermediate C is formed as in Scheme 1. A further condensation reaction with cystamine forms intermediate F, which may then undergo alkylation, for example via epoxide ring opening, to form a bioreducible Generation 2 dendron wherein R is a terminal group.

Scheme 3
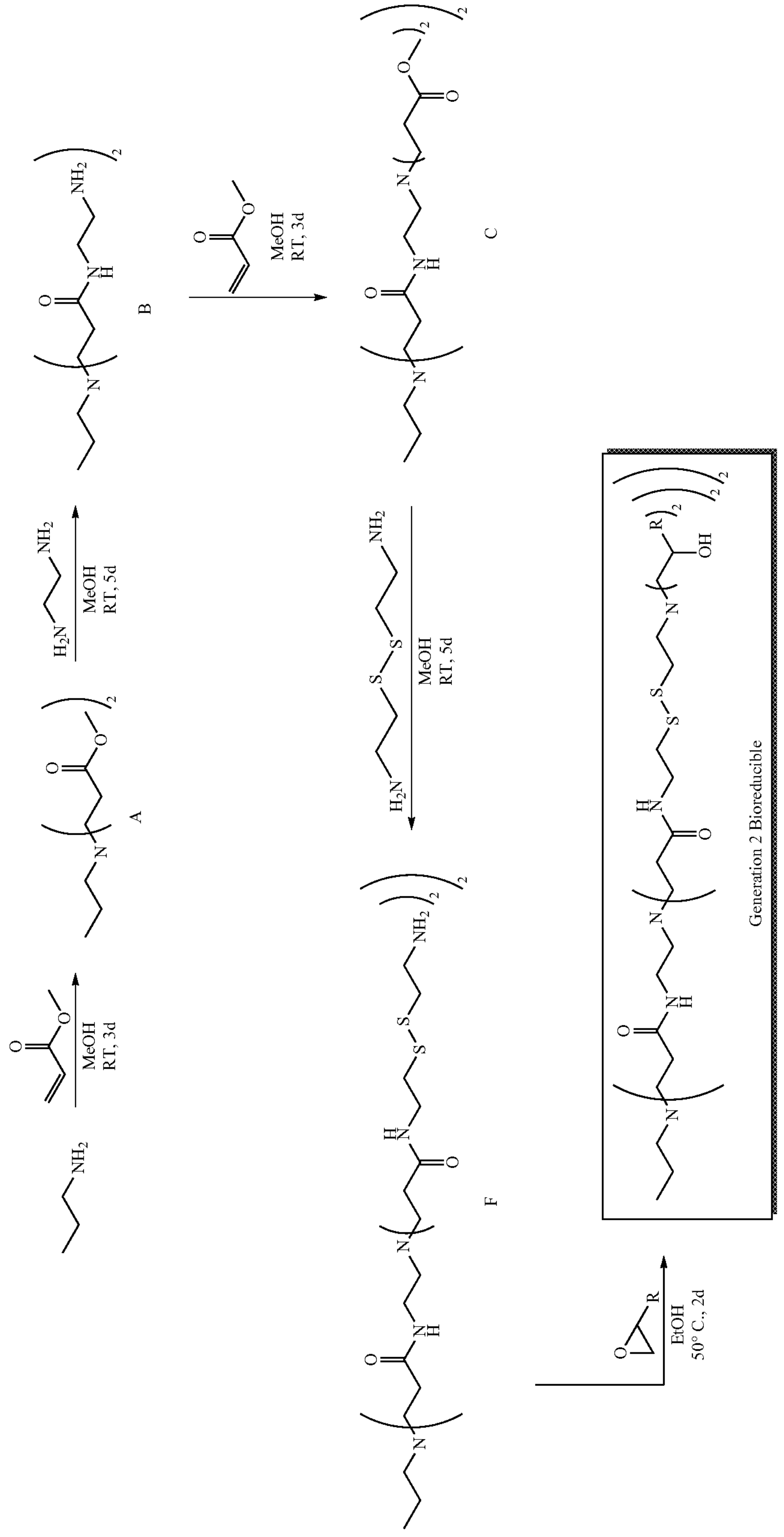

In a further exemplary embodiment shown in Scheme 4, alkylation of intermediate B or D from Scheme 1 is alternatively performed via the reductive amination of an aldehyde or ketone in the presence of a reducing agent such as sodium triacetoxyborohydride.

Scheme 4

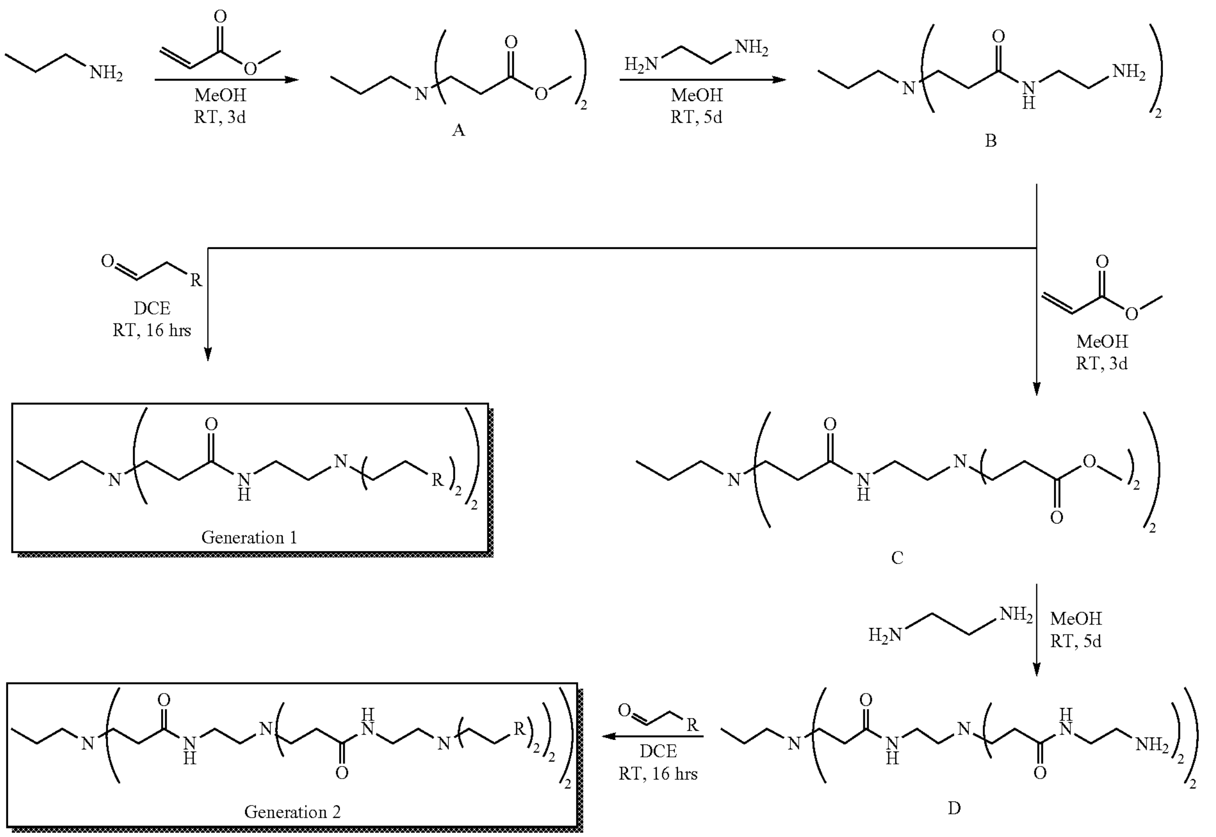

Throughout the processes it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994).

Techniques for purification of intermediates and final products include, for example, straight and reversed phase chromatography on column or rotating plate, recrystallisation, distillation and liquid-liquid or solid-liquid extraction, which will be readily understood by one skilled in the art.

Salts of the dendrons of the application are generally formed by dissolving a neutral compound in an inert organic solvent and adding either the desired acid or base and isolating the resulting salt by either filtration or other known means.

The formation of solvates of the dendrons of the application will vary depending on the compound and the solvate. In general, solvates are formed by dissolving a compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The following non-limiting examples are illustrative of the present application.

Compositions of the present application are prepared by combining dendrons of the application and optional excipients under conditions to form nanoparticles, colloids and/or supramolecular structures, suitably comprising one or more agents to be delivered. In some embodiments, the conditions to form nanoparticles, colloids and/or supramolecular structures comprise first combining the one or more dendrons and any optional excipients, including the one or more PEG-lipids, one or more phospholipids, and/or one or more steroids in a suitable solvent such as ethanol. In some embodiments, sonication and/or warming is used to eliminate any precipitate. Separately the one or more agents to be delivered are prepared in a suitable solvent, such as an aqueous buffer, such as an aqueous citrate buffer. The two solutions are then combined under conditions to form nanoparticles, colloids and/or supramolecular structures. In some embodiments, the two solutions are combined under continuous flow conditions using, for example, microfluidics. In some embodiments the resulting nanoparticles, colloids and/or supramolecular structures are treated using dialysis to adjust the pH. In some embodiments, particles are stored at room temperature or −20° C. for at least 48 hours without any noticeable changes.

EXAMPLES

General Methods

Several modified Generation 1 (G1) and Generation 2 (G2) poly-amidoamine (PAMAM) dendron macromolecules are synthesized. These macromolecules are combined with lipid-polyethylene glycol (PEG-lipid) excipients, in an ethanol (EtOH) phase, creating a delivery material for sequestering nucleic acids. RNA nanoparticles are then formed by combining the delivery material with different nucleic acids in a citrate buffer at varying pH levels.

Example 1: Synthesis of Multi-Motif PAMAM Dendron Macromolecules

With respect to the PAMAM macromolecules, $^{1}H$, $^{13}C$, and $^{19}F$ NMR spectra were recorded on a machine operating at 500 MHz for $^{1}H$ NMR, at 126 MHz, 400 MHz or 500 MHz for $^{13}C$ NMR, and at 400 MHz for $^{19}F$ NMR, using tetramethylsilane (TMS) or the residual solvent signal as an internal reference, in deuterated chloroform as solvent, unless otherwise indicated. All reported chemical shifts are in ppm on the delta-scale, and the fine splitting of the signals as appearing in the recordings is generally indicated, for example as br=broad, s=singlet, d=doublet, t=triplet, q=quartet, p=pentet, and m, multiplet; coupling constants in Hz. $^{1}H$ and $^{13}C$ NMR were recorded on either an Agilent DD2 500 MHz w/direct cryoprobe (126 MHz), or an Agilent VnmrS 400 MHz and referenced to $CDCl_3$ at 7.26 ppm ($^{1}H$) and 77.16 ppm ($^{13}C$). Matrix-assisted laser desorption ionization time-of-flight mass spectra (MALDI-TOF MS) spectra were recorded on a Bruker AutoFlex Speed using dithranol matrix, direct analysis in real time mass spectra (DART MS) were recorded on a JEOL AccuTOF Plus 4G, electrospray ionization mass spectra (ESI MS) were recorded on an Agilent 6538 UHD.

Intermediate A

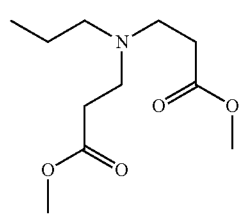 [SMILES: CCCN(CCC(=O)OC)CCC(=O)OC]

Preparation 1

A solution of n-propylamine (2.5 g, 42.3 mmol, 1 eq) in methanol was added dropwise to a solution of methyl acrylate (35.31 g, 422.9 mmol, 10 eq) in methanol. The mixture was stirred for 72 hours at room temperature. Solvent and excess methyl acrylate were removed under reduced pressure. Further purification (if necessary) was carried out by flash chromatography using a gradient from 100% dichloromethane (DCM) to 7% MeOH/DCM. Intermediate A was isolated as a light-yellow, clear oil (8.47 g, 86%).

$^{1}H$ NMR (400 MHz, $CDCl_3$) δ 3.61 (s, 6H), 2.71 (t, J=7.2 Hz, 4H), 2.39 (t, J=7.2 Hz, 4H), 2.32 (t, 2H, J=7.3 Hz), 1.38 (sextet, J=7.3 Hz, 2H), 0.80 (t, J=7.3 Hz, 3H). $^{13}C$ NMR (400 MHz, $CDCl_3$) δ 173.04, 77.40, 77.08, 76.76, 55.72, 51.43, 49.31, 32.59, 20.32, 11.65.

Preparation 2

Methyl acrylate (7.28 g, 84.6 mmol, 5 eq) was added together with n-propylamine (1.0 g, 16.9 mmol, 1 eq) in methanol (10 mL). The mixture was purged with nitrogen, covered with foil, and stirred for 72 hrs at room temperature. Consumption of n-propylamine was monitored by thin layer chromatography (TLC) (10% MeOH/dichloromethane (DCM)). Solvent and excess methyl acrylate were removed under reduced pressure. Intermediate A was isolated as a clear, colourless oil with a minor methyl acrylate impurity. (4.08 g, 17.6 mmol, 104%).

Intermediate B

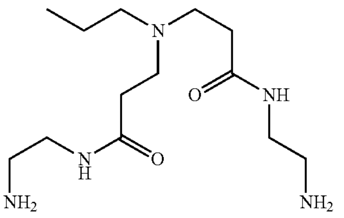 [SMILES: CCCN(CCC(=O)NCCN)CCC(=O)NCCN]

Preparation 1

A solution of ethylenediamine (20.79 g, 345.9 mmol, 40 eq) in methanol was added dropwise to a solution of Intermediate A (2.00 g, 8.65 mmol, 1 eq) in methanol. The mixture was stirred for one week at room temperature. Solvent and excess ethylenediamine were removed under reduced pressure to yield Intermediate B (2.88 g, 116%) as a yellow, viscous oil with residual ethylenediamine.

$^1$H NMR (500 MHz, $CDCl_3$) δ 7.49 (t, J=5.7 Hz, 2H), 3.27 (q, J=5.7 Hz, 4H), 2.81 (t, J=6.0 Hz, 4H), 2.71 (t, 4H), 2.41-2.30 (m, 6H), 1.45 (sextet, J=7.4 Hz, 2H), 0.85 (t, J=7.4 Hz, 3H). $^{13}$C NMR (500 MHz, $CDCl_3$) δ 172.86, 55.67, 50.23, 42.04, 41.53, 34.13, 19.99, 12.02.

Preparation 2

Ethylenediamine (15.6 g, 259 mmol, 20 eq) and Intermediate A (3.0 g, 13 mmol, 1 eq) were added together in methanol (10 mL). The mixture was purged with nitrogen, covered with foil, and stirred for 5 days at room temperature. Consumption of Intermediate A was monitored by TLC (15% MeOH/DCM) Solvent and excess ethylenediamine were removed under reduced pressure. The residual ethylenediamine was removed by successive washes with diethyl ether (5×30 mL). Residual ether was removed under vacuum to yield Intermediate B as a clear, colourless, viscous oil (1.604 g, 5.58 mmol, 43%).

$^1$H NMR (400 MHz, $CDCl_3$) δ 7.71 (t, J=5.7 Hz, 2H), 2.98 (q, J=5.9 Hz, 4H), 2.52 (t, J=6.0 Hz, 4H), 2.46 (t, J=6.3 Hz, 4H), 2.17-2.03 (m, 6H), 1.35 (s, 8H), 1.19 (sextet, J=7.4 Hz, 1H), 0.59 (t, J=7.3 Hz, 3H). $^{13}$C NMR (400 MHz, $CDCl_3$) δ 172.44, 55.01, 49.55, 48.88, 41.80, 41.12, 33.33, 19.46, 11.46.

I-1 (G1-nPr-C14E)

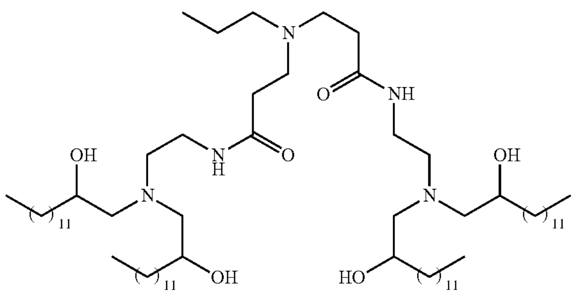

Preparation 1

A solution of 1,2-epoxytetradecane (1.03 g, 4.4 eq) in EtOH was added to a solution of Intermediate B (0.3 g, 1 eq) in EtOH in a sealed pressure vessel. The mixtures were stirred at 80° C. for 72 hours. Solvent was removed under reduced pressure. The crude oil was purified by flash chromatography using a gradient from 20% to 100% ULTRA solvent in DCM. The desired fractions were combined and concentrated under reduced pressure to yield a light yellow, viscous oil (0.76 g, 64%). $^1$H NMR (500 MHz, $CDCl_3$) δ 7.78 (br s, <2H), 3.28 (br s, <1H), 3.0-2.2 (m, 20H), 1.6-1.1 (m, 105H), 0.87 (m, 15H). $^{13}$C NMR (500 MHz, $CDCl_3$) δ 172.69, 70.68, 68.10, 64.74, 61.08, 50.02, 31.92, 29.66, 25.75, 22.68, 14.10, 11.82. MS (MALDI-TOF pos) m/z: $[M+H]^+$ calc'd for $C_{69}H_{141}N_5O_6$, 1137.09; found, 1137.16.

Preparation 2

A mixture of 1,2-epoxytetradecane (1.17 g, 5.51 mmol, 4.4 eq) and Intermediate B (0.36 g, 1.25 mmol, 1 eq) were added together in an 8-dram screw-cap vial. The vial was covered with foil and stirred at 90° C. overnight. Consumption of Intermediate B was monitored by TLC (35% ULTRA/DCM). The crude oil was purified by flash chromatography using a 50 g silica cartridge and a solvent gradient from 10% ULTRA/DCM to 20% ULTRA/DCM. The desired fractions were combined and concentrated under vacuum to a pale-yellow, clear, viscous oil (0.39 g, 0.34 mmol, 28%). $^1$H NMR (500 MHz, $CDCl_3$) δ 7.96-7.86 (m, 2H), 3.57-3.45 (m, 5H), 3.19 (q, J=4.7 Hz, 1H), 2.71-2.63 (m, 4H), 2.62-2.53 (m, 3H), 2.53-2.45 (m, 2H), 2.41-2.20 (m, 10H), 1.53-1.04 (m, 105H), 0.91-0.66 (m, 15H). $^{13}$C NMR (500 MHz, $CDCl_3$) δ 70.46, 70.36, 70.27, 68.09, 67.92, 64.87, 64.74, 64.63, 61.50, 61.43, 56.77, 55.71, 55.19, 49.77, 49.72, 49.68, 38.51, 37.35, 35.26, 35.16, 35.01, 34.94, 33.68, 33.54, 31.89, 29.84, 29.68, 29.64, 29.34, 25.78, 25.74, 22.64, 19.58, 14.06, 11.81. MS (ESI+) m/z: $[M+H]^+$ calc'd for $C_{69}H_{141}N_5O_6$, 1137.92; found, 1137.09.

I-23 (G1-nPr-C16E)

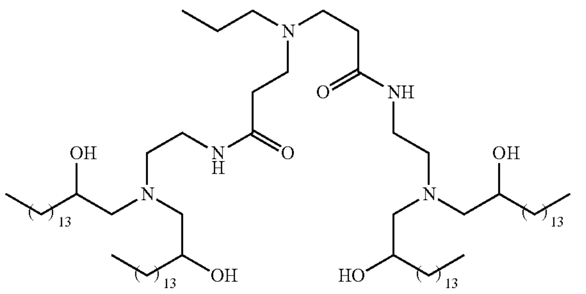

A solution of 1,2-epoxyhexadecane (1.3 g, 4 eq) in EtOH was added to a solution of Intermediate B (0.3 g, 1 eq) in EtOH in a sealed pressure vessel. The mixtures were stirred at 80° C. for 72 hours. Solvent was removed under reduced pressure. The crude oil was purified by flash chromatography using a gradient from 20% to 100% ULTRA solvent in DCM. The desired fractions were combined and concentrated under reduced pressure to yield a light yellow, viscous oil (0.42 g, 32%). $^1$H NMR (500 MHz, $CDCl_3$) δ 7.95-7.80 (m, 1H), 3.25 (br s, 1H), 2.80-2.20 (m, 20H), 1.6-1.1 (m, 125H), 0.84 (t, J=6.9 Hz, 15H). $^{13}$C NMR (500 MHz, $CDCl_3$) δ 172.98, 70.55, 68.08, 64.73, 61.25, 58.02, 53.37, 31.90, 29.69, 22.65, 14.07. MS (DART pos) m/z: $[M-OH]^+$ calc'd for $C_{69}H_{140}N_5O_5$, 1232.21; found, 1232.66.

I-2 (G1-nPr-C10O1E)

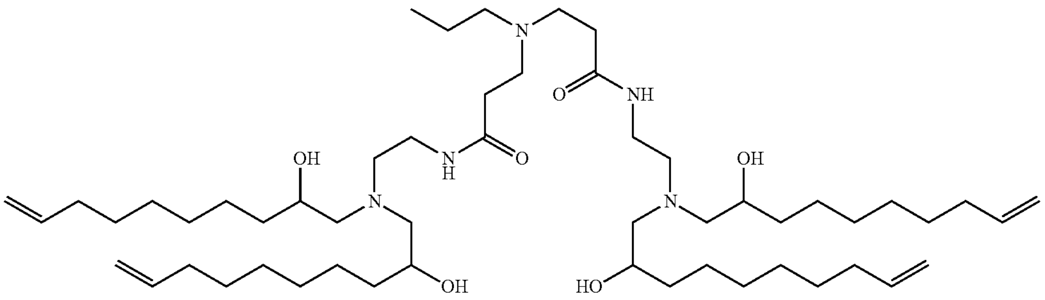 [SMILES: C=CCCCCCCC(O)CN(CCNC(=O)CCN(CCC)CCC(=O)NCCN(CC(O)CCCCCCC=C)CC(O)CCCCCCC=C)CC(O)CCCCCCC=C]

A solution of 1,2-epoxy-9-decene (0.49 g, 4 eq) in EtOH was added to a solution of Intermediate B (0.23 g, 1 eq) in EtOH in a sealed pressure vessel. The mixtures were stirred at 80° C. for 72 hours. Solvent was removed under reduced pressure. The crude oil was purified by flash chromatography using a gradient from 20% to 100% ULTRA solvent in DCM. The desired fractions were combined and concentrated under reduced pressure to yield a light yellow, viscous oil (0.21 g, 33%). $^1H$ NMR (500 MHz, $CDCl_3$) $\delta$ 8.30-7.3 (m, mostly impurity. Includes 2H br s), 5.80-5.70 (m, 4H), 4.90 (dd, 8H), 3.23 (br s, 2H), 2.80-2.20 (m, 22H), 1.98 (q, J=6.7 Hz, 8H), 1.50-1.20 (m, 46H), 0.81 (t, J=7.3 Hz, 3H). $^{13}C$ NMR (500 MHz, $CDCl_3$) $\delta$ 172.74, 139.00, 133.91, 131.53, 128.44, 128.42, 127.23, 127.20, 114.15, 70.24, 67.97, 64.54, 61.38, 57.95, 33.70, 29.60, 29.01, 28.80, 25.63, 25.61, 18.25. MS (DART pos) m/z: $[M+H]^+$ calc'd for $C_{53}H_{101}N_5O_6$, 904.78; found, 904.81.

I-3 (G1-nPr-C7RfE)

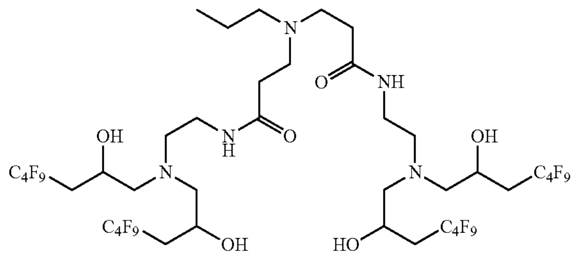

A solution of 2,2,3,3,4,4,5,5,5-Nonafluoropentyloxirane (15 g, 4 eq) in EtOH was added to a solution of Intermediate B (0.4 g, 1 eq) in EtOH in a sealed pressure vessel. The mixtures were stirred at 80° C. for 72 hours. Solvent was removed under reduced pressure. The crude oil was purified by flash chromatography using a gradient from 20% to 100% ULTRA solvent in DCM. The desired fractions were combined and concentrated under reduced pressure to yield a light yellow, viscous oil (0.25 g, 13%). $^1H$ NMR (500 MHz, $CDCl_3$) $\delta$ 7.90-7.35 (m, mostly impurity. Includes 2H br s), 4.35 (p, J=5.5 Hz, <1H), 3.34-3.26 (m, 2H), 2.85-2.00 (m, 55H), 1.55-1.40 (m, 2H), 0.88-0.81 (m, 3H). $^{19}F$ NMR (400 MHz, $CDCl_3$) $\delta$ −81.49 (3F), −112.87 (1.4F), −113.26 (0.4F), −124.87 (2F), 126.26 (2F). MS (MALDI-TOF pos) m/z: $[M+H]^+$ calc'd for $C_{41}H_{49}F_{36}N_5O_6$, 1392.31; found, 1392.3.

Intermediate C

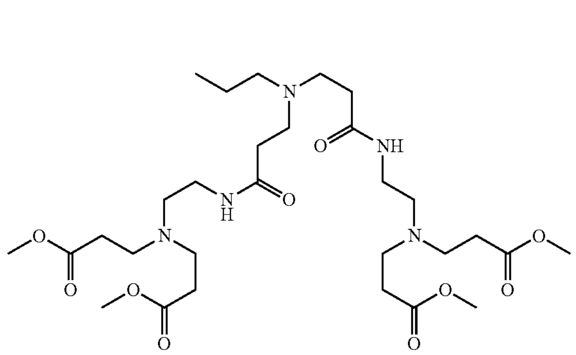

A solution of Intermediate B (2.74 g, 9.53 mmol, 1 eq) in methanol was added dropwise to a solution of methyl acrylate (16.4 g, 190.7 mmol, 20 eq) in methanol. The mixture was stirred for 72 hours at room temperature. Solvent and excess methyl acrylate were removed under reduced pressure. Further purification was carried out by flash chromatography using a gradient from 10% to 50% ULTRA in DCM. Intermediate C was isolated as a light-yellow, clear oil (1.46 g, 24%). $^1H$ NMR (500 MHz, $CDCl_3$) $\delta$ 7.13 (t, J=5.5 Hz, 2H), 3.15 (q, J=5.6 Hz, 4H), 2.63 (t, J=6.8 Hz, 12H), 2.41 (t, J=6.4 Hz, 4H), 2.30 (t, J=6.8 Hz, 1 OH), 2.23 (t, J=6.8 Hz, 4H), 1.33 (sextet, J=7.4 Hz, 2H), 0.73 (t, J=7.3 Hz, 3H). $^{13}C$ NMR (500 MHz, $CDCl_3$) $\delta$ 172.86, 172.18, 55.02, 52.86, 51.46, 49.60, 49.12, 36.93, 33.32, 32.56, 19.83, 11.75. MS (DART pos) m/z: $[M+H]^+$ calc'd for $C_{29}H_{53}N_5O_{10}$, 632.38; found 632.28.

Intermediate D

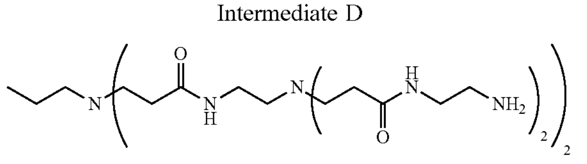

A solution of ethylenediamine (10.6 g, 110.8 mmol, 80 eq) in methanol was added dropwise to a solution of Intermediate C (1.4 g, 2.22 mmol, 1 eq) in methanol. The mixture was stirred for one week at room temperature. Solvent and excess ethylenediamine were removed under reduced pressure to yield Intermediate D (1.88 g, 114%) as a yellow, viscous oil with residual ethylenediamine. $^1H$ NMR (500 MHz, $CDCl_3$) $\delta$ 8.01 (t, J=5.7 Hz, 1H), 7.65 (t, J=5.7 Hz, 2H), 3.25 (q, J=5.8 Hz, 4H), 3.20 (q, J=6.1 Hz, 2H), 2.79 (t, J=5.7 Hz, 3H), 2.74-2.65 (m) 2.50 (t, J=6.2 Hz, 2H), 2.40-2.28 (m, 14H) 1.42 (h, J=7.3 Hz, 1H), 0.83 (t, J=7.3 Hz, 1H). $^{13}C$ NMR (500 MHz, $CDCl_3$) $\delta$ 173.07, 172.88, 55.22, 52.86, 50.60, 50.22, 49.73, 45.78, 44.77, 42.07, 41.42, 37.88, 34.37, 33.60, 19.63, 11.91.

I-4 (G2-nPr-C14E)

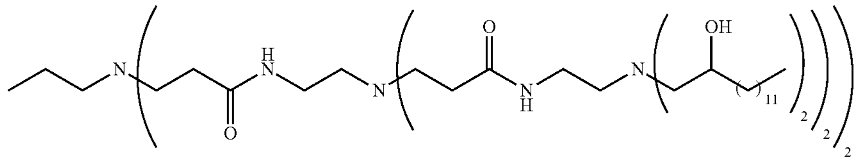

A solution of 1,2-epoxytetradecane (1.14 g, 5.38 mmol, 8 eq) in EtOH was added to a solution of Intermediate D (0.5 g, 0.672 mmol, 1 eq) in EtOH in a sealed pressure vessel. The mixture was stirred at 80° C. for 72 hours. Solvent was removed under reduced pressure. The crude oil was purified by flash chromatography using a gradient from 20% to 50% ULTRA in DCM. The desired fractions were combined, dried over anhydrous salt, and concentrated under reduced pressure to yield an off-white amorphous solid (0.19 g, 12%). $^{1}H$ NMR (500 MHz, $CDCl_3$) δ 8.05-7.80 (m, 2H), 3.30-3.00 (m, 3H), 2.90-2.10 (m, 36H), 1.50-1.00 (m, 198H), 0.82 (t, J=7.0 Hz, 27H). $^{13}C$ NMR (126 MHz, $cdcl_3$) δ 174.94, 173.15, 70.35, 70.32, 69.33, 67.73, 64.62, 64.23, 61.63, 57.81, 56.17, 55.11, 55.06, 47.85, 31.88, 29.88, 29.84, 29.80, 29.75, 29.73, 29.68, 29.67, 29.64, 29.63, 29.57, 29.33, 29.31, 25.79, 25.76, 25.73, 22.64, 18.28, 14.05. MS (ESI pos) m/z: $[M+H]^+$ calc'd for $C_{145}H_{293}N_{13}O_{14}$, 2442.26; found, 2442.26.

I-6 (G2-nPr-C16E)

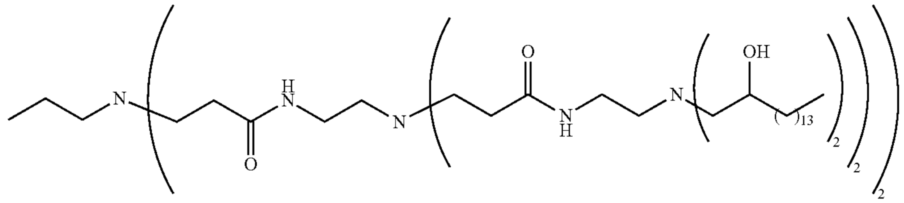

A solution of 1,2-epoxyhexadecane (2.71 g, 11.3 mmol, 10 eq) in EtOH was added to a solution of Intermediate D (0.84 g, 1.13 mmol, 1 eq) in EtOH in a sealed pressure vessel. The mixture was stirred at 80° C. for 72 hours and then extracted with dichloromethane and water. Organic fractions were collected and solvent was removed under reduced pressure to afford a crude product (1.52 g, 50%). $^{1}H$ NMR (500 MHz, $CDCl_3$) δ 7.98 (br s, 3.7H), 3.42 (br s, 3H), 3.35-3.20 (m, 4.2H), 3.00-2.00 (m, 53H), 1.60-1.00 (m, 209H), 0.87 (t, J=7.0 Hz, 27H). $^{13}C$ NMR (500 MHz, CDCl3) δ 172.90, 70.38, 67.73, 64.21, 61.99, 52.63, 52.62, 31.91, 29.71, 29.35, 25.78, 22.67, 14.09. MS (ESI pos) m/z: $[M+H]^+$ calc'd for $C_{161}H_{325}N_{14}O_{14}$, 2666.51; found 2666.51.

I-5 (G2-nPr-C10O1E)

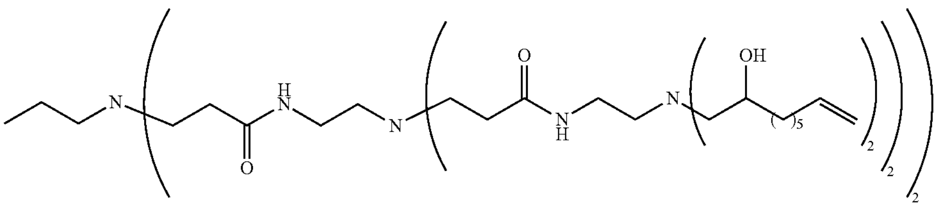

A solution of 1,2-epoxy-9-decene (1.2 g, 12 eq) in EtOH was added to a solution of Intermediate D (0.5 g, 1 eq) in EtOH in a sealed pressure vessel. The mixture was stirred at 80° C. for 72 hours. Solvent was removed under reduced pressure. The crude oil was purified by flash chromatography using a gradient from 20% to 50% ULTRA in DCM. The desired fractions were combined, dried over anhydrous salt, and concentrated under reduced pressure to yield a yellow, viscous oil (0.75 g, 56%). $^1$H NMR (500 MHz, $CDCl_3$) δ 8.10-7.75 (m, 6H), 5.80-5.70 (m, 8H), 4.98-4.86 (m, 16H), 3.56 (br s, 9H), 3.30-3.15 (m, 8H), 2.80-2.20 (m, 53H), 1.99 (q, J=6.7 Hz, 16H), 1.50-1.15 (m, 90H), 0.83 (t, J=7.3 Hz, 3H). $^{13}$C NMR (126 MHz, $CDCl_3$) δ 173.23, 173.17, 139.03, 114.17, 114.16, 70.16, 70.10, 67.96, 67.90, 64.55, 61.84, 56.88, 54.89, 52.55, 50.31, 50.30, 50.20, 49.65, 38.67, 37.49, 35.13, 34.88, 34.85, 33.73, 29.66, 29.64, 29.61, 29.05, 29.04, 29.02, 28.83, 28.81, 25.67, 25.65, 25.63, 19.25, 11.89. MS (ESI pos) m/z: $[M+H]^+$ calc'd for $C_{133}H_{213}N_{13}O_{14}$, 1977.64; found, 1977.64.

Intermediate E

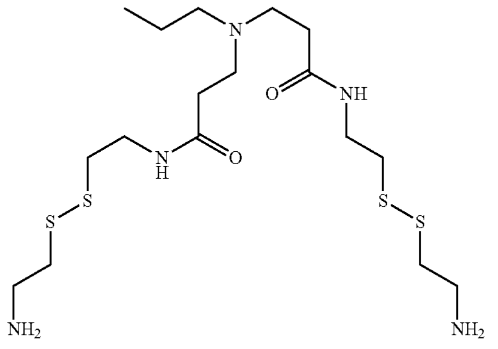 [SMILES: CCCN(CCC(=O)NCCSSCCN)CCC(=O)NCCSSCCN]

A solution of free-base cystamine (20.79 g, 136 mmol, 15 eq) in methanol was added dropwise to a solution of Intermediate A (2.00 g, 8.65 mmol, 1 eq) in methanol. The mixture was stirred for one week at room temperature. Solvent was removed under reduced pressure to yield a crude oil. The crude oil was purified by flash chromatography using an eluent of DCM:MeOH:$NH_4OH$ in a ratio of 70:26:4. The desired fractions were collected, dried over anhydrous $Na_2SO_4$ and concentrated to a light yellow, viscous oil (0.55 g, 13%). $^1$H NMR (500 MHz, $CDCl_3$) δ 7.56 (t, J=5.9 Hz, 2H), 3.52 (q, J=6.1 Hz, 4H), 2.99 (t, J=6.2 Hz, 4H), 2.82-2.73 (m, 8H), 2.71 (t, J=6.5 Hz, 4H), 2.42-2.29 (m, 6H), 1.87 (s, 6H), 1.45 (h, J=7.3 Hz, 2H), 0.85 (t, J=7.4 Hz, 3H). $^{13}$C NMR (126 MHz, $CDCl_3$) δ 172.54, 57.55, 55.04, 49.58, 42.17, 41.98, 40.41, 40.39, 37.96, 37.75, 33.28, 19.69, 18.42, 11.92. MS (DART pos) m/z: $[M+H]^+$ calc'd for $C_{17}H_{37}N_5O_2S_4$, 472.18; found, 472.19.

I-7 (G1-nPr-S8-C14E)

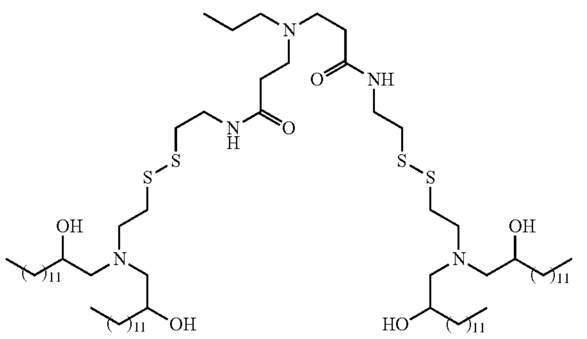

A solution of 1,2-epoxytetradecane (0.67 g, 3.14 mmol, 4 eq) in EtOH was added to a solution of Intermediate E (0.37 g, 0.78 mmol, 1 eq) in EtOH in a sealed pressure vessel. The mixture was stirred at 70° C. for 72 hours. Solvent was removed under reduced pressure. The crude oil was purified by flash chromatography using a gradient from 20% to 40% ULTRA solvent in DCM. The desired fractions were combined and concentrated under reduced pressure to yield a viscous yellow oil (0.15 g, 14.6%). $^1$H NMR (500 MHz, $CDCl_3$) δ 7.64-7.54 (m, 2H), 3.53 (q, J=6.2 Hz, 4H), 3.00-2.25 (m, 30H), 1.52-1.15 (m, 90H), 0.86 (t, J=0.69 Hz, 15H). MS (MALDI-TOF pos) m/z: $[M+H]^+$ calc'd for $C_{73}H_{149}N_5O_6S_4$, 1321.04; found, 1321.2.

Intermediate F

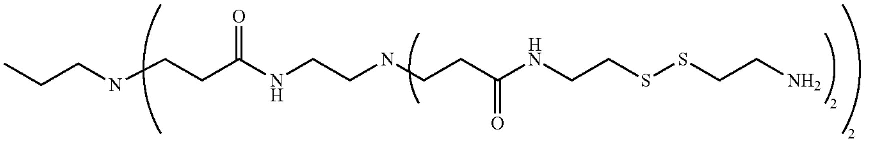

A solution of free-base cystamine (13.2 g, 87 mmol, 39 eq) in methanol was added dropwise to a solution of Intermediate C (1.41 g, 2.23 mmol, 1 eq) in methanol. The mixture was stirred for one week at room temperature. Solvent was removed under reduced pressure to yield a crude oil. The crude oil was purified by precipitation in MeOH/diethyl ether to yield a viscous yellow oil (0.86 g, 0.35%). $^1$H NMR (500 MHz, $CDCl_3$) δ 7.77 (m, 2H), 7.65 (t, J=5.8 Hz, 4H), 3.53 (q, J=6.5 Hz, 8H), 3.24 (m, 4H) 3.05-2.95 (m, 16H), 2.85-2.65 (m, 30H), 2.60-2.25 (m, 15H), 1.65 (br s, 38H), 1.45-1.40 (m, 2H), 0.86 (t, J=7.3 Hz, 3H). MS (ESI pos) m/z: $[M+H]^+$ calc'd for $C_{41}H_{85}N_5O_6S_8$, 1112.45; found, 1112.46.

Using any compound produced using an epoxide ring opening reaction, the —OH group is reduced to a ketone via an oxidation reaction. An example of an oxidizer is Dess-Martin periodinane.

I-22 (G1-nPr-C14)

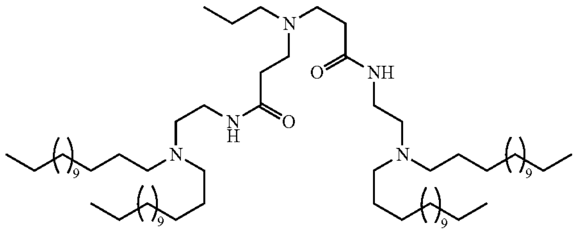

I-24 (G2-nPr-S14-C14E)

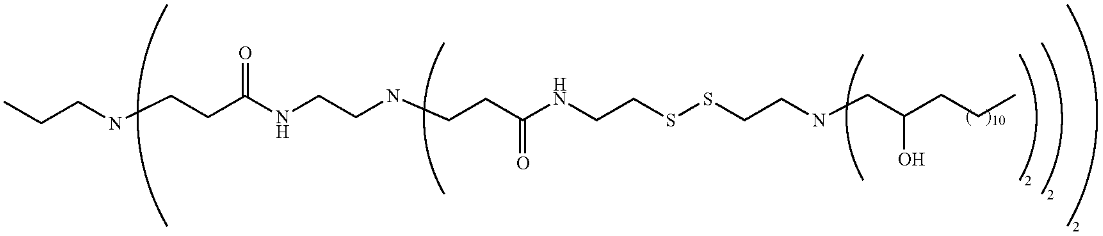

A solution of 1,2-epoxytetradecane (1.97 g, 9.27 mmol, 12 eq) in EtOH was added to a solution of Intermediate F (0.86 g, 0.77 mmol, 1 eq) in EtOH in a sealed pressure vessel. The mixture was stirred at 50° C. for 72 hours. Solvent was removed under reduced pressure. The crude oil was purified by flash chromatography using a gradient of 30 to 50% ULTRA solvent in DCM. The desired fractions were combined and concentrated under reduced pressure to yield a viscous yellow oil (0.36 g, 17%). $^1$H NMR (400 MHz, $CDCl_3$) δ 7.83 (br s, 2H), 7.71 (br s, 4H) 3.63 (m, 8H), 3.51 (m, 8H), 3.24 (m, 4H), 3.10-2.20 (m, 70H), 1.60-1.00 (m, 187H), 0.87 (t, J=7.1 Hz, 1H).

I-15 (G1-nPr-C14K)

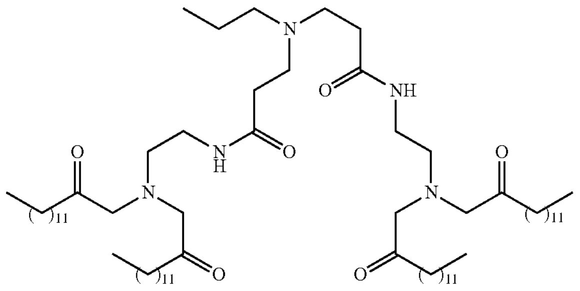

Dess-Martin periodinane (2.545 g, 1.5 eq) was added to a solution of 1-tetradecanol (0.858 g, 1 eq) in DCM (30 mL). The mixture was stirred for 16 hours at room temperature under nitrogen atmosphere. The reaction was quenched upon addition of a 1:1 mixture (100 mL) of saturated aqueous sodium bicarbonate and sodium thiosulfate. The organic phase was then extracted 3 times with diethyl ether (3×40 mL). The combined extracts were washed with water (3×30 mL) and brine (90 mL), dried over sodium sulfate, filtered, and concentrated under reduced pressure. The crude was further purified by flash chromatography using a gradient from 0 to 10% ethyl acetate in hexane. The desired fractions were combined and concentrated under reduced pressure to yield tetradecanal as a white waxy solid. (0.48 g, 57%).

A solution of Intermediate B (0.108 g, 1 eq) in dichloroethane (DCE) (5 mL) was added to tetradecanal (0.48 g, 6 eq) on ice. A solution of sodium triacetoxyborohydride (0.48 g, 6 eq) and glacial acetic acid (0.136 g, 6 eq) in DCE (5 mL) was added to the mixture and the reaction was allowed to return to room temperature. The mixture was stirred for 16 hours at room temperature under nitrogen atmosphere. The reaction was quenched by slowly adding saturated aqueous sodium bicarbonate (50 mL). The organic phase was extracted 4 times with diethyl ether (4×40 mL). The combined extracts were washed with brine (50 mL), dried over sodium sulfate, filtered, and concentrated under reduced pressure. The crude was further purified by flash chromatography using a gradient from 0 to 20% ULTRA solvent in DCM. The desired fractions were combined and concentrated under reduced pressure to yield I-22 (G1-nPr-C14) as a colorless oil. (0.17 g, 45%). $^1$H NMR (500 MHz, CDCL3) δ: 6.98 (t, J=5.2 Hz, 2H), 3.24 (q, J=6.0 Hz, 3H), 2.71 (t, J=6.6 Hz, 3H), 2.50 (t, J=6.3 Hz, 3H), 2.42-2.33 (m, 9H), 2.29 (t, J=6.6 Hz, 4H), 1.47-1.33 (m, 10H), 1.23 (s, 92H), 0.84 (td, J=7.1, 5.5 Hz, 15H). MS (ESI pos) m/z: $[M+H]^+$ calc'd for $C_{69}H_{141}N_5O_2$, 1073.11; found, 1073.11.

I-18 (G1-nPr-amide-t9)

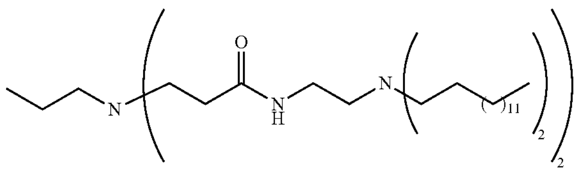

Dess-Martin periodinane (2.545 g, 1.5 eq) was added to a solution of 1-tetradecanol (0.858 g, 1 eq) in DCM (30 mL). The mixture was stirred for 16 hours at room temperature under nitrogen atmosphere. The reaction was quenched upon addition of a 1:1 mixture (100 mL) of saturated aqueous sodium bicarbonate and sodium thiosulfate. The organic phase was then extracted with diethyl ether (3×40 mL). The combined extracts were washed with water (3×30 mL) and brine (90 mL), dried over sodium sulfate, filtered, and concentrated under reduced pressure. The crude was further purified by flash chromatography using a gradient from 0 to 10% ethyl acetate/hexane. The desired fractions were combined and concentrated under reduced pressure to yield tetradecanal as a white waxy solid. (0.48 g, 57%).

Dichloroethane was dried over molecular sieves (Sigma-Aldrich, 3 Å, 8-12 mesh) for 1 week prior to use. A solution of Intermediate B (0.108 g, 0.376 mmol, 1 eq) in dichloroethane (5 mL) was added to tetradecanal (0.48 g, 2.3 mmol, 6 eq) at 0° C. A solution of sodium triacetoxyborohydride (STAB) (0.48 g, 2.3 mmol, 6 eq) and glacial acetic acid (0.136 g, 2.26 mmol, 6 eq) in dichloroethane (5 mL) was added to the mixture and the reaction was returned to room temperature. The mixture was purged with nitrogen, covered with foil, and stirred for 16 hours. The reaction was quenched by slowly adding saturated aqueous sodium bicarbonate (50 mL). The organic phase was extracted with diethyl ether (4×40 mL). The combined extracts were washed with brine (50 mL), dried over sodium sulfate, filtered, and concentrated under reduced pressure. The crude was further purified by flash chromatography using a gradient from 0% to 20% ULTRA/DCM. The desired fractions were combined and concentrated under reduced pressure to a clear, colorless, viscous oil. (0.17 g, 45%). $^1$H NMR (500 MHz, $CDCl_3$) δ 6.98 (t, J=5.2 Hz, 2H), 3.24 (q, J=6.0 Hz, 4H), 2.71 (t, J=6.6 Hz, 4H), 2.50 (t, J=6.3 Hz, 4H), 2.42-2.33 (m, 9H), 2.29 (t, J=6.6 Hz, 4H), 1.47-1.33 (m, 10H), 1.23 (s, 92H), 0.84 (t, J=7.1 Hz, 15H). MS (MALDI-TOF+) m/z: $[M+H]^+$ calc'd for $C_{69}H_{141}N_5O_2$, 1073.11; found, 1073.11.

I-25 (G1-C3-K2-E15)

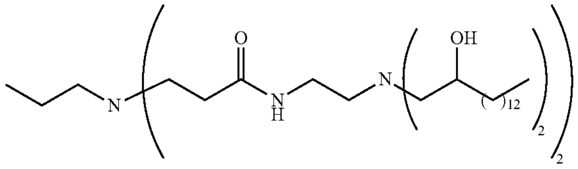

1-pentadecane (0.5 g, 2.37 mmol, 1 eq) was dissolved in dichloromethane (10 mL) added dropwise to a flask containing m-chloroperoxybenzoic acid (1.17 g, 4.75 mmol, 2 eq) dissolved in dichloromethane (10 mL). The reaction was stirred for 18 hr and then quenched with saturated sodium sulfite (40 mL) while stirring. The mixture was transferred to a separatory funnel and extracted with dichloromethane (3×30 mL). The organic fractions were collected and washed with 1 M sodium hydroxide (3×30 mL), brine (1×50 mL), and then dried over anhydrous salt. The organic fractions were concentrated under vacuum to yield 1,2-epoxypentane as a clear colourless oil with minor benzoic acid impurities (0.49 g, 2.16 mmol, 91%). The epoxide was used without further purification. $^1$H NMR (500 MHz, $CDCl_3$) δ 2.86 (tdd, J=5.5, 4.0, 2.7 Hz, 1H), 2.70 (dd, J=5.1, 3.9 Hz, 1H), 2.42 (dd, J=5.1, 2.7 Hz, 1H), 1.52-1.17 (m, 26H), 0.85 (t, J=7.0 Hz, 3H). $^{13}$C NMR (500 MHz, $CDCl_3$) δ 52.37, 47.07, 32.57, 32.00, 29.76, 29.74, 29.73, 29.71, 29.63, 29.52, 29.43, 26.04, 22.75, 14.14.

I-25 (G1-C3-K2-E15) was synthesized analogously to I-1 (G1-nPr-C14E) using 1,2-epoxypentadecane instead of 1,2-epoxytetradecane. The purified compound was a pale yellow, clear, viscous oil (73.9 mg, 0.062 mmol, 11%). $^1$H NMR (500 MHz, $CDCl_3$) δ 7.99-7.90 (m, 1H), 7.87 (t, J=5.6 Hz, 0.5H), 3.63-3.47 (m, 4H), 3.24 (q, J=5.5 Hz, 1H), 2.71 (q, J=6.7 Hz, 5H), 2.66-2.58 (m, 2H), 2.58-2.50 (m, 2H), 2.45-2.23 (m, 9H), 1.52-1.09 (m, 104H), 0.82 (dt, J=11.9, 7.0 Hz, 15H). $^{13}$C NMR (500 MHz, $CDCl_3$) δ 172.91, 172.87, 172.77, 172.50, 70.49, 68.09, 64.77, 61.43, 55.48, 53.36, 49.83, 35.15, 35.02, 34.91, 33.86, 31.88, 29.89, 29.84, 29.81, 29.80, 29.68, 29.63, 29.33, 25.81, 25.72, 22.64, 14.06, 11.82. MS (MALDI-TOF+) m/z: $[M+H]^+$ calc'd for $C_{73}H_{149}N_5O_6$, 1193.15; found, 1193.2.

I-26 (G1-C3-K2-E10)

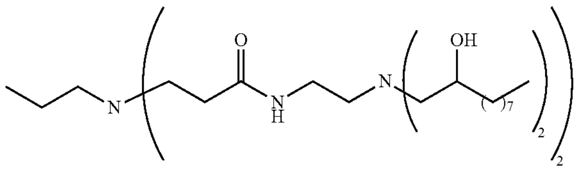

I-26 (G1-C3-K2-E10) was synthesized analogously to I-1 (G1-nPr-C14E) using 1,2-epoxydecane instead of 1,2-epoxytetradecane. The purified compound was a pale yellow, clear, viscous oil (0.5961 g, 0.6533 mmol, 38%). $^1$H NMR (400 MHz, $CDCl_3$) δ 7.99-7.75 (m, 2H), 3.69-3.51 (m, 4H), 3.28 (q, J=5.6 Hz, 2H), 2.82-2.73 (m, 4H), 2.73-2.55 (m, 5H), 2.53-2.26 (m, 13H), 1.57-1.11 (m, 60H), 0.86 (q, J=6.9 Hz, 15H). $^{13}$C NMR (400 MHz, $CDCl_3$) δ 70.81, 68.27, 64.87, 50.16, 35.33, 35.15, 32.02, 29.96, 29.73, 29.44, 25.88, 22.80, 14.23, 11.97. MS (MALDI-TOF+) m/z: $[M]^+$ calc'd for $C_{53}H_{109}N_5O_6$, 912.5; found, 912.8.

Intermediate B'

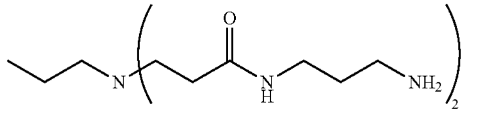

1,3-diaminopropane (9.62 g, 129.7 mmol, 15 eq) was combined with Intermediate A (2.0 g, 8.6 mmol, 1 eq) in methanol (10 mL). The mixture was purged with nitrogen, covered with foil, and stirred for 5 days at room temperature. Consumption of Intermediate A was monitored by TLC (15% MeOH/DCM). Solvent was removed under reduced pressure. The remaining propanediamine was removed by successive washes with 5% methanol in diethyl ether (5×30 mL). Residual solvent was removed under vacuum to yield Intermediate B (0.558 g, 20%) as a clear, colourless, viscous oil. $^1$H NMR (400 MHz, $CDCl_3$) δ 7.72 (t, J=5.8 Hz, 2H), 3.09 (q, J=6.4 Hz, 4H), 2.54 (td, J=6.6, 2.5 Hz, 8H), 2.39 (s, 7H), 2.24-2.18 (m, 1H), 2.14 (t, J=6.5 Hz, 3H), 1.44 (p, J=6.7 Hz, 4H), 1.28 (sextet, J=7.3 Hz, 1H), 0.69 (t, J=7.4 Hz, 3H). $^{13}$C NMR (400 MHz, $CDCl_3$) δ 172.38, 54.89, 49.50, 49.24, 39.08, 36.41, 33.15, 32.38, 19.51, 11.57. MS (DART+) m/z: $[M+H]^+$ calc'd for $C_{15}H_{33}N_5O_2$, 316.26; found, 316.27.

I-27 (G1-C3-K3-E10)

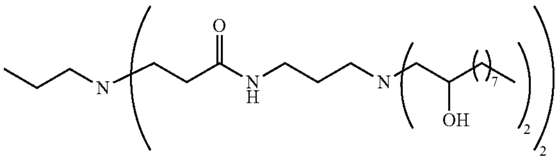

A mixture of 1,2-epoxydecane (0.300 g, 1.92 mmol, 5 eq) and Intermediate B' (0.121 g, 0.38 mmol, 1 eq) were added together in an 8-dram screw-cap vial. The mixture was covered with foil and stirred at 90° C. overnight. Consumption of Intermediate B' was monitored by TLC (35% ULTRA/DCM). The crude oil was purified by flash chromatography using a 50 g silica cartridge and a solvent gradient from 20% ULTRA/DCM to 40% ULTRA/DCM. The desired fractions were combined and concentrated under vacuum to a pale yellow, clear, viscous oil (0.12 g, 34%). $^1$H NMR (400 MHz, $CDCl_3$) δ 7.96-7.84 (m, 2H), 3.71-3.58 (m, 4H), 3.30 (q, J=5.2 Hz, 2H), 3.22-3.10 (m, 1H), 2.77 (q, J=6.8 Hz, 3H), 2.68-2.58 (m, 3H), 2.57-2.16 (m, 13H), 1.63 (p, J=6.3 Hz, 4H), 1.54-1.11 (m, 58H), 0.85 (td, J=7.0, 3.1 Hz, 15H). $^{13}$C NMR (400 MHz, $CDCl_3$) δ 172.34, 70.24, 68.00, 63.19, 60.76, 49.94, 35.43, 35.24, 33.82, 31.94, 29.92, 29.66, 29.36, 25.82, 25.74, 22.72, 14.15, 11.88. MS (ESI+) m/z: $[M+H]^+$ calc'd for $C_{55}H_{113}N_5O_6$, 940.87; found, 940.87.

I-28 (G1-OC2-K3-E10)

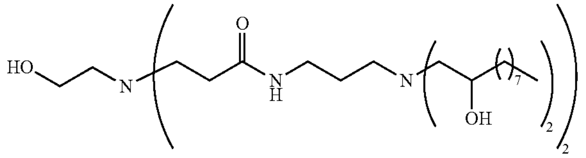

2-amino-1-ethanol (0.916, 15 mmol, 1 eq) was added to a mixture of imidazole (2.042 g, 30 mmol, 2 eq) and tert-butyldimethylsilyl chloride (2.487 g, 16.5 mmo, 1.1 eq) in dichloromethane (50 mL) and stirred for 3 hr at room temperature. The mixture was then diluted with water (60 mL) and extracted with dichloromethane (3×30 mL). The organic fractions were washed with brine (1×50 mL) and then dried over anhydrous salt. The organic fractions were concentrated under vacuum to produce 2-((tert-butyldimethylsilyl)oxy)ethan-1-amine (2.96 g, 112%) and used without further purification. $^1$H NMR (400 MHz, $CDCl_3$) δ 3.58 (t, J=5.3 Hz, 2H), 2.73 (t, 2H), 0.86 (s, 9H), 0.02 (s, 6H).

Intermediate TBS-A'

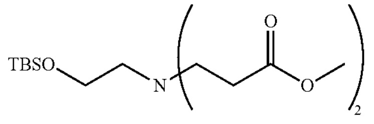

2-amino-1-ethanol (0.916, 15 mmol, 1 eq) was added to a mixture of imidazole (2.042 g, 30 mmol, 2 eq) and tert-butyldimethylsilyl chloride (2.487 g, 16.5 mmo, 1.1 eq) in dichloromethane (50 mL) and stirred for 3 hr at room temperature. The mixture was then diluted with water (60 mL) and extracted with dichloromethane (3×30 mL). The organic fractions were washed with brine (1×50 mL) and then dried over anhydrous salt. The organic fractions were concentrated under vacuum to produce 2-((tert-butyldimethylsilyl)oxy)ethan-1-amine (2.96 g, 112%) and used without further purification. $^1$H NMR (400 MHz, $CDCl_3$) δ 3.58 (t, J=5.3 Hz, 2H), 2.73 (t, 2H), 0.86 (s, 9H), 0.02 (s, 6H).

2-((tert-butyldimethylsilyl)oxy)ethan-1-amine (2.96 g, 16.9 mmol, 1 eq) was combined with methyl acrylate (3.87 g, 45 mmol, 3 eq) in methanol (10 mL). The mixture was purged with nitrogen, covered with foil, and stirred for 3 days at room temperature. Consumption of TBS-A was monitored by TLC (20% MeOH/DCM). Solvent and excess methyl acrylate were removed under vacuum to produce TBS-A as a clear, colourless oil (3.72 g, 71%). $^1$H NMR (400 MHz, $CDCl_3$) δ 3.59 (s, 7H), 2.76 (t, J=7.2 Hz, 4H), 2.53 (t, J=6.4 Hz, 2H), 2.38 (d, J=14.3 Hz, 2H), 0.82 (s, 9H), −0.02 (s, 6H).

Intermediate TBS-B'''

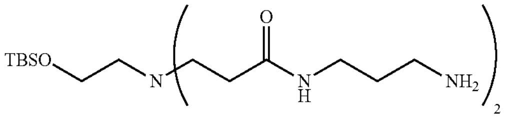

1,3-diaminopropane (6.35 g, 85.6 mmol, 8 eq) was added to a flask containing TBS-A' (3.72 g, 10.7 mmol, 1 eq) dissolved in methanol (10 mL). The flask was purged with nitrogen, covered with foil, and stirred for 5 days. Consumption of TBS-A' was monitored by TLC (15% MeOH/DCM). Solvent was removed under reduced pressure, and the majority of 1,3-diaminopropane was removed by successive washes with 15% ethyl acetate in hexanes (5×20 mL). Residual solvent was removed under vacuum to yield TBS-B''' as a clear, colourless, viscous oil with residual 1,3-diaminopropane impurity (1.59 g, 3.68 mmol, 34%). $^1$H NMR (500 MHz, $CDCl_3$) δ 7.62 (t, J=5.7 Hz, 2H), 3.42 (t, J=6.0 Hz, 2H), 3.02 (q, J=6.6 Hz, 4H), 2.59-2.44 (m, 18H, 1,3-diaminopropane impurity), 2.37 (t, J=6.1 Hz, 2H), 2.12-2.02 (m, 6H), 1.75 (br s, 16H, water), 1.41-1.30 (m, 9H), 0.63 (s, 7H), 0.62 (s, 2H), −0.20 (s, 4H), −0.20 (s, 2H). $^{13}$C NMR (500 MHz, $CDCl_3$) δ 172.02, 60.67, 59.88, 54.93, 50.08, 48.86, 39.37, 39.02, 36.52, 36.26, 33.33, 32.44, 25.45, 20.55, 17.79, 13.71, −5.79.

Intermediate TBS-I-28 (G1-OC2-K3-E10)

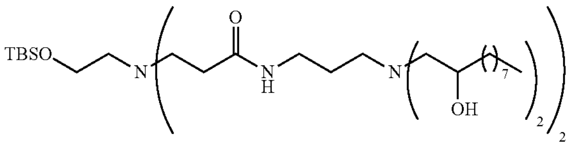

A mixture of 1,2-epoxydecane (2.3 g, 14.7 mmol, 12 eq) and intermediate TBS-B''' (0.53 g, 1.23 mmol, 1 eq) were added together in an 8-dram screw-cap vial. The high number of equivalents of 1,2-epoxydecane was required to alkylate the residual 1,3-diaminopropane, which can they be separated during flash chromatography. The mixture was covered with foil and stirred at 90° C. overnight. The crude oil was purified by flash chromatography using a 50 g silica cartridge and a solvent gradient from 20% ULTRA/DCM to 40% ULTRA/DCM. The desired fractions were combined and concentrated under vacuum to a pale yellow, clear, viscous oil of TBS-I-28 (0.83 g, 0.79 mmol, 64%). $^1$H NMR (500 MHz, $CDCl_3$) δ 7.76-7.67 (m, 2H),), 3.75-3.57 (m, 6H), 3.33-3.25 (m, 2H), 3.23-3.11 (m, 2H), 2.82-2.74 (m, 4H), 2.66-2.58 (m, 4H), 2.51 (dd, J=13.4, 3.1 Hz, 2H), 2.45-2.37 (m, 6H), 2.31 (t, J=6.5 Hz, 4H), 2.23 (dd, J=13.0, 2.3 Hz, 2H), 1.69-1.57 (m, 4H), 1.48-1.18 (m, 66H), 0.86 (t, J=6.9 Hz, 24H), 0.04 (s, 6H). $^{13}$C NMR (500 MHz, $CDCl_3$) δ 172.60, 172.56, 70.28, 68.00, 63.17, 60.86, 60.83, 60.78, 55.96, 55.16, 55.09, 53.75, 53.47, 50.65, 50.61, 50.59, 50.56, 38.05, 37.89, 37.85, 35.40, 35.20, 34.35, 34.32, 34.16, 31.95, 29.92, 29.66, 29.37, 27.17, 26.58, 25.99, 25.83, 25.77, 22.73, 18.33, 14.16, −5.24. MS (DART+) m/z: [M+H]+ calc'd for $C_{60}H_{125}N_5O_7Si$, 1056.93; found, 1056.95.

I-28 (G1-OC2-K3-E10)

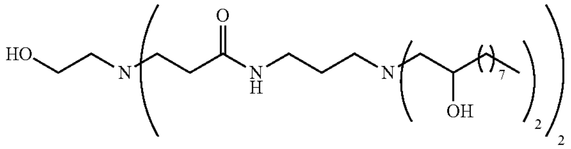

Then, TBS-I-28 (0.830 g, 0.785 mmol, 1 eq) was dissolved in diethyl ether (50 mL) was cooled to 0° C. and a solution of tetra-n-butylammonium fluoride (TBAF) (3.14 mL, 3.14 mmol, 4 eq) was added. The reaction mixture was returned to room temperature, covered with foil, and stirred for 18 hours. Consumption of the TBS protected material was monitored by TLC (35% ULTRA/DCM). The organic fractions were washed with 20% 1 M sodium hydroxide in saturated ammonium chloride (5×15 mL) and brine (1×50 mL), and then dried over anhydrous salt. The organic fractions were concentrated to a crude oil and purified by flash chromatography using a 50 g silica cartridge and a solvent gradient from 20% ULTRA/DCM to 50% ULTRA/DCM. The desired fractions were collected and concentrated under vacuum to yield a clear, colourless, viscous oil of 16 (0.20 g, 0.21 mmol, 27%). $^1$H NMR (500 MHz, $CDCl_3$) δ 7.97-7.85 (m, 2H), 4.46 (s, 6H), 3.69-3.50 (m, 9H), 3.35-3.24 (m, 3H), 3.08-2.93 (m, 1H), 2.74-2.13 (m, 20H), 1.71-1.54 (m, 4H), 1.45-1.17 (m, 73H), 0.85 (t, J=6.8 Hz, 15H). $^{13}$C NMR (500 MHz, $CDCl_3$) δ 172.96, 172.76, 172.72, 70.58, 70.47, 68.13, 68.06, 63.18, 60.66, 58.51, 56.22, 55.98, 55.61, 55.37, 53.62, 49.62, 49.49, 49.44, 39.24, 38.95, 38.53, 38.26, 35.39, 35.22, 34.57, 34.35, 31.91, 29.86, 29.61, 29.32, 26.94, 26.86, 26.08, 25.77, 25.70, 22.69, 20.71, 14.14. MS (ESI+) m/z: $[M+H]^+$ calc'd for $C_{54}H_{111}N_5O_7$, 942.85; found, 942.85.

Intermediate TBS-A

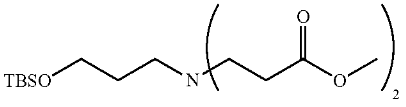

Intermediate TBS-A was synthesized analogously to intermediate TBS-A' using 3-amino-1-propanol instead of 2-amino-1-ethanol. The compound was a clear, colourless oil (2.38 g, 6.58 mmol, 80%). $^1$H NMR (400 MHz, $CDCl_3$) δ 3.61 (s, 6H), 2.71 (t, J=7.2 Hz, 5H), 2.45 (t, J=7.3 Hz, 2H), 2.40 (t, J=7.2 Hz, 4H), 1.58 (p, J=6.3 Hz, 2H), 0.84 (s, 9H), −0.01 (s, 6H). $^{13}$C NMR (400 MHz, $CDCl_3$) δ 173.11, 61.02, 51.53, 50.28, 49.37, 32.58, 30.33, 25.98, 18.32, −3.52, −5.30.

Intermediate TBS-B

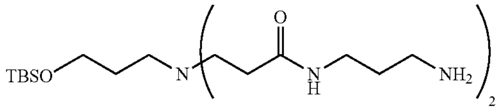

Intermediate TBS-B was synthesized analogously to intermediate TBS-A'. The compound was a clear, colourless, viscous oil with residual 1,3-diaminopropane impurity (0.52 g, 1.16 mmol, 38%). $^1$H NMR (400 MHz, $CDCl_3$) δ 7.36 (t, J=5.7 Hz, 2H), 3.58 (t, J=5.9 Hz, 2H), 3.26 (q, J=6.4 Hz, 4H), 2.72 (q, J=6.8 Hz, 8H), 2.66 (t, J=6.4 Hz, 4H), 2.48 (t, J=6.9 Hz, 2H), 2.27 (t, J=6.3 Hz, 4H), 1.57 (p, J=6.7 Hz, 6H), 0.85 (s, 9H), 0.01 (s, 6H). $^{13}$C NMR (400 MHz, $CDCl_3$) δ 172.46, 60.71, 50.12, 49.46, 39.94, 39.80, 37.31, 37.15, 34.06, 32.79, 29.79, 25.92, 18.22, −5.22.

Intermediate TBS-1-29

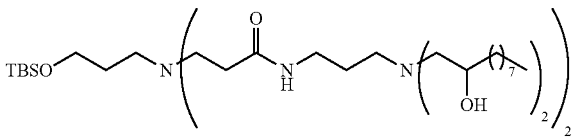

Intermediate TBS-I-29 was synthesized analogously to intermediate TBS-I-28. The purified compound was a pale yellow, clear, viscous oil (0.25 g, 0.23 mmol, 40%). $^1H$ NMR (500 MHz, $CDCl_3$) δ 7.70-7.58 (m, 2H), 3.66-3.54 (m, 7H), 3.26 (q, J=6.1 Hz, 2H), 2.72-2.55 (m, 7H), 2.53-2.45 (m, 6H), 2.44-2.35 (m, 6H), 2.31-2.24 (m, 5H), 2.21 (dt, J=13.0, 2.6 Hz, 2H), 1.69-1.51 (m, 8H), 1.47-1.14 (m, 64H), 0.87-0.82 (m, 2H), 0.01 (t, J=1.0 Hz, 6H). $^{13}C$ NMR (500 MHz, $CDCl_3$) δ 172.62, 70.15, 67.87, 63.10, 60.80, 53.39, 49.97, 35.31, 35.09, 31.86, 29.84, 29.58, 29.28, 25.90, 25.75, 25.68, 22.63, 18.18, 14.06, −5.23.

I-29 (G1-OC3-K3-E10)

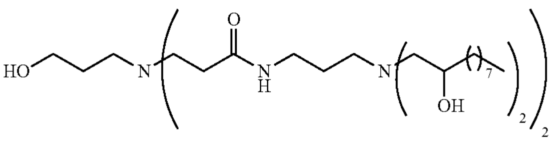

Intermediate TBS-I-29 was deprotected analogously to intermediate TBS-I-29 to yield 1-29. The purified compound was a clear, colourless, viscous oil (0.080 g, 0.084 mmol, 35%). $^1H$ NMR (500 MHz, $CDCl_3$) δ 7.94-7.74 (m, 2H), 4.49 (br s, 7H), 3.72-3.62 (m, 7H), 3.57-3.45 (m, 1H), 3.38-3.24 (m, 2H), 3.16-3.04 (m, 1H), 2.79-2.66 (m, 4H), 2.62 (t, J=6.0 Hz, 2H), 2.58-2.42 (m, 6H), 2.41-2.30 (m, 4H), 2.25 (dt, J=13.0, 2.6 Hz, 2H), 1.74-1.60 (m, 8H), 1.47-1.18 (m, 75H), 0.86 (t, J=6.9 Hz, 12H). $^{13}C$ NMR (500 MHz, $CDCl_3$) δ 172.28, 70.22, 70.09, 67.96, 62.99, 60.70, 55.82, 55.69, 54.52, 53.58, 50.55, 38.69, 38.60, 38.19, 38.08, 35.47, 35.25, 34.51, 34.40, 34.26, 31.95, 29.90, 29.65, 29.37, 28.05, 26.70, 26.20, 25.78, 25.72, 22.73, 20.38, 14.17, 13.74. MS (DART+) m/z: [M+H]+ calc'd for $C_{55}H_{113}N_5O_7$, 956.86; found, 956.88.

Example 2: Synthesis of Multiplexed RNA Nanoparticles

Prior to formulation of RNA nanoparticles, surfaces were sterilized. Glassware and stir bars undergo endotoxin bake at 250° C. for 2-24 hours followed by a NaOH rinse with 10N NaOH. The glassware was then covered with foil to ensure sterility prior to use. The appropriate amounts of materials can be prepared with an excess of 25% to account for material loss prior to formulation. Dialysis cassettes were presoaked in 1× phosphate buffered saline (PBS) prior to the addition of material.

Materials such as PEG-lipid were in solution with EtOH and vortexed prior to use. In accordance with the formula sheet, appropriate amounts of EtOH, PAMAM dendron macromolecule, PEG-lipid, and any further excipients were added to a 1.5 mL Eppendorf tube, in that order. The delivery material underwent brief sonication and slightly warmed if necessary to eliminate precipitate. Similarly, in a biosafety cabinet (BSC), appropriate volumes of citrate buffer, ultra-pure water and the selected RNA were added to a 1.5 mL Eppendorf tube, in that order.

Sterile gastight glass syringes with 10 cm of inlet and 10 cm of outlet Zeus tubing were rinsed with 70% ethanol prior to being loaded. The syringe designated to hold the RNA material underwent an additional citrate buffer rinse. The delivery material and RNA material were loaded into their respective syringes. After ensuring that there were no air bubbles and that tubing is primed, the two syringes were loaded into a syringe pump, and all tubing is attached to a microfluid chip.

Furthermore, the outlet tubing was attached into the dialysis device. Appropriate settings were set on the syringe pump and syringe pumps were started simultaneously. When stopped, tubing was removed from the dialysis device and the combined materials were left to dialyze in 1×PBS buffer to return nanoparticles to neutral pH of 7.4. Nanoparticles were removed from dialysis device after an appropriate amount of time, with a syringe and needle and added to an Eppendorf tube and stored at ambient temperature. Particles can safely be stored at room temperature or −20 C for at least 48 hours without any noticeable changes.

Formulations were completed at in 10 mM to 95 mM citrate buffer pH 3.0, 5.0, or 6.0. Total volumetric flowrate of the nucleic acid and delivery material streams ranged from approximately 1 mL/min to 7.5 ml/min flowing at a 1:1, 2.5:1 and 5:1 ratio of aqueous to organic phase volume. The final RNA nanoparticle was formulated at a 5:1 to 25:1 mass ratio of dendron-to-RNA.

These nanoparticles were characterized with dynamic light scattering (DLS) to demonstrate successful formulation.

The following nanoparticles in the below table 1 were made in a similar fashion. ID indicates the identification number of the nanoparticle formulation. siRNA is small interfering RNA. LNC RNA is long noncoding RNA. Fip-mKate2 plasmid is a DNA plasmid. Rluc IVT RNA is an mRNA lacking a 5' cap and poly-A tail. 14:0 PEG2000 PE is 1,2-dimyristoyl-sn-glycero-3-phosphoethanolamine-N-[methoxy(polyethylene glycol)-2000] where 14:0 can be replaced by 18:0 and 2000 can be replaced by 5000. 18:1 PEG2000 PE is 1,2-dioleoyl-sn-glycero-3-phosphoethanolamine-N-[methoxy(polyethylene glycol)-2000] where 2000 can be replaced by 5000. DMG-PEG2000 is 1,2-dimyristoyl-rac-glycero-3-methoxypolyethylene glycol-2000. DSG-PEG2000 is distearoyl-rac-glycerol-PEG2K, DSPC is 1,2-distearoyl-sn-glycero-3-phosphocholine. Cas9 IVT is an mRNA lacking a 5' cap and poly-A tail. Rluc and Fluc are Renilla luciferase mRNA and Firefly luciferase mRNA, respectively.

TABLE 1

| | Components | | | | | Characterization | | | | |
|---|---|---|---|---|---|---|---|---|---|---|
| ID # | Nano material | Nucleic Acid Payload (molar ratio) | Lipid-PEG (N:M PEG Y N = lipid carbon length; M = unsaturated bond location in lipid section; Y = number of repeat units) | Excipients | pH during formulation | Nano particle size distribution mean diameter (nm) | Poly-dispersity index | Encapsulation efficiency (%) | Mass ratio of delivery components to nucleic acids | Molar Ratios of all Delivery Components (Nano material/ Cholesterol/ DS PC/lipid-PEG) (mol %) |
| AM 01 | I-1 (G1-nPr-C14E) | siRNA + LNC RNA (1:1) | 14:0 PEG2000 PE | N/A | 3 | 190 | 0.046 | | 5:1 | 96.6/0/0/3.4 |
| AM 02 | I-1 (G1-nPr-C14E) | siRNA + LNC RNA (1:1) | 18:0 PEG2000 PE | N/A | 3 | 160.4 | 0.066 | | 5:1 | 96.5/0/0/3.5 |
| AM 03 | I-1 (G1-nPr-C14E) | LNC RNA | 18:0 PEG2000 PE | N/A | 6 | 254.5 | 0.094 | | 5:1 | 97/0/0/3 |
| AM 04 | I-1 (G1-nPr-C14E) | siRNA + LNC RNA (1:1) | 18:1 PEG2000 PE | N/A | 3 | 154.1 | 0.194 | | 5:1 | 92/0/0/8 |
| AM 06 | I-1 (G1-nPr-C14E) | siRNA | 14:0 PEG2000 PE | N/A | 3 | 152 | 0.065 | 83 | 5:1 | 96.5/0/0/3.5 |
| AM 08 | I-1 (G1-nPr-C14E) | siRNA | 18:0 PEG2000 PE | N/A | 3 | 146 | 0.102 | 69 | 5:1 | 96.5/0/0/3.5 |
| AM 10 | I-1 (G1-nPr-C14E) | siRNA | 18:1 PEG2000 PE | N/A | 5 | 272.9 | 0.03 | 68 | 10:1 | 96.5/0/0/3.5 |
| AM 15 | I-3 (G1-nPr-C7RfE) | siRNA | 18:0 PEG2000 PE | N/A | 5 | 104.4 | 0.275 | | 5:1 | 96%/0/0/4 |
| AM 16 | I-3 (G1-nPr-C7RfE) | siRNA | 18:1 PEG2000 PE | N/A | 5 | 131.4 | 0.276 | | 5:1 | 96/0/0/4 |
| AM 17 | I-3 (G1-nPr-C7RfE) | No nucleic acid | 18:0 PEG2000 PE | V/A | 5 | 171.6 | 0.154 | | 5:1 | 96/0/0/4 |
| AM 21 | I-1 (G1-nPr-C14E) | siRNA | 14:0 PEG2000 PE | N/A | 5 | 190 | 0.002 | 89 | 5:1 | 96.5/0/0/3.5 |
| AM 23 | I-2 (G1-nPr-C10O1 E) | siRNA | 14:0 PEG2000 PE | N/A | 5 | 257.7 | 0.05 | | 5:1 | 97.5/0/0/2.5 |
| AM 25 | I-7 (G1-nPr-S8-C14E) | siRNA | 14:0 PEG2000 PE | N/A | 3 | 124.9 | 0.0687 | | 5:1 | 96/0/0/4 |
| AM 31 | I-5 (G2-nPr-C10o1E) | siRNA | 14:0 PEG2000 PE | N/A | 3 | 217 | 0.103 | | 5:1 | 94/0/0/6 |
| AM 33 | I-1 (G1-nPr-C14E) | Fip-mKate2 plasmid | 14:0 PEG2000 PE | N/A | 4 | 141.9 | 0.093 | | 10:1 | 96.5/0/0/3.5 |

TABLE 1-continued

| | Components | | | | Characterization | | | | | |
|---|---|---|---|---|---|---|---|---|---|---|
| ID # | Nano material | Nucleic Acid Payload (molar ratio) | Lipid-PEG (N:M PEG Y N = lipid carbon length; M = unsaturated bond location in lipid section; Y = number of repeat units) | Excipients | pH during formulation | Nano particle size distribution mean diameter (nm) | Poly-dispersity index | Encapsulation efficiency (%) | Mass ratio of delivery components to nucleic acids | Molar Ratios of all Delivery Components (Nano material/ Cholesterol/ DS PC/lipid-PEG) (mol %) |
| AM 38 | I-5 (G2-nPr-C10O1E) | siRNA | 18:0 PEG5000 PE | N/A | 3 | 103.1 | 0.13 | | 5:1 | 98.5/0/0/1.5 |
| AM 39 | I-5 (G2-nPr-C10O1E) | siRNA | 18:1 PEG5000 PE | N/A | 3 | 78.7 | 0.14 | | 5:1 | 98.5/0/0/1.5 |
| AM 40 | I-5 (G2-nPr-C10O1E) | siRNA | 14:0 PEG2000 PE | N/A | 3 | 117.3 | 0.058 | | 5:1 | 98.5/0/0/1.5 |
| AM 44 | 1-4 (G2 nPr-C14E) | siRNA | 14:0 PEG2000 PE | N/A | 3 | 128 | 0.033 | 97 | 5:1 | 98.5/0/0/1.5 |
| AM 51 | I-1 (G1-nPr-C14E) + I-4 (G2-nPr-C14E) | Rluc IVT RNA | 14:0 PEG2000 PE | N/A | 3 | 95.93 | 0.108 | 97 | 10:1 | 98.5/0/0/1.5 |
| AM 52 | I-1 (G1-nPr-C14E) + I-4 (G2 nPr-C14E) | Rluc IVT RNA + sgRNA (1:1) | 14:0 PEG2000 PE | N/A | 3 | 144.3 | 0.168 | 98 | 10:1 | 98.5/0/0/1.5 |
| GT 01 | I-5 (G2-nPr-C10O1E) | siRNA | 14:0 PEG2000 PE | N/A | 3 | 138 | 0.062 | 98 | 5:1 | 98.5/0/0/1.5 |
| JCS 13 | I-1 (G1-nPr-C14E) | Rluc RNA | DSG-PEG2000 | Cholesterol + DSPC | 3 | 147.5 | 0.125 | 88 | 14.5:1 | 50/38.5/10/ 1.5 |
| JCS 16 | I-1 (G1-nPr-C14E) | Fluc mRNA | DMG-PEG2000 | Cholesterol + DSPC | 3 | 165 | 0.015 | 93 | 19:1 | 50/38.5/10/ 1.5 |
| AL10 | I-1 (G1-nPr-C14E) + I-4 (G2-nPr-C14E) | Cas9 IVT RNA + sgRNA (19.37: 80.63) | 14:0 PEG2000 PE | N/A | 3 | 118.33 | 0.080 | 97 | 16.5 | 98.5/1.5 |
| AL13 | I-1 (G1-nPr-C14E0 | Cas9 IVT RNA + sgRNA (19.37: 80.63) | DMG-PEG2000 | Cholesterol + DSPC | 3 | 140.93 | 0.192 | 94 | 19:1 | 50/38.5/10/ 1.5 |
| AM 62 | I-23 (G1-nPr-C16E) | siRNA | 14:0 PEG2000 PE | N/A | 3 | 158 | 0.064 | 83 | 5:1 | 98.5/0/0/1.5 |

TABLE 1-continued

| | Components | | | | | Characterization | | | | |
|---|---|---|---|---|---|---|---|---|---|---|
| ID # | Nano material | Nucleic Acid Payload (molar ratio) | Lipid-PEG (N:M PEG Y N = lipid carbon length; M = unsaturated bond location in lipid section; Y = number of repeat units) | Excipients | pH during formulation | Nano particle size distribution mean diameter (nm) | Poly-dispersity index | Encapsulation efficiency (%) | Mass ratio of delivery components to nucleic acids | Molar Ratios of all Delivery Components (Nano material/ Cholesterol/ DS PC/lipid-PEG) (mol %) |
| AM 64 | I-2 (G1-nPr-C10O1E) | siRNA | 14:0 PEG2000 PE | N/A | 3 | 144.8 | 0.081 | 81 | 5:1 | 98.5/0/0/1.5 |
| 65 | I-7 (G1-nPr-S8-C14E) | siRNA | 14:0 PEG2000 PE | N/A | 3 | 188.5 | 0.16 | 81 | 5:1 | 98.5/0/0/1.5 |

Example 3: RNA Encapsulation Efficiency Assay

Three different nanoparticles were formulated at pH 3.0 with I-1 (G1-nPr-C14E), 25 bp siRNA, and a PEG-lipid excipient. The PEG-lipid excipient was one of 14:0 PEG2000 PE, 18:0 PEG2000 PE, or 18:1 PEG2000 P E. The nanomaterial-to-RNA mass ratio was 5:1 and the nanomaterial-to-PEG molar ratio was 96.5:3.5. This assay was performed in triplicates in a 96-well plate. Briefly, particles were diluted (1:25) in TE buffer or water and treated with 1% TritonX for 10 minutes at 37° C. to disrupt the self-assembly. A siRNA standard curve was prepared to interpolate concentration. Shortly after the addition of the RiboGreen reagent, fluorescence intensity was measured with a Tecan Infinite M200 plate reader (excitation=480 nm, emission=525 nm, integration time=40 μs).

RNA concentration and RNA encapsulation efficiency of the I-1 (G1-nPr-C14E) nanoparticle of the current application was quantified using a modified Quant-iT RiboGreen assay (Walsh C et al., Microfluidic-based manufacture of siRNA-lipid nanoparticles for therapeutic applications. Methods Mol Biol. 2014; 1141:109-20).

Example 4: Functional Delivery of siRNA to Cells In Vitro

I-1 (G1-nPr-C14E) Nanoparticles Delivering GFP siRNA Reducing GFP Expression in HEK293-GFP Cells Nanoparticles were formulated in a 10 mM citrate buffer pH 3 with I-1 (G1-nPr-C14E), PEG-Lipid, and siRNA against green fluorescent protein (GFP). The nanomaterial-to-RNA mass ratio was 5:1. The nanomaterial-to-PEG molar ratio was 96.5:3.5. The in vitro delivery of siRNA to cells was assessed by treating green fluorescent protein (GFP)-positive human embryonic kidney cells (HEK293-GFP & RFP, GenTarget Inc.).

Cells were plated at a density of approximately 14000 cells per well in a black 96-well plate and incubated at 37° C. with 5% $CO_2$ overnight. Subsequently, I-1 (G1-nPr-C14E) formulated with 14:0 PEG2000 PE or 18:0 PEG2000 PE with or without GFP siRNA (Invitrogen) was added to cells along with PBS control. After 48 hours, Hoechst stain was added to the treated cells in the 96-well plate for 15 minutes. The 96-well plate was then briefly centrifuged. The Hoechst-containing media was removed, and cells were resuspended in PBS. The GFP and Hoechst fluorescent intensity is quantified using a plate reader.

The I-1 (G1-nPr-C14E) and 14:0 PEG2000 PE nanoparticle carrying GFP siRNA, and the I-1 (G1-nPr-C14E) and 18:0 PEG2000 PE nanoparticle carrying GFP siRNA both reduced GFP levels after 48 hours, in comparison to their respective nanoparticles without siRNA, and PBS treatment. The mean fluorescent intensity (MFI) is normalized against Hoechst and PBS-treated control (n=3).

TABLE 2

| Treatment | Nucleic acid | Normalized MFI | Standard Deviation |
|---|---|---|---|
| PBS (Negative Control) | None | 1.00 | 0.25 |
| I-1 (G1-nPr-C14E)/14:0 PEG2000 PE | None | 1.14 | 0.24 |
| I-1 (G1-nPr-C14E)/14:0 PEG2000 PE | GFP siRNA | 0.47 | 0.34 |
| I-1 (G1-nPr-C14E)/18:0 PEG2000 PE | None | 0.89 | 0.12 |
| I-1 (G1-nPr-C14E)/18:0 PEG2000 PE | GFP siRNA | 0.67 | 0.07 |

Example 5: Functional Delivery of mRNA to Cells In Vitro

LNPs were formulated with I-1 (G1-nPr-C14E), Cholesterol, DSPC, DSG-PEG 2000 (50/38.5/10/1.5 mol %) and Renilla Luciferase (RLuc) mRNA. Briefly, 300'000 human embryonic kidney cells (HEK293) were transfected in a 24-well plate with 1 μg of mRNA. 24 hours post-transfection, cells were lysed and treated according to the Renilla Luciferase Assay System (Promega). Relative luminescence units (RLU) were determined with a TECAN Infinite M200 plate reader (n=3).

I-1 (G1-n Pr-C14E)/Cholesterol/DSPC/DSG-PEG 2000 nanoparticles significantly increased RLuc expression in HEK293 cells in comparison to a commercially available transfection reagent, Lipofectamine MessengerMax (Invitrogen):

TABLE 3

| Treatment | Mean RLU | Standard Deviation |
|---|---|---|
| PBS (Negative Control) | 199 | 24 |
| Lipofectamine MessengerMax | 47139 | 2975 |
| I-1 (G1-nPr-C14E)/Cholesterol/DSPC/DSG-PEG2000 | 2525798 | 85658 |

In another experiment, cells were treated in a similar way with nanoparticles formulated with I-1 (G1-nPr-C14E), 14:0 PEG2000 PE (96.5/3.5 mol %) and RLuc mRNA.

I-1 (G1-nPr-C14E)/14:0 PEG2000 PE nanoparticles significantly increased relative luminescence units (RLU) in comparison to PBS treated cells. This suggests that I-1 (G1-nPr-C14E)/14:0 PEG2000 PE particles can transfect cells without the need for helper lipids. The table 4 below shows the RLuc expression of 24-hours post-transfection:

TABLE 4

| Treatment | Mean RLU | Standard Deviation |
|---|---|---|
| PBS (Negative Control) | 104 | 10 |
| I-1 (G1-nPr-C14E)/14:0 PEG2000 PE | 123892 | 5603 |

Example 6: Effect of Formulation pH on RNA Release

The formulation pH of nanoparticles containing I-1 (G1-nP4-C14E) and 14:0 PEG2000 PE affects the stability of the particle in basic conditions. The Ribogreen Assay (ThermoFisher) is a common method used to determine the encapsulation efficiency of LNPs. The assay is typically performed in TE buffer (pH 8.0) and the particles are disrupted upon the addition of 1% TritonX to determine RNA entrapment. The encapsulation efficiency of particles formulated in 10 mM citrate buffer pH 5.0 cannot be determined in TE buffer as particles are disrupted without the presence of TritonX. It has been discovered that water can be used instead of TE buffer to accurately determine encapsulation efficiency as water does not disrupt the particles. Interestingly, nanoparticles formulated with 10 mM citrate buffer pH 3.0 can be assayed in both TE buffer and water.

TABLE 5

| | pH 3 | | pH 5 | |
|---|---|---|---|---|
| | EE | Standard Deviation | EE | Standard Deviation |
| TE Buffer | 0.70996 | 0.080723 | 0.119281 | 0.012121 |
| Water | 0.831935 | 0.053595 | 0.885682 | 0.069516 |

Example 7: In Vivo Expression of Firefly Luciferase mRNA

LNPs were formulated with I-1 (G1-nPr-C14E), Cholesterol, DSPC, DMG-PEG 2000 (50/38.5/10/1.5 mol %) and Firefly Luciferase (FLuc) mRNA from Trilink Biotechnologies (L-7202).

In one experiment, 9-10 weeks old C57BL/6 mice (n=3) were injected intravenously with LNPs at 0.4 mg/kg. Total flux is photons per second (p/s) and negative controls are phosphate buffered saline (PBS).

TABLE 6

| | Total Flux (p/s) | |
|---|---|---|
| | I-1 (G1-nPr-C14E)/Cholesterol/DSPC/DMG-PEG2000 | PBS (negative control) |
| Liver | 1.16E+09 | 4.74E+03 |
| Spleen | 6.81E+07 | 1.79E+03 |
| Kidneys | 1.36E+06 | 8.25E+02 |
| Lungs | 7.62E+06 | 4.39E+03 |
| Hind limb | 2.21E+06 | 1.21E+04 |
| Heart | 3.89E+05 | 3.65E−01 |

In another experiment, a 10-week-old C57BL/6 mouse (n=1) was injected intramuscularly with the same LNPs at 0.01 mg/kg. Total flux is photons per second (p/s) and negative control is phosphate buffered saline (PBS).

TABLE 7

| | Total Flux (p/s) | |
|---|---|---|
| | I-1 (G1-nPr-C14E)/Cholesterol/DSPC/DMG-PEG2000 | PBS (negative control) |
| Muscle | 5.37E+06 | 1.77E+04 |

6 hours post-injection, all mice were injected with D-Luciferin (150 mg/kg, intraperitoneal). Firefly luciferase emits bioluminescence in the presence of the substrate. The organs were harvested within 10-15 minutes and luminescence was detected using an IVIS Lumina system (Perkin Elmer).

Mice injected intravenously expressed luciferase in the liver, spleen, lungs, kidney, heart, and bone. The mouse injected intramuscularly expressed luciferase at the injection site and at the draining lymph node.

Example 8: Ionizable Lipid Structures (LNP)

Materials and Methods

General Lipid Synthesis

All chemicals and solvents were obtained commercially and used as received unless noted otherwise. Purification was carried out by flash chromatography (Buchi Pure C-815 Flash Chromatography System, ELSD detector) on normal-phase silica gel (Silica Gel, 230-400 Mesh, Grade 60, Fisher Chemical) columns packed by hand in reusable cartridges (Biotage Sfar DLV). Flash chromatography used ULTRA as the polar solvent (mixture of DCM:MeOH:$NH_4OH$ (30% in $H_2O$) at a 75:22:3 volumetric ratio). Reactions were monitored by thin-layer chromatography (Supelco TLC Silica Gel 60 $F_{254}$) and visualized using an iodine-on-silica stain.

All ionizable lipids were synthesized by the methods as shown in Scheme 1 Detailed synthesis methods and molecular characterization are described in example 1.

Firefly Luciferase mRNA Synthesis

A firefly luciferase DNA template was ordered as a custom gene from Integrated DNA Technologies containing the T7 promoter, a minimal 5' untranslated region, and a 3' untranslated region derived from the mouse alpha globin sequence (Table 8) [Trepotec, Z. et al., Maximizing the Translational Yield of mRNA Therapeutics by Minimizing 5'-UTRs, *Tissue Eng. Part A* 25, 69-79, 2019]. In vitro transcription of the DNA template was performed using the HiScribe T7 kit (NEB). Modified mRNA was generated by full substitution of uridine with $N^1$-methyl-pseudouridine-5'-triphosphate (Trilink Biotechnologies). RNA was capped with a cap-1 structure using the vaccinia system and 2'-O-methyltransferase (NEB), and a ~100 nucleotides (nt) poly (A) tail was added enzymatically (NEB). The resulting mRNA was purified by silica-column chromatography. Concentrations were measured using a Nanodrop, and purity was determined by gel electrophoresis.

TABLE 8

Oligonucleotides for Firefly Luciferase DNA Template.

| Name | DNA Sequence (5' to 3') |
|---|---|
| Firefly Luciferase DNA Template | TAGAAACTGGGCTTGTCGAGACTAATACGACTCACTATAGGGAGACTG<br>CCACCATGGAAGACGCGAAGAATATCAAGAAGGGACCTGCACCCTTC<br>TATCCACTGGAAGACGGCACTGCTGGAGAGCAGCTCCATAAGGCCAT<br>GAAGAGATACGCACTGGTGCCTGGTACAATCGCATTTACCGACGCTCA<br>TATTGAGGTCGATATTACATACGCCGAATATTTCGAGATGTCCGTGAG<br>ACTCGCTGAGGCAATGAAGCGGTACGGGCTGAATACTAACCACAGGA<br>TCGTCGTGTGTTCAGAGAACAGCCTGCAGTTCTTCATGCCTGTGCTGG<br>GTGCTCTGTTCATTGGGGTTGCCGTTGCTCCAGCAAACGACATTTATA<br>ACGAGAGGGAACTGCTTAATAGCATGGGCATTAGCCAGCCGACAGTG<br>GTGTTTGTGAGTAAGAAAGGACTCCAAAAAATTCTGAACGTCCAGAAA<br>AAATTACCTATCATTCAGAAGATCATCATCATGGATAGCAAGACAGACT<br>ACCAGGGCTTTCAGAGCATGTATACCTTTGTGACCAGCCACCTGCCGC<br>CAGGGTTTAACGAGTATGATTTCGTACCCGAAAGCTTCGACCGGGACA<br>AAACCATCGCATTGATCATGAATTCCTCTGGGTCAACCGGCCTCCCTA<br>AAGGGGTAGCACTGCCACACCGAACTGCGTGCGTGCGCTTTAGCCAC<br>GCGAGGGATCCAATTTTTGGAAATCAGATTATCCCCGATACCGCCATA<br>CTGTCAGTAGTGCCATTCCACCACGGGTTTGGTATGTTCACCACACTT<br>GGGTATCTAATCTGTGGATTCAGAGTCGTCCTTATGTACCGCTTTGAA<br>GAGGAATTGTTTCTTCGATCCCTCCAGGACTACAAAATCCAATCCGCC<br>TTATTGGTGCCTACTCTGTTCTCCTTTTTCGCCAAGAGCACGCTGATC<br>GACAAATATGACCTGAGTAACCTCCATGAGATTGCTAGCGGTGGCGC<br>CCCCCTGAGCAAAGAGGTGGGCGAGGCAGTTGCTAAGCGCTTCCATC<br>TCCCTGGAATAAGACAGGGATACGGCCTAACAGAGACTACAAGTGCA<br>ATCTTAATTACACCCGAAGGCGATGACAAGCCCGGCGCTGTGGGAAA<br>GGTTGTACCTTTTTTTGAAGCCAAAGTGGTCGACCTCGATACTGGCAA<br>AACGCTAGGCGTCAACCAGCGCGGTGAGCTATGCGTTAGGGGCCCTA<br>TGATCATGAGTGGTTACGTGAACAACCCCGAAGCCACGAATGCGCTG<br>ATCGACAAGGATGGATGGTTGCATTCGGGAGATATCGCTTATTGGGAC<br>GAAGACGAGCACTTCTTCATAGTAGACCGACTGAAGAGCCTGATCAAG<br>TACAAGGGATACCAGGTGGCTCCCGCCGAGCTTGAGTCCATCCTCTT<br>GCAACACCCGAATATTTTCGATGCCGGGGTGGCTGGGCTGCCAGACG<br>ATGATGCCGGCGAACTTCCAGCTGCCGTCGTAGTGCTCGAGCACGGG<br>AAGACAATGACCGAAAAGGAGATCGTTGACTACGTGGCCTCACAAGT<br>GACCACTGCCAAAAAGCTTCGGGGAGGGGTGGTCTTCGTCGATGAGG<br>TCCCCAAAGGCTTGACCGGTAAGCTCGATGCACGGAAGATACGTGAA<br>ATTCTGATAAAGGCCAAAAAAGGCGGTAAGATAGCCGTTTGATAAGCT<br>GCCTTCTGCGGGGCTTGCCTTCTGGCCATGCCCTTCTTCTCTCCCTTG<br>CACCTGTACCTCTTGGTCTTTGAATAAAGCCTGAGTAGGAAGAGTACT-<br>[SEQ ID NO: 1] |
| Forward Primer | TAGAAACTGGGCTTGTCGAGAC [SEQ ID NO: 2] |
| Reverse Primer | CTTCCTACTCAGGCTTTATTCAAAGAC [SEQ ID NO: 3] |

LNP Formulation

SM-102, used as a comparative LNP, was purchased from Cayman Chemicals. Cholesterol and 1,2-distearoyl-sn-glycero-3-phosphocholine (DSPC) were purchased from VWR. 1,2-dimyristoyl-rac-glycero-3-methoxypolyethylene glycol-2000 (PEG-DMG) was purchased from Avanti Polar Lipids. A staggered herringbone microfluidic mixer was fabricated by soft lithography as previously reported [Chen, D. et al., Rapid discovery of potent siRNA-containing lipid nanoparticles enabled by controlled microfluidic formulation, J. Am. Chem. Soc. 134, 6948-6951, 2012]. Lipid components (50% ionizable lipid, 38.5% cholesterol, 10% DSPC, 1.5% PEG-DMG) were dissolved in ethanol, and RNA was dissolved in 75 mM sodium citrate (pH 3.0). LNPs were prepared by mixing the organic phase and the aqueous phase in the microfluidic chip at a total flow rate of 7 mL/min (aqueous: organic flow rate ratio of 2.5:1). Formulated LNPs were collected in a Slide-A-Lyzer™ Dialysis Cassette 10 K MWCO (ThermoScientific, 87729) and dialyzed twice at 1:1000 against 1× phosphate buffered saline (PBS) (pH 7.4) for 2 hours. LNPs were removed from the dialysis device, sterile filtered using a 0.2 μm polyethersulfone syringe filter (Whatman, Uniflo 13), and stored at 4° C. for up to 1 week prior to use.

LNP Size Distribution

LNPs were equilibrated at room temperature and diluted 1:100 in 1 mL of RNAse-free distilled water. Size distribution measurements were performed using a Zetasizer Nano (Malvern, Ltd. Malvern, UK) with a He—Ne ion laser of 633 nm.

mRNA Concentration and Encapsulation Efficiency

RNA concentration and encapsulation efficiency of LNPs were determined using a modified Quant-iT RiboGreen assay (ThermoFisher). The assay was performed in triplicates in a black opaque 96-well plate. Briefly, LNPs were either diluted at 1:50 in RNAse-free distilled water or in 2% TritonX. A standard curve with the corresponding RNA was prepared in 2% TritonX. The plate was incubated for 10 min at 37° C. to disrupt LNPs. RiboGreen reagent was then added to each well, and fluorescence intensity was measured with a Tecan Infinite M200 plate reader (480 nm/525 nm). The raw fluorescence values were subtracted by the background fluorescence, and the total RNA concentration in the LNP formulation was determined by linear interpolation of the standard curve. Encapsulation efficiency was calculated from the ratio of untreated to treated wells as previously reported [Walsh, C. et al., Microfluidic-Based Manufacture of siRNA-Lipid Nanoparticles for Therapeutic Applications, *Drug Delivery System* (ed. Jain, K. K.) vol. 1141 109-120 (Springer New York, 2014)].

Apparent $pK_a$

Determination of the apparent $pK_a$ of LNPs was carried out using a previously described protocol [Heyes, J., Palmer, L., Bremner, K. & MacLachlan, I., Cationic lipid saturation influences intracellular delivery of encapsulated nucleic acids, *J. Controlled Release* 107, 276-287, 2005; Zhang, J., Fan, H., Levorse, D. A. & Crocker, L. S., Ionization Behavior of Amino Lipids for siRNA Delivery: Determination of Ionization Constants, SAR, and the Impact of Lipid p K a on Cationic Lipid-Biomembrane Interactions, Langmuir 27, 1907-1914, 2011]. Briefly, a series of buffers with pH values varying by 0.5 between 3.0 and 8.5 were prepared by titrating a solution containing 10 mM citrate, 10 mM phosphate, 10 mM borate and 150 mM NaCl with 1.0 M HCl and aliquoted into a black 96-well plate. LNPs and 6-(p-toluidino)-2-naphthalenesulfonic acid (TNS, Sigma Aldrich) were diluted into these buffers at final concentration of 25 and 5.45 μM, respectively. The plate was equilibrated at room temperature for 20 min. Fluorescence intensity was determined using a Tecan Infinite M200 plate reader (325 nm/435 nm). The raw fluorescence values were normalized between 0 and 1 and fitted using graphing software to determine $pK_a$, which corresponds the pH value at 50% ionization.

Cryo Transmission Electron Microscopy (CryoTEM)

CryoTEM samples were prepared with the Vitrobot Mark IV System (ThermoScientific). To prepare CryoTEM grids, 4 μL of sample was applied to a Quantifoil R2/2 300 mesh grid (Electron Microscopy Sciences, Q325CR2). The following parameters were used: temperature=4° C., humidity=100%, wait time=5 s, blot time=2 s, blot force=2, drain time=0 s, number of blots=1. The images were taken on a Talos L120 C at an accelerating voltage of 120 kV and a 57000× magnification.

Intramuscular Firefly Luciferase mRNA Expression

C57BL/6 mice (female, 8-9 weeks old, 19-21 g, Charles River) were injected intramuscularly with LNPs (50 μL/quadricep) at 500 ng of Firefly Luciferase mRNA. 6 hours later, mice were injected intraperitoneally (200 μL) with 3 mg of D-luciferin (ThermoScientific), legs were harvested and imaged for bioluminescence (open filter, height=1 cm) within 10 min using an IVIS Spectrum (PerkinElmer). The total luminescent flux (photons/second) in the muscle was determined with the automatic region of interest tool.

In Vivo Gene Editing

Modified Cas9 mRNA was produced by IVT of a Cas9 DNA template (Sigma-Aldrich, CAS9P) with full substitution of uridine with $N^1$-methyl-pseudouridine-5'-Triphosphate (Table 9). Modified sgRNA with phosphorothioate bonds was purchased from Synthego (Table 13). LNPs were formulated with Cas9 mRNA and sgTOM (3/1, wt/wt) at a lipid nitrogen-to-RNA phosphate ratio (N/P) of 10. Female B6.Cg-Gt(ROSA)26Sor$^{tm9(CAG\text{-}tdTomato)Hze}$/J (Ai9) mice (The Jackson Laboratory, 8-9 weeks, n=2) were injected intramuscularly (50 μL) in one quadricep at 2 mg/kg of total RNA on day 0 and day 2. The other quadricep was simultaneously injected with 50 μL of 1×PBS. On day 5, hindlimb muscles were harvested and fluorescence (535 nm/600 nm) was detected with an IVIS Spectrum (PerkinElmer).

TABLE 9

Cas9 mRNA coding sequence.

| Name | DNA Sequence (5' to 3') |
|---|---|
| Cas9 mRNA coding sequence | ATGGACAAGAAGTACAGCATCGGCCTGGACATCGGCACCAACTCTGT<br>GGGCTGGGCCGTGATCACCGACGAGTACAAGGTGCCCAGCAAGAAAT<br>TCAAGGTGCTGGGCAACACCGACCGGCACAGCATCAAGAAGAACCTG<br>ATCGGCGCCCTGCTGTTCGACAGCGGAGAAACAGCCGAGGCCACCC<br>GGCTGAAGAGAACCGCCAGAAGAAGATACACCAGACGGAAGAACCG<br>GATCTGCTATCTGCAAGAGATTTTCAGCAACGAGATGGCCAAGGTGGA<br>CGACAGCTTCTTCCACAGACTGGAAGAGTCCTTCCTGGTGGAAGAGG<br>ATAAGAAGCACGAGCGGCACCCCATCTTCGGCAACATCGTGGACGAG<br>GTGGCCTACCACGAGAAGTACCCCACCATCTACCACCTGAGAAAGAA<br>ACTGGTGGACAGCACCGACAAGGCCGACCTGCGGCTGATCTATCTGG<br>CCCTGGCCCACATGATCAAGTTCCGGGGCCACTTCCTGATCGAGGGC<br>GACCTGAACCCCGACAACAGCGACGTGGACAAGCTGTTCATCCAGCT<br>GGTGCAGACCTACAACCAGCTGTTCGAGGAAAACCCCATCAACGCCA<br>GCGGCGTGGACGCCAAGGCCATCCTGTCTGCCAGACTGAGCAAGAG<br>CAGACGGCTGGAAAATCTGATCGCCCAGCTGCCCGGCGAGAAGAAGA<br>ATGGCCTGTTCGGCAACCTGATTGCCCTGAGCCTGGGCCTGACCCCC<br>AACTTCAAGAGCAACTTCGACCTGGCCGAGGATGCCAAACTGCAGCT<br>GAGCAAGGACACCTACGACGACGACCTGGACAACCTGCTGGCCCAGA<br>TCGGCGACCAGTACGCCGACCTGTTTCTGGCCGCCAAGAACCTGTCC<br>GACGCCATCCTGCTGAGCGACATCCTGAGAGTGAACACCGAGATCAC<br>CAAGGCCCCCCTGAGCGCCTCTATGATCAAGAGATACGACGAGCACC<br>ACCAGGACCTGACCCTGCTGAAAGCTCTCGTGCGGCAGCAGCTGCCT<br>GAGAAGTACAAAGAAATCTTCTTCGACCAGAGCAAGAACGGCTACGCC |

TABLE 9-continued

Cas9 mRNA coding sequence.

| Name | DNA Sequence (5' to 3') |
| --- | --- |
| | GGCTACATCGATGGCGGAGCCAGCCAGGAAGAGTTCTACAAGTTCAT<br>CAAGCCCATCCTGGAAAAGATGGACGGCACCGAGGAACTGCTCGTGA<br>AGCTGAACAGAGAGGACCTGCTGCGGAAGCAGCGGACCTTCGACAAC<br>GGCAGCATCCCCCACCAGATCCACCTGGGAGAGCTGCACGCCATTCT<br>GCGGCGGCAGGAAGATTTTTACCCATTCCTGAAGGACAACCGGGAAA<br>AGATCGAGAAGATCCTGACCTTCCGCATCCCCTACTACGTGGGCCCT<br>CTGGCCAGGGGAAACAGCAGATTCGCCTGGATGACCAGAAAGAGCGA<br>GGAAACCATCACCCCCTGGAACTTCGAGGAAGTGGTGGACAAGGGCG<br>CCAGCGCCCAGAGCTTCATCGAGCGGATGACCAACTTCGATAAGAAC<br>CTGCCCAACGAGAAGGTGCTGCCCAAGCACAGCCTGCTGTACGAGTA<br>CTTCACCGTGTACAACGAGCTGACCAAAGTGAAATACGTGACCGAGG<br>GAATGAGAAAGCCCGCCTTCCTGAGCGGCGAGCAGAAAAAGGCCATC<br>GTGGACCTGCTGTTCAAGACCAACCGGAAAGTGACCGTGAAGCAGCT<br>GAAAGAGGACTACTTCAAGAAAATCGAGTGCTTCGACTCCGTGGAAAT<br>CTCCGGCGTGGAAGATCGGTTCAACGCCTCCCTGGGCACATACCACG<br>ACCTGCTGAAGATTATCAAGGACAAGGACTTCCTGGACAATGAGGAAA<br>ACGAGGACATTCTGGAAGATATCGTGCTGACCCTGACACTGTTTGAGG<br>ACAGAGAGATGATCGAGGAACGGCTGAAAACCTATGCCCACCTGTTC<br>GACGACAAAGTGATGAAGCAGCTGAAGCGGCGGAGATACACCGGCTG<br>GGGCAGGCTGAGCCGGAAGCTGATCAACGGCATCCGGGACAAGCAG<br>TCCGGCAAGACAATCCTGGATTTCCTGAAGTCCGACGGCTTCGCCAA<br>CAGAAACTTCATGCAGCTGATCCACGACGACAGCCTGACCTTTAAAGA<br>GGACATCCAGAAAGCCCAGGTGTCCGGCCAGGGCGATAGCCTGCAC<br>GAGCACATTGCCAATCTGGCCGGATCCCCCGCCATTAAGAAGGGCAT<br>CCTGCAGACAGTGAAGATTGTGGACGAGCTCGTGAAAGTGATGGGCC<br>ACAAGCCCGAGAACATCGTGATCGAAATGGCCAGAGAGAACCAGACC<br>ACCCAGAAGGGACAGAAGAACAGCCGCGAGAGAATGAAGCGGATCG<br>AAGAGGGCATCAAAGAGCTGGGCAGCCAGATCCTGAAAGAACACCCC<br>GTGGAAAACACCCAGCTGCAGAACGAGAAGCTGTACCTGTACTACCT<br>GCAGAATGGGCGGGATATGTACGTGGACCAGGAACTGGACATCAACC<br>GGCTGTCCGACTACGATGTGGACCACATTGTGCCCCAGTCCTTCATCA<br>AGGACGACTCCATCGATAACAAAGTGCTGACTCGGAGCGACAAGAAC<br>CGGGGCAAGAGCGACAACGTGCCCTCCGAAGAGGTCGTGAAGAAGA<br>TGAAGAACTACTGGCGCCAGCTGCTGAATGCCAAGCTGATTACCCAG<br>AGGAAGTTCGACAATCTGACCAAGGCCGAGAGAGGCGGCCTGAGCG<br>AACTGGATAAGGCCGGCTTCATTAAGCGGCAGCTGGTGGAAACCCGG<br>CAGATCACAAAGCACGTGGCACAGATCCTGGACTCCCGGATGAACAC<br>TAAGTACGACGAGAACGACAAACTGATCCGGGAAGTGAAAGTGATCA<br>CCCTGAAGTCCAAGCTGGTGTCCGACTTCAGAAAGGATTTCCAGTTTT<br>ACAAAGTGCGCGAGATCAACAACTACCACCACGCCCACGACGCCTAC<br>CTGAACGCCGTCGTGGGAACCGCCCTGATCAAAAAGTACCCTAAGCT<br>GGAAAGCGAGTTCGTGTACGGCGATTACAAGGTGTACGACGTGCGGA<br>AGATGATCGCCAAGAGCGAGCAGGAAATCGGCAAGGCTACCGCCAAG<br>TACTTCTTCTACAGCAACATCATGAACTTTTTCAAGACCGAGATCACAC<br>TGGCCAACGGCGAGATCAGAAAGCGGCCTCTGATCGAGACAAACGGC<br>GAAACCGGGGAGATCGTGTGGGATAAGGGCCGGGATTTTGCCACAGT<br>GCGGAAAGTGCTGTCCATGCCCCAAGTGAATATCGTGAAAAAGACCG<br>AGGTGCAGACCGGCGGCTTCAGCAAAGAGTCTATCCTGCCCAAGAGG<br>AACTCCGACAAGCTGATCGCCAGAAAGAAGGATTGGGACCCTAAGAA<br>GTACGGCGGCTTTGACAGCCCCACCGTGGCCTACTCTGTGCTGGTGG<br>TGGCCAAAGTGGAAAAGGGCAAGTCCAAGAAACTGAAGAGTGTGAAA<br>GAGCTGCTGGGGATCACCATCATGGAAAGAAGCAGCTTCGAGAAGAA<br>TCCCATCGACTTTCTGGAAGCCAAGGGCTACAAAGAAGTGAAAAAGGA<br>CCTGATCATCAAGCTGCCTAAGTACTCCCTGTTCGAGCTGGAAAACGG<br>CCGGAAGCGGATGCTGGCTTCTGCCGGCGAACTGCAGAAGGGAAAC<br>GAGCTGGCCCTGCCCTCCAAATATGTGAACTTCCTGTACCTGGCCAG<br>CCACTATGAGAAGCTGAAGGGCTCCCCCGAGGATAATGAGCAGAAAC<br>AGCTGTTTGTGGAACAGCACAAGCACTACCTGGACGAGATCATCGAG<br>CAGATTAGCGAGTTCTCCAAGCGCGTGATCCTGGCCGATGCCAACCT<br>GGACAAGGTGCTGAGCGCCTACAACAAGCACCGGGATAAGCCCATCA<br>GAGAGCAGGCCGAGAATATCATCCACCTGTTTACCCTGACCAACCTG<br>GGAGCCCCTGCCGCCTTCAAGTACTTTGACACCACCATCGACCGGAA<br>GAGGTACACCAGCACCAAAGAGGTGCTGGACGCCACCCTGATCCACC<br>AGAGCATCACCGGCCTGTACGAGACACGGATCGACCTGTCTCAGCTG<br>GGAGGCGACCCCAAGAAAAAGCGCAAAGTGTGA [SEQ ID NO: 4] |

Chemical Parameter Predictions

The predicted Log D and $pK_a$ of ionizable lipids were determined using MarvinSketch 21.18. The molecular volumes of SM-102 and 1-28 used to predict the number of mRNA copies per particle were approximated using the volume( ) function of InstantJChem 21.20.0 which calculates the van der Waals volume.

Number of mRNA Copies Per Particle

The predicted number of mRNA copies per particle was calculated based on a previously reported method [Carrasco, M. J. et al., Ionization and structural properties of mRNA lipid nanoparticles influence expression in intramuscular and intravascular administration, Commun. Biol. 4, 1-15, 2021]. The predicted number is an overestimate since it utilizes the van der Waals volume of the ionizable lipid instead of the molecular volume. The actual number of mRNA copies per particle was calculated by dividing the concentration of encapsulated mRNA copies (obtained from the measurement of mRNA concentration and encapsulation efficiency) by the nanoparticle concentration. Nanoparticle concentration was measured by Nanoparticle Tracking Analysis (NanoSight NS300) at a 1:100 dilution in water.

IL-6 Detection in Draining Lymph Nodes

I-28 LNPs and SM-102 LNPs were formulated with modified Firefly Luciferase mRNA. C57BL/6 mice (female, 8-9 weeks old, 19-21 g, Charles River) were injected intramuscularly with LNPs (50 μL/quadricep) at 7.5 μg of mRNA or with saline. 6 hours post-injection, draining lymph nodes were harvested. The popliteal and inguinal lymph nodes were combined in Powerbead Tubes Qiagen) containing T-Per™ lysis buffer (ThermoScientific) in the presence of a Halt™ protease inhibitor cocktail (ThermoScientific). The samples were snap-frozen in a mixture of isopropanol and dry ice and stored at −80° C. Frozen samples were thawed on ice and homogenized using a bead mill homogenizer. Lysates were cleared by centrifugation, transferred to new tubes and stored at −80° C. until use. Undiluted samples were used for quantification of total protein content using the Pierce™ BCA Protein Assay Kit (ThermoScientific). IL-6 concentration was determined by enzyme-linked immunosorbent assay (RnD Systems). Each sample was assayed undiluted and diluted 1:1 in lysis buffer. Absorbance measurements were taken on a Biotek Synergy H1 plate reader. IL-6 concentrations were normalized on a per sample basis by dividing the IL-6 concentration by the total protein content. The normalized IL-6 concentrations from the undiluted and the diluted samples were averaged prior to plotting.

Statistics

Statistical analyses were performed using GraphPad Prism 8. Two-tailed unpaired t-tests were used to compare the means of two independent samples against each other. Two-tailed paired t-test was used to compare the mean difference between pairs of measurements. *P<0.05, P<0.01, *P<0.001, ****P<0.0001 was considered statistically significant.

Results

Design and Synthesis of Modular Ionizable Lipid Structure

A general synthesis strategy was devised to generate poly(amido amine) ionizable lipids of Formula I with three molecular regions that could be easily modified using commercial reagents, namely the amine core ($R^1$), linker length ($L^1$), and alkyl tail ($X^1$).

Iterative Screening Strategy of LNPs for Intramuscular mRNA Delivery

Figure 2:
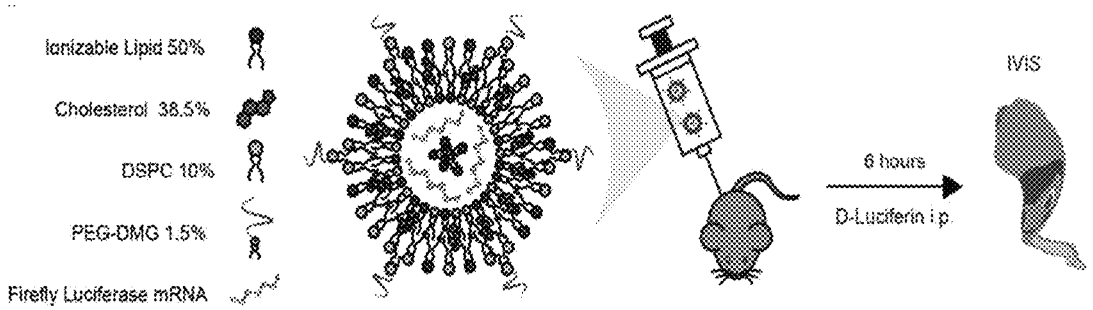
FIG. 2 is a schematic showing the contents of LNPs and their ratios and screening of LNPs for intramuscular delivery of firefly luciferase mRNA in C57BL/6 mice.

Ionizable lipids were formulated into LNPs based on the composition of Spikevax, consisting of an ionizable lipid, cholesterol, 1,2-distearoyl-sn-glycero-3-phosphocholine (DSPC), and 1,2-dimyristoyl-rac-glycero-3-methoxypolyethylene glycol-2000 (PEG-DMG) in a ratio of 50:38.5:10:1.5 mol % respectively (FIG. 2). All LNPs had a fixed NIP ratio of 5 to match the Spikevax formulation (Spikevax Full Prescribing Information, US FDA). The end goal was to build a new chemically distinct ionizable lipid that was noninferior to SM-102 for mRNA expression.

Design parameters with specific target criteria were used to guide the optimization process (Table 10). The average size of LNPs should be less than 200 nm to allow for sterile filtration, and the polydispersity index (PDI) should be smaller than 0.2 to make reproducible and stable formulations. Encapsulation efficiency refers to the fraction of encapsulated mRNA in the formulation. An encapsulation efficiency >90% maximizes mRNA delivery to cells and reduces immune activation induced by free transcripts [Karikó, K., Buckstein, M., Ni, H. & Weissman, D., Suppression of RNA Recognition by Toll-like Receptors: The Impact of Nucleoside Modification and the Evolutionary Origin of RNA, Immunity 23, 165-175, 2005]. The apparent pKa of an LNP is currently viewed as a relevant parameter for determining therapeutic efficacy. Apparent pKa should be between 6-7 such that LNPs are largely neutral at physiological conditions but become protonated and cationic in acidic endosomes and during formulation at low pH. For systemic delivery, a pKa range of 6.2-6.5 is optimal for liver expression [Jayaraman, M. et al., Maximizing the Potency of siRNA Lipid Nanoparticles for Hepatic Gene Silencing In Vivo, Angew. Chem. 124, 8657-8661, 2012], whereas for intramuscular delivery a slightly higher range of 6.6-6.9 has been reported by one study [Hassett, K. J. et al., Optimization of Lipid Nanoparticles for Intramuscular Administration of mRNA Vaccines, *Mol. Ther. Nucleic Acids* 15, 1-11, 2019].

TABLE 10

Design criteria for LNP characterization and performance

| Parameter | Method | Target criteria | Rationale |
|---|---|---|---|
| Size distribution | Dynamic light scattering | Z Average < 200 nm PDI < 0.2 | Particles smaller than 200 nm can be sterile filtered without compromising yield. A low PDI ensures reproducibility and regulatory compliance. |
| Encapsulation efficiency | RiboGreen assay | EE > 90% | Higher encapsulation efficiency improves mRNA delivery and reduces innate immune activation. |
| Apparent $pK_a$ | TNS assay | $6 < pK_a < 7$ | An apparent $pK_a$ between 6 and 7 improves endosomal release and confers a neutral surface charge at physiological pH (Jayaraman, 2012). |
| Total luminescent flux | IVIS | Non-inferior to SM-102 | SM-102 is an optimized lipid for intramuscular mRNA delivery (Hassett, 2019). |

Rather than synthesizing a large combinatorial library of ionizable lipids, an iterative approach informed by the design criteria in Table 10 to optimize the lipid structure was chosen. Briefly, LNPs were formulated with unmodified firefly luciferase mRNA, characterized, and injected in both quadriceps of C57BL/6 mice. Hindlimbs were harvested, and mRNA expression was determined by measuring the total luminescent flux in the muscle (FIG. 2). It was decided to start by optimizing the alkyl tails based on the assumption that they would have the largest impact on physical parameters. Then the linker length and amine core were investigated.

Ionizable Lipids Alkylation Methods

Two methods commonly used to alkylate amines from primary to tertiary were compared: epoxide ring-opening and reductive amination. Lipids with the same core and linker length were alkylated with symmetrical 14-carbon tails using either method (epoxide ring opening is shown on Scheme 1). The epoxide ring-opening reaction introduces a hydroxyl group at the beta position next to the tertiary amine (I-1), whereas reductive amination results in fully saturated tails (1-18). The LNP size distributions by intensity showed some differences (FIG. 3*d*). The apparent $pK_a$ of I-1-LNPs was 0.7 point lower than I-18-LNPs (FIG. 3*c* and FIG. 3*e*). The hydroxyl groups in I-1 pull electron density away from neighbouring amines through inductive effects, lowering their $pK_a$ compared to 1-18, which carries through into the formulated LNPs.

Prior to screening these formulations in mice, I-18-LNPs were expected to have a higher mRNA expression than I-1-LNPs based on a higher encapsulation efficiency and an apparent $pK_a$ within 6-7 (FIG. 3*e*). On the contrary, it has been found that I-1-LNPs had a higher luminescent flux than I-18-LNPs at all timepoints (FIG. 3*b*). The only structural difference between I-1 and 1-18 lipids is the presence of the hydroxyl groups, so it can be seen that an ionizable lipid's ability to form hydrogen bonds with nucleobases improves mRNA delivery [Cornebise, M. et al., Discovery of a Novel Amino Lipid That Improves Lipid Nanoparticle Performance through Specific Interactions with mRNA, *Adv. Funct. Mater.* 32, 2106727, 2022]. These results highlight the important role of hydrogen bonding for mRNA binding and delivery. Moving forward, epoxide ring-opening was chosen as the optimal alkylation method.

SM-102 was included in this first set of experiments to act as a benchmark, which emphasized the need to improve encapsulation efficiency, apparent $pK_a$ and mRNA delivery to meet the design criteria. Additionally, the highest luminescent flux was detected at 6 hours post-injection, and then decreased steadily over 96 hours for all LNPs (FIG. 3*b*). Therefore, the 6-hour timepoint was chosen in the following experiments to quantify mRNA expression.

Reducing Alkyl Tail Length Increased LNP $pK_a$ and mRNA Encapsulation Efficiency Epoxide ring-opening was used to alkylate lipids with shorter 10-carbon tails and longer 15-carbon tails (group $X^1$), maintaining the same $C_3$alkyl core (group $R^1$) and $C_2$alkyl linker (group $L^1$) (FIG. 4*a*). Tail lengths longer than 15 carbons could not be successfully formulated due to solubility issues. Initially ionizable lipids with longer tails were expected to interact more favourably with cellular membranes due to a higher lipophilicity nearing the predicted Log D of SM-102; instead, no significant differences in mRNA expression was found (FIG. 4*b*). Apparent $pK_a$ significantly depended on tail length, following an inverse relationship (FIG. 4*c*). While not wishing to be limited by theory, a 10-carbon tail may reduce the overall hydrophobic character of the LNPs in comparison to the longer tails. This could allow for greater partitioning of protons from the surrounding aqueous phase into the lipid phase of the particle, thus increasing the ionization of tertiary amines at higher pH values [Carrasco, M. J. et al., Ionization and structural properties of mRNA lipid nanoparticles influence expression in intramuscular and intravascular administration, Commun. Biol. 4, 1-15, 2021]. I-26 made LNPs with the highest $pK_a$ (6.3) and encapsulation efficiency (93%), which both met the design criteria (FIG. 4*e*). Therefore, a 10-carbon tail was chosen for the next structural iterations.

Increasing the Linker Length Increased Apparent $pK_a$ and mRNA Expression

To further optimize apparent $pK_a$, a lipid with a three-carbon linker (group $L^1$) was synthesized and compared to I-26 (FIG. 5*a*). It was predicted that increasing the distance between the amide bond and the tertiary amine would increase $pK_a$ by limiting through-bond inductive effects. As expected, the addition of one carbon atom in the linker increased apparent $pK_a$ by one unit (FIGS. 5*c* and 5*e*). I-27-LNPs had a significantly higher mRNA expression than I-26-LNPs (FIG. 5*b*) and maintained a high encapsulation efficiency and a desirable size distribution (FIGS. 5*d* and 5*e*). This result supports optimizing apparent $pK_a$ for mRNA delivery and shows that an apparent $pK_a$ near pH 7 is more favourable for intramuscular administration. As a result, the I-27 structure was chosen for subsequent optimization of the amine core.

Adding a Hydroxyl Group in the Amine Core Matched the Performance of SM-102

Given the improvement in mRNA expression achieved by including hydroxyls in the alkyl tails, 1-27 lipids with a hydroxyl group either two carbons (1-28) or three carbons (I 29) away from the core tertiary amine was synthesized (FIG. 6*a*). All LNPs met the characterization criteria (FIG. 6*d*, FIG. 6*e*, FIG. 6*f*), and the addition of a hydroxyl core significantly improved mRNA expression (FIG. 6*b*). 1-28, in particular, achieved a noninferior total luminescent flux to SM-102. Since the efficacy of LNPs has been shown to depend on mRNA chemical modifications, the experiment with LNPs delivering $n^1$-methyl-pseudouridine-modified mRNA was replicated and the same result was obtained (FIG. 6*c*) [Melamed, J. R. et al., Lipid nanoparticle chemistry determines how nucleoside base modifications alter mRNA delivery, *J. Controlled Release* 341, 206-214, 2022]. 1-28 therefore was chosen for intramuscular mRNA delivery.

Figure 7:
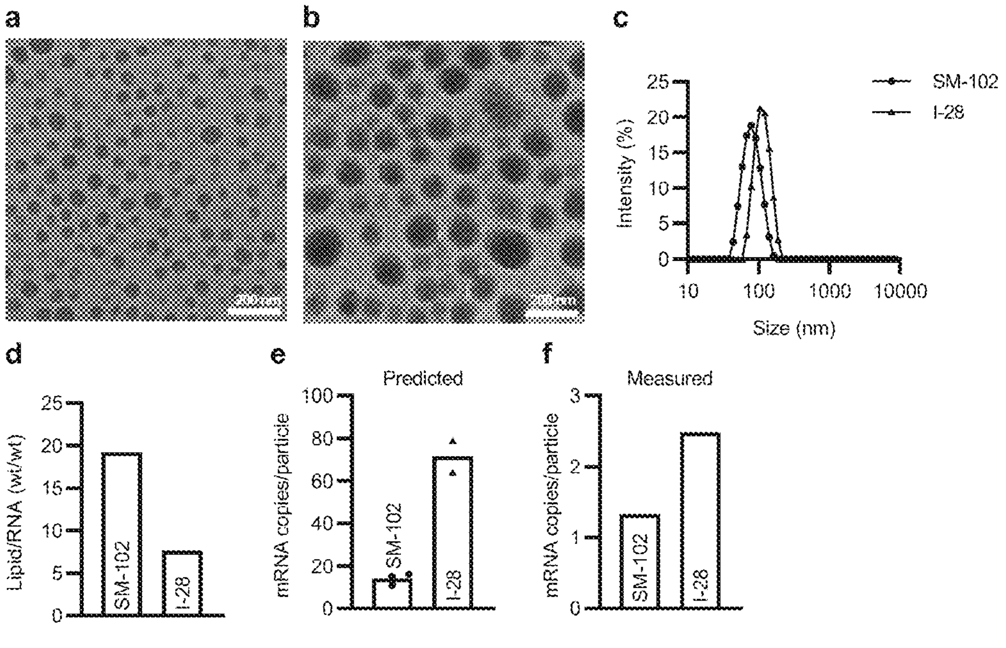
FIG. 7 *a-f* shows morphology and mRNA copies per particle of SM-102 and exemplary I-28-LNPs; a) CryoTEM image of SM-102 LNPs, scale bar=200 nm; b) CryoTEM image of exemplary 1-28 LNPs, scale bar=200 nm; c) nanoparticle size distribution of comparison compound SM-102 (•) and exemplary I-28 (▲); d) total lipid-to-RNA mass ratio for comparison compound SM-102 (left column) and exemplary 1-28 (right column); e) predicted number (mean) of mRNA copies per particle for comparison compound SM-102 (left column) and exemplary 1-28 (right column); and f) measured number of mRNA copies per particle for comparison compound SM-102 (left column) and exemplary 1-28 (right column).

I-28 made LNPs with 2.5-times less lipids than SM-102 (FIG. 7*d*) and formed larger particles (FIG. 7*a-c*). It was predicted and empirically confirmed that 1-28 encapsulated more mRNA copies per particle than SM-102 (FIG. 7*e*, FIG. 7*f* and Table 11). Therefore, it was decided to test whether 1-28 is a suitable delivery material for multi-RNA payloads.

TABLE 11

Parameters used to calculate the mRNA copies/LNP for different formulations.

| Formulation ID | Ionizable Lipid | Molecular Volume ($nm^3$) | Z Average (nm) | EE (%) | mRNA copies/ LNP |
|---|---|---|---|---|---|
| 1 | SM-102 | 0.804 | 84 | 99 | 15 |
| 9 | SM-102 | 0.804 | 86 | 96 | 16 |
| 11 | I-28 | 1.04 | 102 | 97 | 64 |
| 13 | SM-102 | 0.804 | 76 | 98 | 11 |
| 14 | I-28 | 1.04 | 109 | 95 | 79 |

Intramuscular CRISPR-Cas9 Gene Editing

Figure 8:
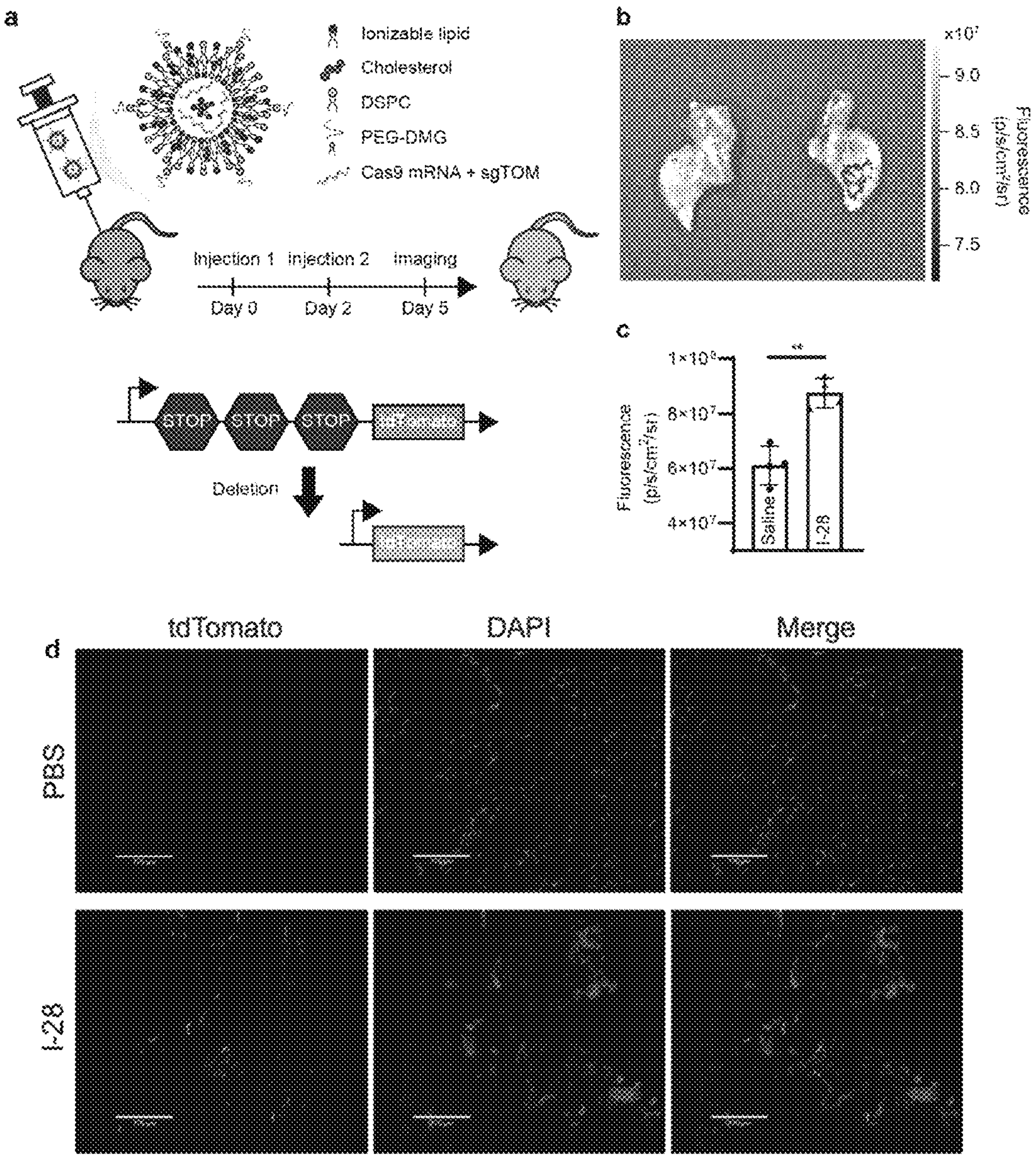
FIG. 8 *a-d* shows intramuscular gene editing in transgenic mice; a) schematic showing methods illustrating the removal of the triple STOP cassette by the CRISPR-cas9 system to enable expression of tdTomato; b) TdTomato fluorescence in the hindlimb muscle of Ai9 mice captured on an IVIS Spectrum (535 nm/600 nm), the left leg was treated with saline and the right leg was treated with exemplary I-28 LNPs; and c) TdTomato fluorescence (535 nm/600 nm) in the hindlimb muscle treated with saline (left) and with exemplary I-28 LNPs (right) (mean±s.d., n=4 hindlimbs, **p<0.01, unpaired two-tailed t-test). d) Histological and confocal microscopy analysis of Ai9 mouse hindlimb muscle after treatment with CRISPR-cas9 I-28 LNPs (bottom row). Phosphate buffered saline (PBS) served as negative controls (top row). In the tdTomato column (left), treatment with I-28 shows a tdTomato signal (white), confirming successful gene editing. A nuclear stain (DAPI, middle column) shows the nuclei in white. The tdTomato and DAPI signals are merged in the right column.

The ability of I-28-LNPs to perform intramuscular gene editing via co-delivery of Cas9 mRNA and sgRNA was evaluated. Genetically engineered mice that express the tdTomato fluorescent protein upon removal of a LoxP-flanked stop cassette were utilized. Once the stop cassette is deleted by the CRISPR-Cas9 system, gene edited cells become fluorescent and can be detected with an imaging system (FIG. 8*a*). I-28-LNPs were formulated with Cas9 mRNA and sgTOM (4/1 mRNA/sgRNA) (Tables 12 and 13). The N/P ratio was increased from 5 to 10 to achieve an encapsulation efficiency (>97%) that met the design criteria. Mice were injected intramuscularly at 2 mg/kg total RNA on day 0 and 2 and imaged on day 5 (FIG. 8*b*). This dosing regimen has been chosen based on previous reports to overcome the high level of background tissue fluorescence [Cheng, Q. et al., Selective organ targeting (SORT) nanoparticles for tissue-specific mRNA delivery and CRISPR-Cas gene editing, *Nat. Nanotechnol.* 15, 313-320, 2020; Wei, T., Cheng, Q., Min, Y.-L., Olson, E. N. & Siegwart, D. J., Systemic nanoparticle delivery of CRISPR-Cas9 ribonucleoproteins for effective tissue specific genome editing, *Nat. Commun.* 11, 3232, 2020]. Statistically significant tdTomato fluorescence was detected in the LNP-treated leg in comparison to the untreated leg, indicating that I-28-LNPs can be used to perform intramuscular gene edits and more generally to deliver large multi-RNA payloads (FIG. 8*c*). Successful gene editing was also confirmed via an orthogonal technique, where muscle tissues were analyzed by histology and confocal microscopy for the presence of tdTomato (FIG. 8*d*).

TABLE 12

Characterization summary of LNPs formulated in this study.

| Formulation ID | Ionizable Lipid | RNA Type | N/P | Total Lipids/RNA (wt/wt) | Z Average (nm) | PDI | EE (%) | $pK_a$ |
|---|---|---|---|---|---|---|---|---|
| 1 | SM-102 | Unmodified Fluc mRNA | 5 | 19.24 | 84 | 0.11 | 99 | 6.81 |
| 2 | I-18 | Unmodified Fluc mRNA | 5 | 8.29 | 116 | 0.12 | 95 | 6.25 |
| 3 | I-1 | Unmodified Fluc mRNA | 5 | 8.62 | 86 | 0.18 | 83 | 5.49 |
| 4 | I-1 | Unmodified Fluc mRNA | 5 | 8.62 | 148 | 0.08 | 83 | 5.23 |
| 5 | I-25 | Unmodified Fluc mRNA | 5 | 8.91 | 152 | 0.09 | 86 | 4.37 |
| 6 | I-26 | Unmodified Fluc mRNA | 5 | 7.46 | 173 | 0.12 | 93 | 6.26 |
| 7 | I-26 | Unmodified Fluc mRNA | 5 | 7.46 | 124 | 0.11 | 97 | 6.21 |
| 8 | I-27 | Unmodified Fluc mRNA | 5 | 7.60 | 95 | 0.15 | 96 | 7.16 |
| 9 | SM-102 | Unmodified Fluc mRNA | 5 | 19.24 | 86 | 0.17 | 96 | 6.61 |
| 10 | I-27 | Unmodified Fluc mRNA | 5 | 7.60 | 119 | 0.13 | 96 | 6.87 |
| 11 | I-28 | Unmodified Fluc mRNA | 5 | 7.61 | 102 | 0.12 | 97 | 6.76 |
| 12 | I-29 | Unmodified Fluc mRNA | 5 | 7.69 | 102 | 0.04 | 96 | 6.82 |
| 13 | SM-102 | Modified Fluc mRNA | 5 | 19.24 | 76 | 0.08 | 98 | 6.72 |
| 14 | I-28 | Modified Fluc mRNA | 5 | 7.61 | 109 | 0.04 | 95 | 6.88 |
| 15 | I-28 | Modified Cas9 mRNA/sgTOM | 10 | 15.20 | 179 | 0.04 | 97 | N/A |
| 16 | I-28 | Modified Cas9 mRNA/sgTOM | 10 | 15.20 | 191 | 0.07 | 99 | N/A |

TABLE 13 sgRNA targeting the stop cassettes.

| Name | DNA Sequence (5' to 3') |
|---|---|
| sgTOM | AAGTAAAACCTCTACAAATG [SEQ ID NO: 5] |
| PAM | TGG [SEQ ID NO: 6]] |

Discussion

An ionizable lipid structure containing three variable regions to enable fine-tuning of LNP properties has been devised. Instead of performing a large and resource intensive screen of each possible structure, an iterative design strategy to guide the discovery of a potent ionizable lipid, I-28 was employed. I-28-LNPs have a size of ~100 nm, a PDI<0.12, an encapsulation efficiency >95%, and achieve equivalent intramuscular mRNA expression to SM-102, thus meeting the design criteria that has been set out. As a result of its trivalency, I-28 uses 2.5-times less lipid than SM-102 at the same N/P ratio and encapsulate more mRNA copies per particle. Then, it was tested if I-28-LNP could deliver a large combinatorial RNA payload. As a proof-of-concept, the intramuscular gene editing by co-delivering Cas9 mRNA and sgRNAs in reporter mice has been successfully performed, albeit at a high dose.

Figure 3:
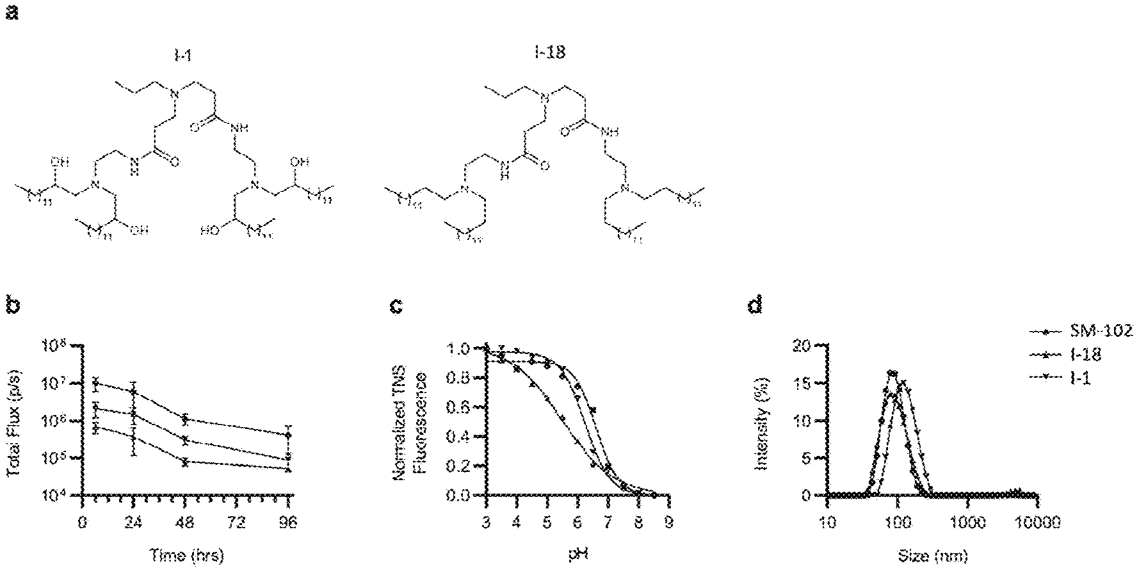
FIG. 3 *a-e* shows comparisons of alkylation methods; a) chemical structure of exemplary ionizable lipids alkylated via reductive amination (I-18) or epoxide-ring opening (I-1); b) total luminescent flux in the hindlimb muscle of C57BL/6 mice at 6, 24, 48 and 96 hours post-injection of SM-102 (•, top line), I-1 (▼, middle line) and I-18 (▲, bottom line) (mean±s.d., n=4 hindlimbs, **p<0.01, unpaired two-tailed t-test); c) results from the 6-(p-toluidino)-2-naphthalenesulfonic acid (TNS) assay for I-1 (▼) and SM-102 (•) and 1-18 (▲); d) nanoparticle size distribution by intensity for I-1 (▼) and SM-102 (•) and I-18 (▲); and e) summary of LNP characterization for SM-102, I-1 and I-18 showing results of size distributions, polydispersity index (PDI), encapsulation efficiency (EE) and pKa.
Figure 4:
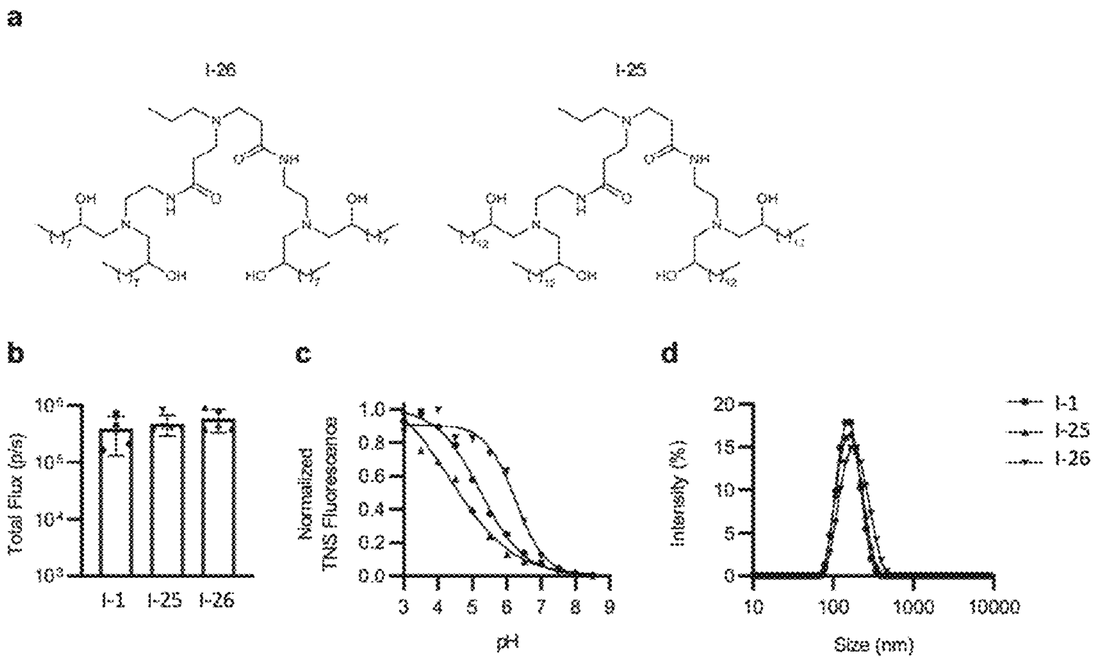
FIG. 4 *a-e* shows comparisons of alkyl tail lengths (group $X^1$); a) chemical structure of exemplary ionizable lipids alkylated via epoxide-ring opening with 10 (I-26) or 15 (I-25) carbon tails; b) total luminescent flux in the hindlimb muscle of C57BL/6 mice at 6 hours post-injection of (from left to right) I-1, I-26 and I-25 (mean±s.d., n=4 or 5 hindlimbs); c) TNS assay results for I-25 (▲), I-1 (•) and I-26 (▼); d) nanoparticle size distribution of I-25 (▲), I-1 (•) and I-26 (▼); and e) summary of LNP characterization for I-1, I-26 and I-25 showing results of size distributions, PDI, EE and pKa.
Figure 5:
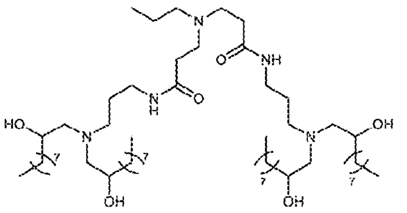
FIG. 5 *a-e* shows comparisons of linker lengths (group $L^1$); a) chemical structure of an exemplary ionizable lipid with a 3-carbon linker (I-27); b) total luminescent flux in the hindlimb muscle of C57BL/6 mice at 6 hours post-injection with 1-26 (•) and 1-27 (▲) (mean±s.d., n=4 or 6 hindlimbs, **p<0.01, unpaired two-tailed t-test); c) TNS assay results for I-26 (•) and I-27 (▲); d) nanoparticle size distribution for I-27 (▲) and I-26 (•); and e) summary of LNP characterization for I-26 and I-27 showing results of size distributions, PDI, EE and pKa.
Figure 5:
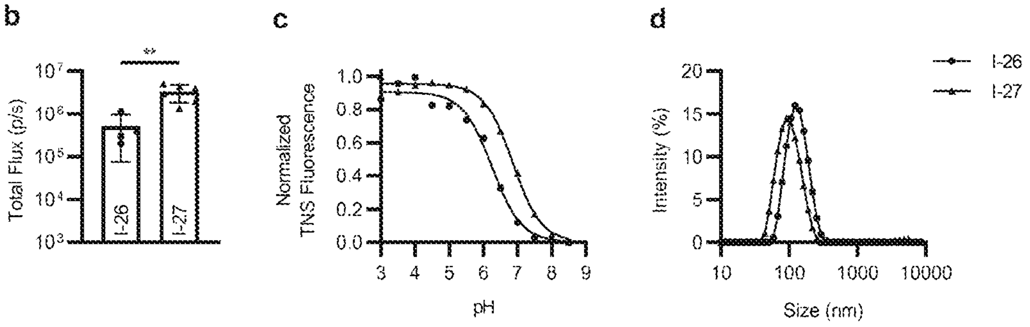
Figure 6:
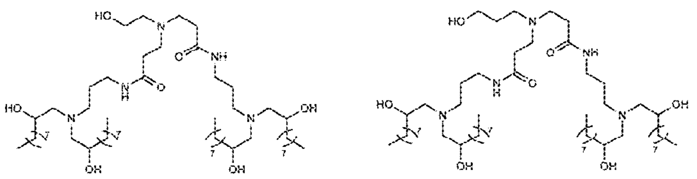
FIG. 6 *a-f* shows the effect of adding a hydroxyl group in the core (group $R^1$); a) chemical structure of exemplary ionizable lipids with an ethanolamine (I-28) or propanolamine (I-29) core; b) total luminescent flux in the hindlimb muscle of C57BL/6 mice injected with unmodified mRNA using (from left to right) comparison compound SM-102 and exemplary I-27, I-28 and I-29 (mean±s.d., n=8 or 10 hindlimbs, **p<0.01, *p<0.05, ns=not significant, unpaired two-tailed t-test); c) total luminescent flux in the hindlimb muscle of C57BL/6 mice injected with modified mRNA using comparison compound SM-102 (left) and exemplary I-28 (right) (mean±s.d, n=4, ns=not significant, unpaired two-tailed t-test); d) TNS assay results for SM-102 (•), I-27 (▲), I-28 (▼) and I-29 (♦); e) nanoparticle size distribution for SM-102 (•), I-27 (▲), I-28 (▼) and I-29; and f) summary of LNP characterization for SM-102, I-27, I-28 and I-29 showing results of size distributions, PDI, EE and pKa.
Figure 6:
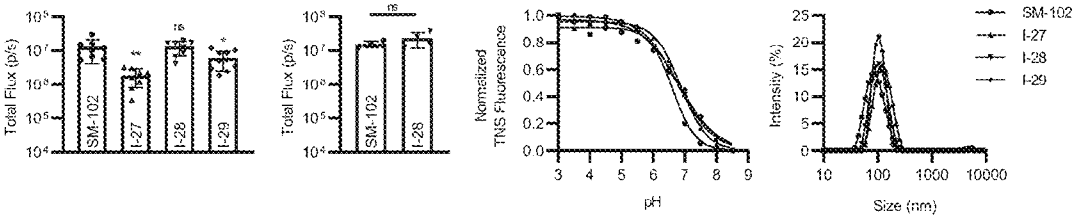

By independently optimizing the tail, linker, and core regions of the ionizable lipid, several findings regarding the effect of structural features on LNP performance were made. First, incorporation of hydroxyl groups next to tertiary amines in both the core and the tails significantly improved mRNA expression (FIGS. 3 and 6). While not wishing to be limited by theory, this could be because the hydrogen bonding increases lipid-mRNA interactions, but any role in cellular uptake and endosomal release remains unknown. Second, the study of lipids with a 2- or 3-carbon linker revealed that a $pK_a$ closer to pH 7 improves intramuscular mRNA expression (FIG. 5). Interestingly, both 1-28 and SM-102 LNPs have an apparent $pK_a$ in the range of 6.6-6.9, reinforcing its relevance as an design parameter for intramuscular mRNA delivery (Table 12) [Hassett, K. J. et al., Optimization of Lipid Nanoparticles for Intramuscular Administration of mRNA Vaccines, *Mol. Ther. Nucleic Acids* 15, 1-11, 2019]. Third, the lipophilicity of ionizable lipids (based on predicted Log D at pH 7.4) changes LNP physical parameters such as $pK_a$ and encapsulation efficiency but does not significantly affect mRNA expression (FIG. 4). The ionizable lipids that achieved the highest encapsulation efficiency had a relatively low Log D between 3.5 and 6.5, whereas another study has reported an optimal Log D range of 10 to 14 for systemic delivery (Table 13) [Rajappan, K. et al., Property-Driven Design and Development of Lipids for Efficient Delivery of siRNA, *J. Med. Chem.* 63, 12992-13012, 2020]. Therefore, the Log D is a parameter that does not affect intramuscular mRNA expression as much as hydrogen bonding and $pK_a$.

TABLE 13

Exemplary ionizable lipid predicted pKa and logD values.

| | I-18 | I-1 | I-25 | I-26 | I-27 | I-28 | I-29 |
|---|---|---|---|---|---|---|---|
| Predicted $pk_a$ | 8.993 | 8.163 | 8.163 | 8.163 | 8.881 | 8.629 | 8.798 |
| Predicted logD at pH 7.4 | 15.87 | 13.39 | 15.17 | 6.28 | 4.83 | 3.98 | 3.65 |

Figure 9:
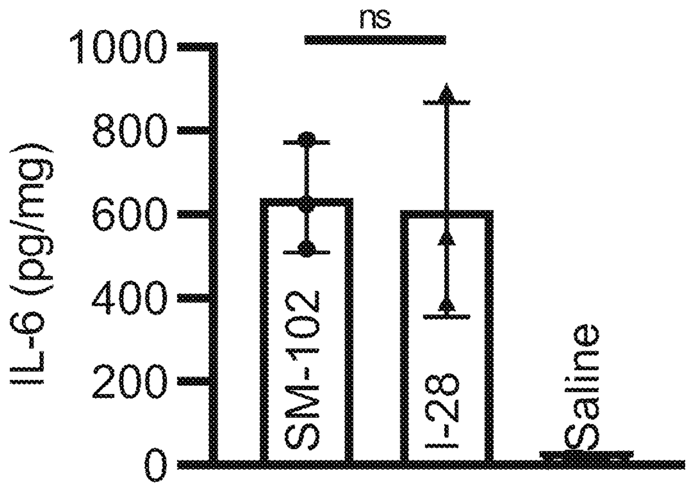
FIG. 9 shows the IL-6 response to comparison compound SM-102 (left bar) and exemplary I-28-LNPs (middle bar) compared to saline (right bar); IL-6 concentration (pg/mg total protein) in the draining lymph nodes of C57BL/6 mice 6 hours after injection (mean±s.d, n=3, ns=not significant, unpaired two-tailed t-test).

After discovering the high potency of 1-28, preliminary work on its IL-6 response was performed. IL-6 is an acute inflammatory cytokine that may enhance vaccine performance [Alameh, M.-G. et al., Lipid nanoparticles enhance the efficacy of mRNA and protein subunit vaccines by inducing robust T follicular helper cell and humoral responses, Immunity 54, 2877-2892.e7, 2021]. Compared to an SM-102 formulation used in vaccines, the 1-28 formulation led to similar IL-6 response. (FIG. 9).

In summary, a new ionizable lipid family has been designed and an optimized ionizable lipid, 1-28, for efficient intramuscular delivery of mRNA at a low dose of lipid has been identified. This study has reported structure-function findings regarding hydrogen bonding, ionization behavior and lipophilicity that lay a solid foundation for the design of LNPs for intramuscular mRNA delivery. A similar iterative design strategy could be used to investigate the effect of the ionizable lipid structure on LNP stability, in vivo clearance, tolerability, and immunogenicity, enabling the next generation of mRNA vaccines and therapeutics.

The invention claimed is:

1. A dendron or a salt and/or solvate thereof, wherein Generation 1 of the dendron has Formula (1):

$$R^1—N—(L^1—N(X^1)_2)_2, \quad (1)$$

wherein each $X^1$ is the same and is selected from the group consisting of

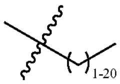,
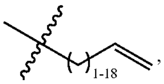,
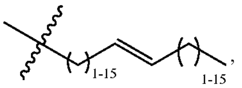,
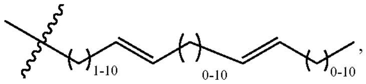,
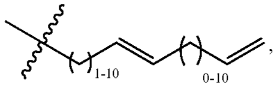,
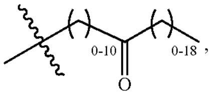,
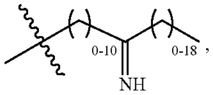,
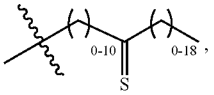,
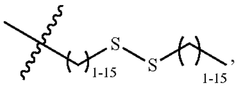,
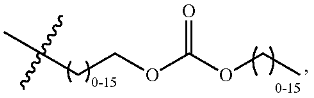,
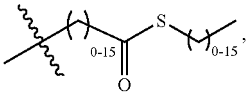,
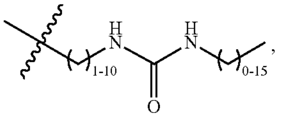,
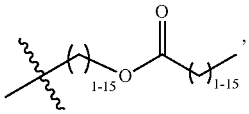,
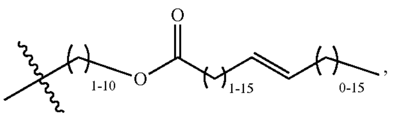,
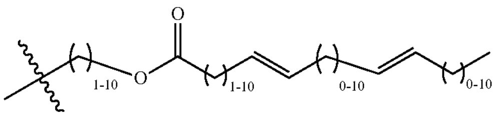 and
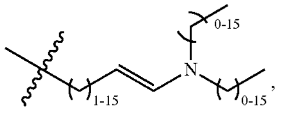, each of which is optionally substituted with one or two OH, one or two $NH_2$ and/or one or more fluorine;

Generation 2 of the dendron has Formula (2):

$$R^1—N—(L^1—N—(L^2—N(X^2)_2)_2)_2, \quad (2)$$

wherein each $X^2$ is the same and is selected from the group consisting of $C_{1-40}$alkyl and $C_{2-40}$alkenyl, wherein each alkyl and each alkenyl is optionally interrupted by one or more groups selected from the group consisting of —S—S—, —C(O)—, —OC(O)—, —C(O)O—, —OC(O)O—, —$NR_3$C(O)O—, —OC(O)$NR_3$—, —C(O)S—, —SC(O)—, —$NR_3$C(O)—, —C(O)$NR_3$—, —$NR_3$C(O)$NR_4$— and —C(N$C_{1-20}$ alkyl)-, wherein the alkyl and alkenyl are optionally substituted with one or more substituents selected from the group consisting of halo, $NR^5R^{5'}$ and OH, and wherein $R^3$, $R^4$, $R^5$ and $R^{5'}$ are each independently hydrogen or $C_{1-10}$ alkyl; or Generation 3 of the dendron has Formula (3):

$$R^1—N—(L^1—N—(L^2—N—(L^3—N(X^3)_2)_2)_2)_2, \quad (3)$$

wherein each $X^3$ is the same and is selected from the group consisting of $C_1$-40alkyl and $C_{2-40}$alkenyl, wherein each alkyl and each alkenyl is optionally interrupted by one or more groups selected from the group consisting of —S—S—, —C(O)—, —OC(O)—, —C(O)O—, —OC(O)O—, —$NR^3$C(O)O—, —OC(O)$NR^3$—, —C(O)S—, —SC(O)—, —$NR^3$C(O)—, —C(O)$NR^3$—, —$NR^3$C(O)$NR^4$— and —C(N$C_{1-20}$ alkyl)-, wherein the alkyl and alkenyl are optionally substituted with one or more substituents selected from the group consisting of halo, $NR^5R^{5'}$ and OH, and wherein $R^3$, $R^4$, $R^5$ and $R^{5'}$ are each independently hydrogen or $C_{1-10}$ alkyl;

wherein in Formula (1), Formula (2), and Formula (3):

$R^1$ is selected from the group consisting of $C_{1-10}$ alkyl, $C_{2-10}$ alkenyl, $C_{2-10}$ alkynyl, $C_{1-10}$ alkylenePh, $C_{1-10}$ alkyleneheteroaryl, $C_{1-10}$ alkylene$C_{5-6}$heterocycloalkyl, $C_{1-10}$ alkylene $C_{5-6}$ cycloalkyl and $C_1$-4 alkylene-S—S—$C_{1-4}$ alkyl, each of which is unsubstituted or substituted with one to four of OH, $OC_{1-15}$ alkyl, $C(O)OC_{1-15}$ alkyl and $NR^2R^{2'}$ and/or one or more fluoro, the phenyl, heteroaryl, heterocycloalkyl and cycloalkyl groups are additionally optionally substituted with one to four of $C_{1-4}$ alkyl and $C_{1-4}$ fluoroalkyl, wherein $R^2$ and $R^{2'}$ are independently selected from the group consisting of H and $C_{1-10}$ alkyl;

each $L^1$, $L^2$, and $L^3$ is the same or different and is a Linking Group, wherein each Linking Group is independently selected from the group consisting of:

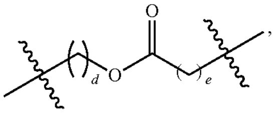,
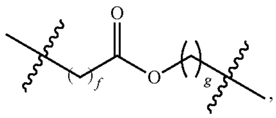,
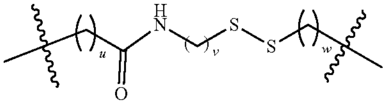
and
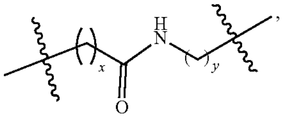, wherein d, e, f, g, u, v, w, x and y are each independently 1, 2, 3, 4, 5, or 6; and each available hydrogen atom bonded to a carbon atom is independently optionally replaced with a fluorine atom.

2. The dendron of claim 1, wherein $R^1$ is selected from the group consisting of:

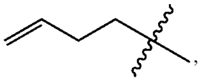,
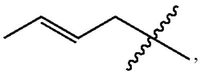,
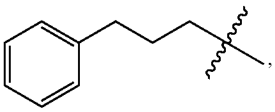,
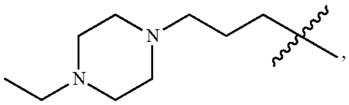,
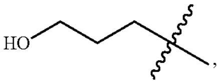,
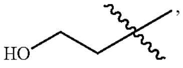, $C_3F_7$, $C_5H_{11}$, $C_6H_{13}$,

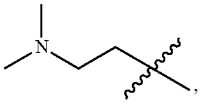,
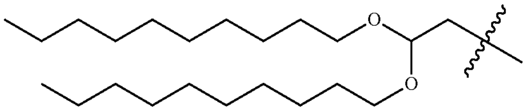
and
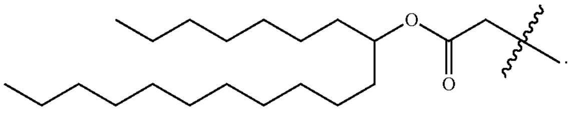.

3. The dendron of claim 1, wherein each $L^1$ in Formula 1 is the same, or each $L^2$ in Formula 2 is the same.

4. The dendron of claim 1, wherein $X^2$ is selected from the group consisting of:

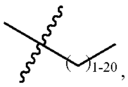,
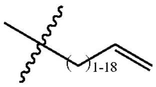,
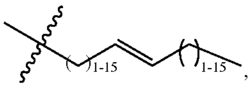,
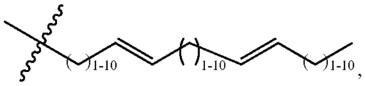,
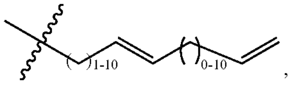,
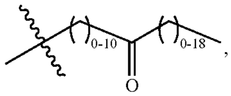,
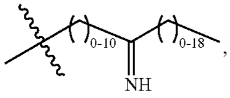,
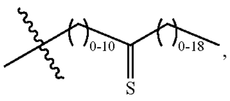,
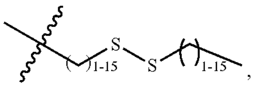,
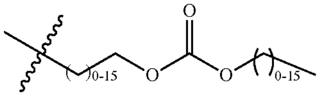,
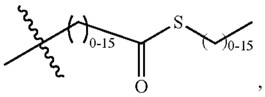,
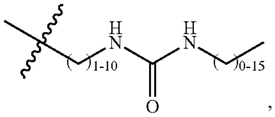,
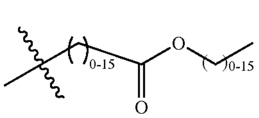,
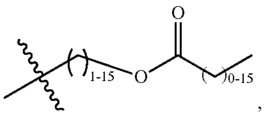,
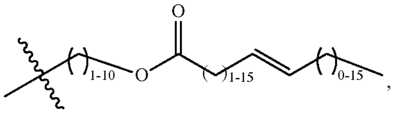,
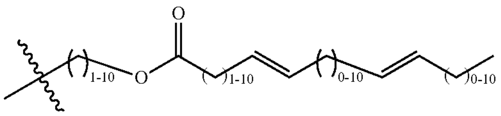
and
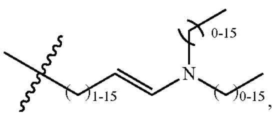, each of which is optionally substituted with one or two OH, one or two $NH_2$ and/or one or more fluorine, provided that the total number of carbon atoms in $X^2$ is 20 or less.

5. The dendron of claim 1, wherein the dendron is selected from the group consisting of:

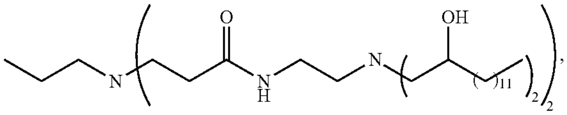,
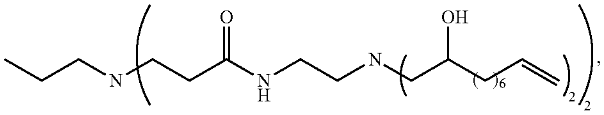,
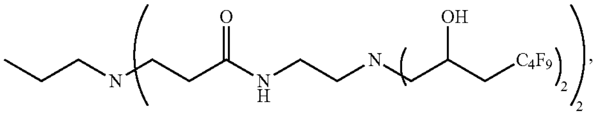,
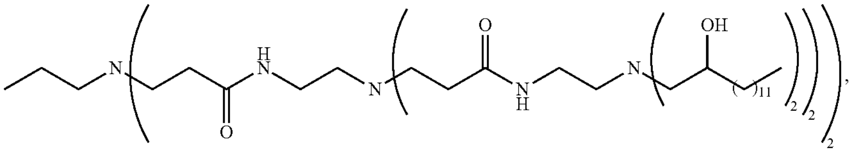,
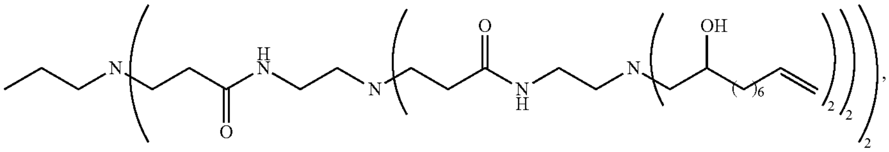,
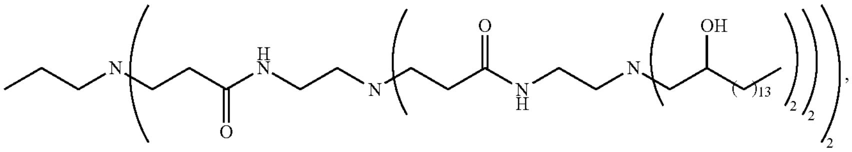,
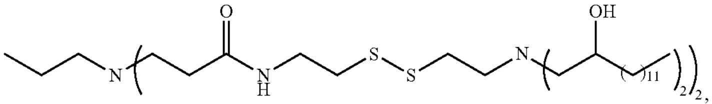,
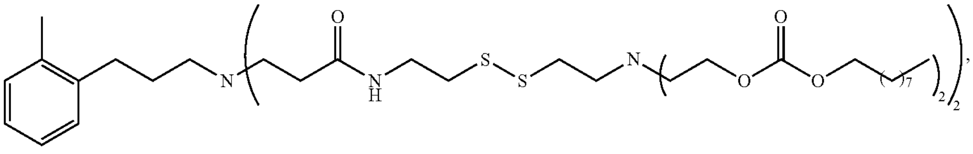,
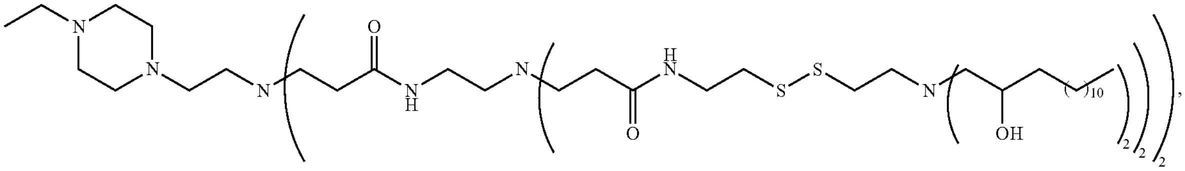,
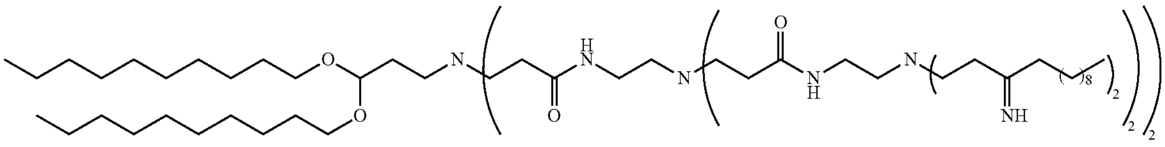,
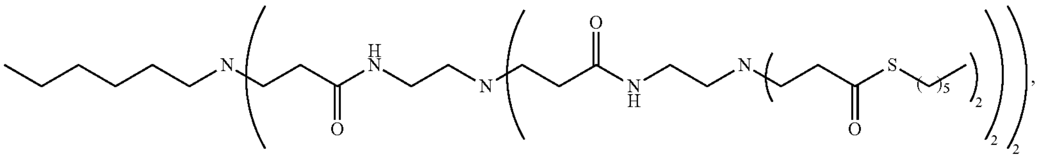,
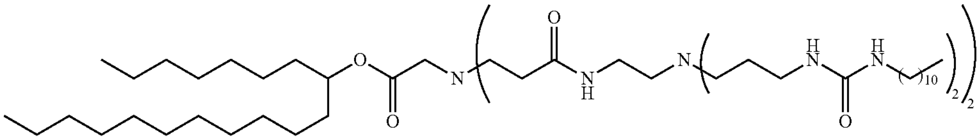, -continued
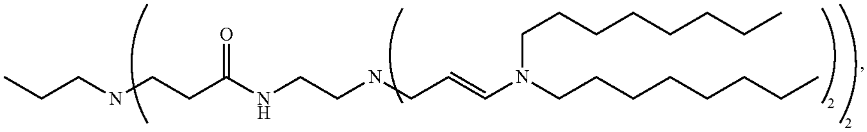,
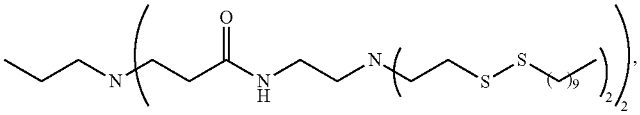, 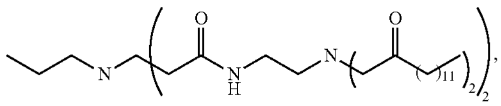,
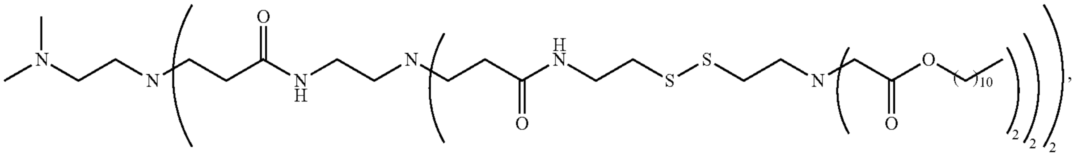,
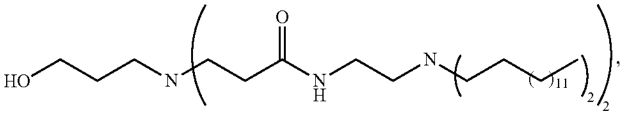,
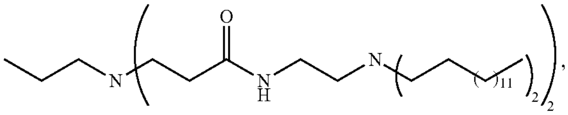,
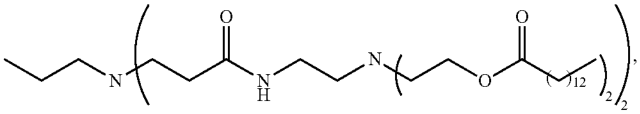,
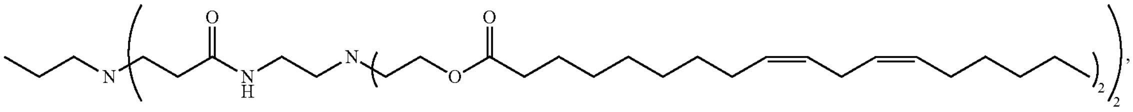,
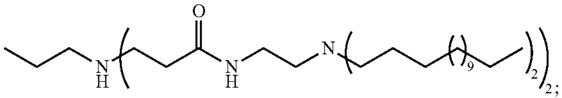; 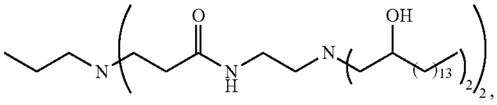,
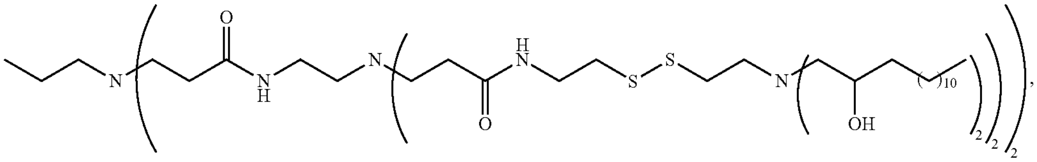,
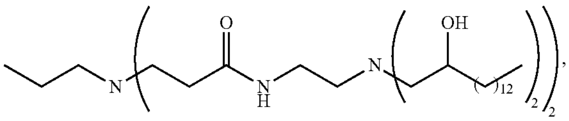, 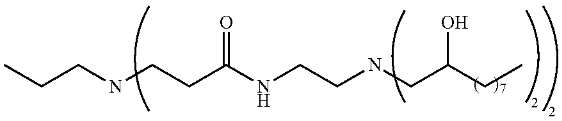,
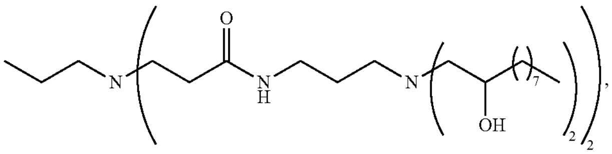,
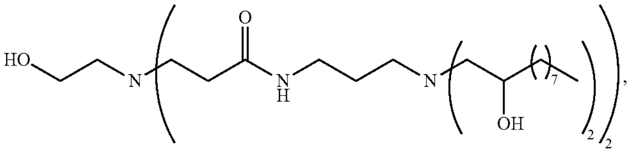,
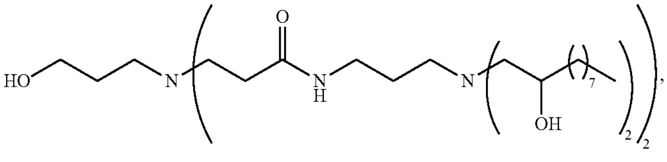, -continued
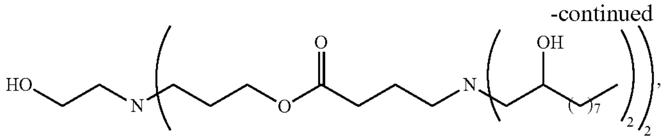,
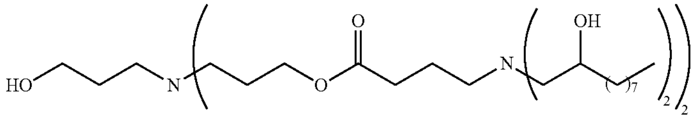,
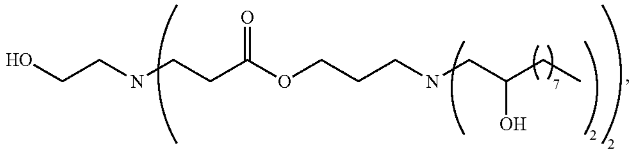, and
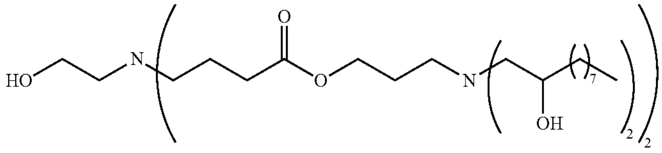
or a salt and/or solvate thereof.
6. The dendron of claim 1, wherein the dendron is selected from the group consisting of:
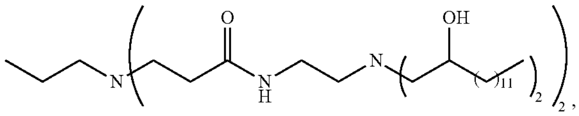, 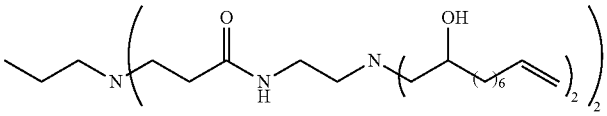,
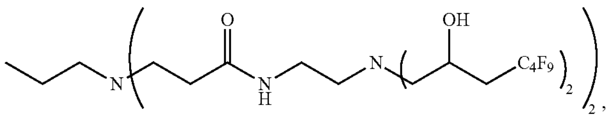,
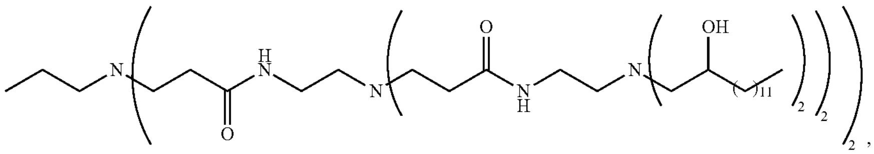,
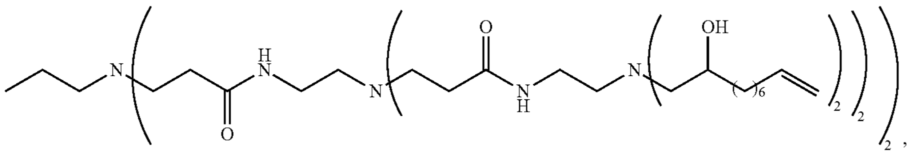,
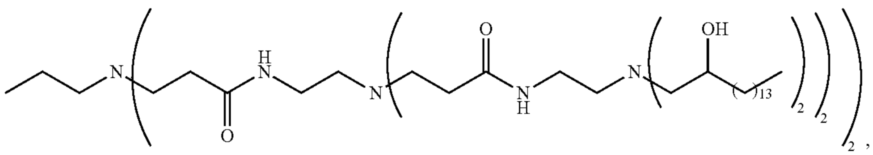,
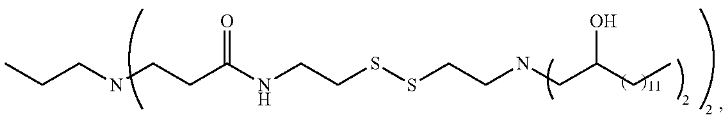,
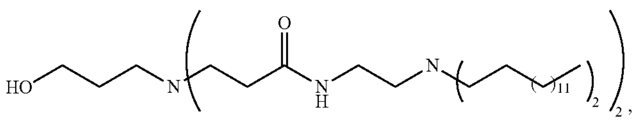, -continued

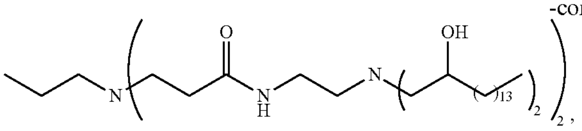
,

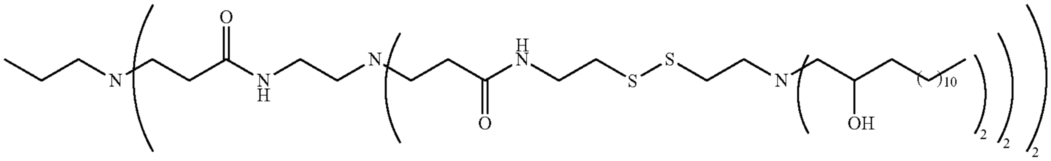
,

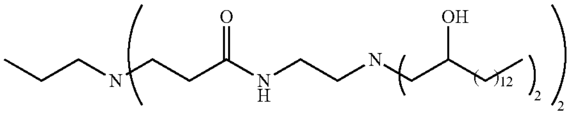
,
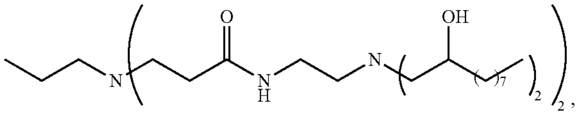
,

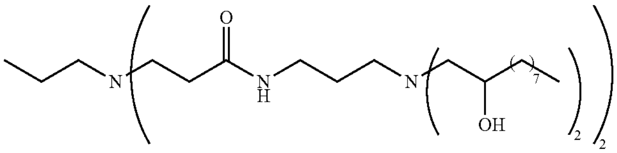
,

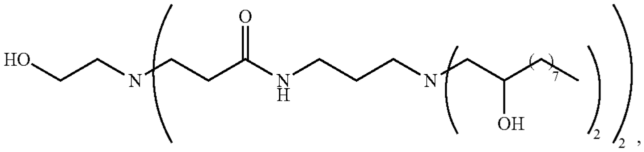
, and

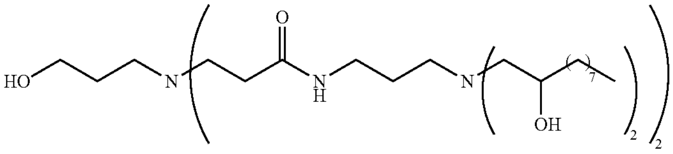
, or a salt and/or solvate thereof.

7. The dendron of claim 1, wherein the dendron of Formula 1 is:

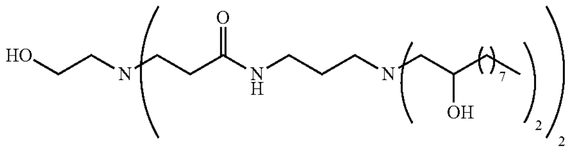
.

8. A nanoparticle comprising one or more dendrons of claim 1.

9. A colloid comprising one or more dendrons of claim 1.

10. A supramolecular structure comprising one or more dendrons of claim 1.

11. A composition comprising one or more dendrons of claim 1, and a therapeutic agent.

12. The composition of claim 11, wherein the composition has a pKa of about 4 to about 8.

13. A composition of claim 11, further comprising a chemically modified polynucleotide.

14. The composition of claim 13, wherein the composition has a pKa of about 5 to about 7.

15. The composition of claim 13, wherein the nanoparticles have mean diameter of about 50 nm to about 200 nm.

16. A lipid nanoparticle (LNP) comprising the nanoparticle of claim 8.

17. The LNP of claim 16, comprising one or more lipids.

18. The LNP of claim 17, wherein the one or more lipids are selected from a steroid, a steroid derivative, a PEG-lipid, and a phospholipid, and mixtures thereof.

* * * * *